(12) United States Patent
Gilligan et al.

(10) Patent No.: US 12,105,106 B2
(45) Date of Patent: Oct. 1, 2024

(54) PROCESS MODULE FOR AN AUTOMATED BIOLOGY SYSTEM

(71) Applicant: AIXINNO LIMITED, Cambridge (GB)

(72) Inventors: Patrick Clemente Gilligan, Cambridge (GB); Kenneth B. K. Teo, Cambridge (GB); David Anthony Bullinaria, Cambridgeshire (GB)

(73) Assignee: AIXINNO LIMITED, Cambridge (GB)

( * ) Notice: Subject to any disclaimer, the term of this patent is extended or adjusted under 35 U.S.C. 154(b) by 670 days.

(21) Appl. No.: 17/294,352

(22) PCT Filed: Nov. 16, 2018

(86) PCT No.: PCT/EP2018/081641
§ 371 (c)(1),
(2) Date: May 14, 2021

(87) PCT Pub. No.: WO2020/098957
PCT Pub. Date: May 22, 2020

(65) Prior Publication Data
US 2022/0011331 A1 Jan. 13, 2022

(51) Int. Cl.
*G06F 7/00* (2006.01)
*B01L 1/02* (2006.01)
(Continued)

(52) U.S. Cl.
CPC .............. *G01N 35/025* (2013.01); *B01L 1/02* (2013.01); *C12M 23/44* (2013.01);
(Continued)

(58) Field of Classification Search
CPC ....... G01N 35/025; G01N 2035/00326; G01N 2035/0418; G01N 2035/0465; B01L 1/02;
(Continued)

(56) References Cited

U.S. PATENT DOCUMENTS

| 4,654,727 A | 3/1987 | Blum et al. |
| 5,088,231 A | 2/1992 | Kertz |
| (Continued) | | |

FOREIGN PATENT DOCUMENTS

| CN | 104777321 | 7/2015 |
| EP | 1 900 806 A1 | 3/2008 |
| (Continued) | | |

OTHER PUBLICATIONS

International Search Report dated Aug. 26, 2019, from ISA/European Patent Office, for International Patent Application No. PCT/EP2018/081641 filed Nov. 16, 2018, 4 pgs.
(Continued)

*Primary Examiner* — P. Kathryn Wright
(74) *Attorney, Agent, or Firm* — Ascenda Law Group, PC

(57) ABSTRACT

A process module for a biology laboratory system includes a housing, a working deck located within the housing, having working deck plate slots for receiving cell culture plates, a liquid handling robot comprising at least one pipette for aspirating a liquid medium, and a first transfer interface in communication with a first storage module for storing cell culture plates. The working deck is movable to a plurality of working positions. In one of the positions, the cell culture plate is located under an operating point of the liquid handling robot. In another of the positions, the cell culture plate is in alignment with the first transfer interface for transfer of the cell culture plate between an outside of the housing and the working deck plate slot. The first transfer interface or a second interface can be brought in communication with a second storage module for storing lab-ware or liquid material.

8 Claims, 22 Drawing Sheets

(51) Int. Cl.
*B65G 49/00* (2006.01)
*C12M 3/00* (2006.01)
*G01N 35/02* (2006.01)
*G01N 35/00* (2006.01)
*G01N 35/04* (2006.01)

(52) U.S. Cl.
CPC ... *B01L 2200/028* (2013.01); *B01L 2200/141* (2013.01); *B01L 2300/0829* (2013.01); *C12M 23/48* (2013.01); *G01N 2035/00326* (2013.01); *G01N 2035/0418* (2013.01); *G01N 2035/0465* (2013.01)

(58) Field of Classification Search
CPC ......... B01L 2200/028; B01L 2200/141; B01L 2300/0829; C12M 23/44; C12M 23/48
See application file for complete search history.

(56) References Cited

U.S. PATENT DOCUMENTS

| | | | |
|---|---|---|---|
| 6,146,592 | A | 11/2000 | Kawashima et al. |
| 6,360,792 | B1 | 3/2002 | Ganz et al. |
| 6,467,285 | B2 | 10/2002 | Felder et al. |
| 6,691,748 | B1 | 2/2004 | Tajima |
| 7,013,198 | B2 | 3/2006 | Haas |
| 7,670,553 | B2 | 3/2010 | Babson |
| 7,883,887 | B2 | 2/2011 | Takagi et al. |
| 8,652,829 | B2 | 2/2014 | Bellalou et al. |
| 9,057,715 | B2 | 6/2015 | Kim et al. |
| 9,388,374 | B2 | 7/2016 | Hung et al. |
| 2001/0019065 | A1 | 9/2001 | William et al. |
| 2002/0090320 | A1 | 7/2002 | Burow et al. |
| 2003/0175164 | A1 | 9/2003 | Micklash et al. |
| 2004/0151628 | A1 | 8/2004 | Honkanen et al. |
| 2005/0058574 | A1 | 3/2005 | Bysouth et al. |
| 2007/0059205 | A1 | 3/2007 | Ganz et al. |
| 2009/0117620 | A1* | 5/2009 | Fritchie ................ B01L 3/5085  422/68.1 |
| 2010/0211211 | A1* | 8/2010 | Nedu ................ G01N 35/0099 700/218 |
| 2013/0050692 | A1 | 2/2013 | Tang et al. |
| 2013/0130361 | A1 | 5/2013 | Okano et al. |
| 2014/0178169 | A1* | 6/2014 | Hebert ................ G01N 35/025 414/807 |
| 2014/0196550 | A1 | 7/2014 | Chernomorsky et al. |
| 2014/0273242 | A1 | 9/2014 | Ochranek et al. |
| 2016/0003859 | A1 | 1/2016 | Wenczel et al. |
| 2016/0145555 | A1* | 5/2016 | Ingber ................ C12M 29/20 435/29 |
| 2016/0201022 | A1 | 7/2016 | Ozaki et al. |
| 2016/0304821 | A1 | 10/2016 | Ito |
| 2017/0036833 | A1 | 2/2017 | Takeuchi et al. |
| 2017/0145366 | A1 | 5/2017 | Magnant |
| 2017/0292967 | A1* | 10/2017 | Kim ................ G01N 33/491 |
| 2018/0044624 | A1 | 2/2018 | Shiraiwa |
| 2018/0164334 | A1* | 6/2018 | Yago ................ G01N 35/026 |
| 2018/0202908 | A1* | 7/2018 | Croquette ............ G01N 35/00 |
| 2018/0282682 | A1 | 10/2018 | Pebay et al. |

FOREIGN PATENT DOCUMENTS

| | | |
|---|---|---|
| EP | 2 068 155 A2 | 6/2009 |
| EP | 1 573 340 B1 | 9/2012 |
| EP | 3 078 736 A1 | 10/2016 |
| EP | 2 733 196 A1 | 4/2017 |
| EP | 3 229 028 A1 | 10/2017 |
| JP | H01 1189561 | 7/1989 |
| JP | 2004-166558 A | 6/2004 |
| JP | 2009-291869 A | 12/2009 |
| NL | 8801951 A | 3/1990 |
| WO | 93/03891 A1 | 3/1993 |
| WO | 03/008103 A1 | 1/2003 |
| WO | 2011/047710 A1 | 4/2011 |
| WO | 2016/130964 A1 | 8/2016 |
| WO | 2017184244 A1 | 10/2017 |
| WO | 2017221155 A1 | 12/2017 |

OTHER PUBLICATIONS

Written Opinion dated Aug. 26, 2019, from ISA/European Patent Office, for International Patent Application No. PCT/EP2018/081641 filed Nov. 16, 2018, 9 pgs.
International Search Report dated Sep. 30, 2019, from ISA/European Patent Office, for International Patent Application No. PCT/EP2018/081644 filed Nov. 16, 2018, 7 pgs.
Written Opinion dated Sep. 30, 2019, from ISA/European Patent Office, for International Patent Application No. PCT/EP2018/081644 filed Nov. 16, 2018, 9 pgs.
International Search Report dated Oct. 21, 2019, from ISA/European Patent Office, for International Patent Application No. PCT/EP2018/081645 filed Nov. 16, 2018, 9 pgs.
Written Opinion dated Oct. 21, 2019, from ISA/European Patent Office, for International Patent Application No. PCT/EP2018/081645 filed Nov. 16, 2018, 17 pgs.
International Search Report dated Oct. 21, 2019, from ISA/European Patent Office, for International Patent Application No. PCT/EP2018/081647 filed Nov. 16, 2018, 9 pgs.
Written Opinion dated Oct. 21, 2019, from ISA/European Patent Office, for International Patent Application No. PCT/EP2018/081647 filed Nov. 16, 2018, 16 pgs.
Restriction Requirement dated Jun. 6, 2024, for U.S. Appl. No. 17/294,363, filed May 14, 2021, 8 pgs.
Final Office Action dated Jul. 24, 2024, for U.S. Appl. No. 17/294,360, filed May 14, 2021, 27 pgs.
Non-Final Office Action dated Jun. 4, 2024, for U.S. Appl. No. 17/294,372, filed May 14, 2021, 18 pgs.
Amendment filed Jul. 1, 2024, for U.S. Appl. No. 17/294,360, filed May 14, 2021, 11 pgs.
Non-Final Office Action dated Mar. 29, 2024, for U.S. Appl. No. 17/294,360, filed May 14, 2021, 27 pgs.
Article 34 Amendment filed Sep. 17, 2020, for International Patent Application No. PCT/EP2018/081641 (filed Nov. 16, 2018), 12 pgs.
International Preliminary Report on Patentability dated Jan. 27, 2021, from the IPEA/European Patent Office, for International Patent Application No. PCT/EP2018/081641 (filed Nov. 16, 2018), 12 pgs.
Article 34 Amendment filed Sep. 17, 2020, for International Patent Application No. PCT/EP/2018/081644 (filed Nov. 16, 2018), 9 pgs.
Invitation to Restrict or Pay Additional Fees mailed Oct. 21, 2020, from the IPEA/European Patent Office, for International Patent Application No. PCT/EP/2018/081644 (filed Nov. 16, 2018), 3 pgs.
International Preliminary Report on Patentability dated Mar. 10, 2021, from the IPEA/European Patent Office, for International Patent Application No. PCT/EP/2018/081644 (filed Nov. 16, 2018), 11 pgs.
Article 34 Amendment filed Sep. 17, 2020, for International Patent Application No. PCT/EP2018/081645 (filed Nov. 16, 2018), 23 pgs.
Article 34 Amendment filed Apr. 15, 2021, for International Patent Application No. PCT/EP2018/081645 (filed Nov. 16, 2018), 6 pgs.
Invitation to Restrict or Pay Additional Fees mailed Jan. 22, 2021, from the IPEA/European Patent Office, for International Patent Application No. PCT/EP2018/081645 (filed Nov. 16, 2018), 3 pgs.
International Preliminary Report on Patentability dated May 25, 2021, from the IPEA/European Patent Office, for International Patent Application No. PCT/EP2018/081645 (filed Nov. 16, 2018), 34 pgs.
Article 34 Amendment filed Sep. 18, 2020, for International Patent Application No. PCT/EP2018/081617 (filed Nov. 16, 2018), 12 pgs.
Invitation to Restrict or Pay Additional Fees mailed Nov. 12, 2020, from the IPEA/European Patent Office, for International Patent Application No. PCT/EP2018/081617 (filed Nov. 16, 2018), 3 pgs.
International Preliminary Report on Patentability dated Apr. 12, 2021, from the IPEA/European Patent Office, for International Patent Application No. PCT/EP2018/081617 (filed Nov. 16, 2018), 36 pgs.

(56) References Cited

OTHER PUBLICATIONS

Other IPEA Related Document (Rule 71.1(b)) filed Feb. 16, 2021, for International Patent Application No. PCT/EP2018/081617 (filed Nov. 16, 2018), 15 pgs.
Amendment filed May 6, 2024, for U.S. Appl. No. 17/294,372, filed May 14, 2021, 6 pgs.

* cited by examiner

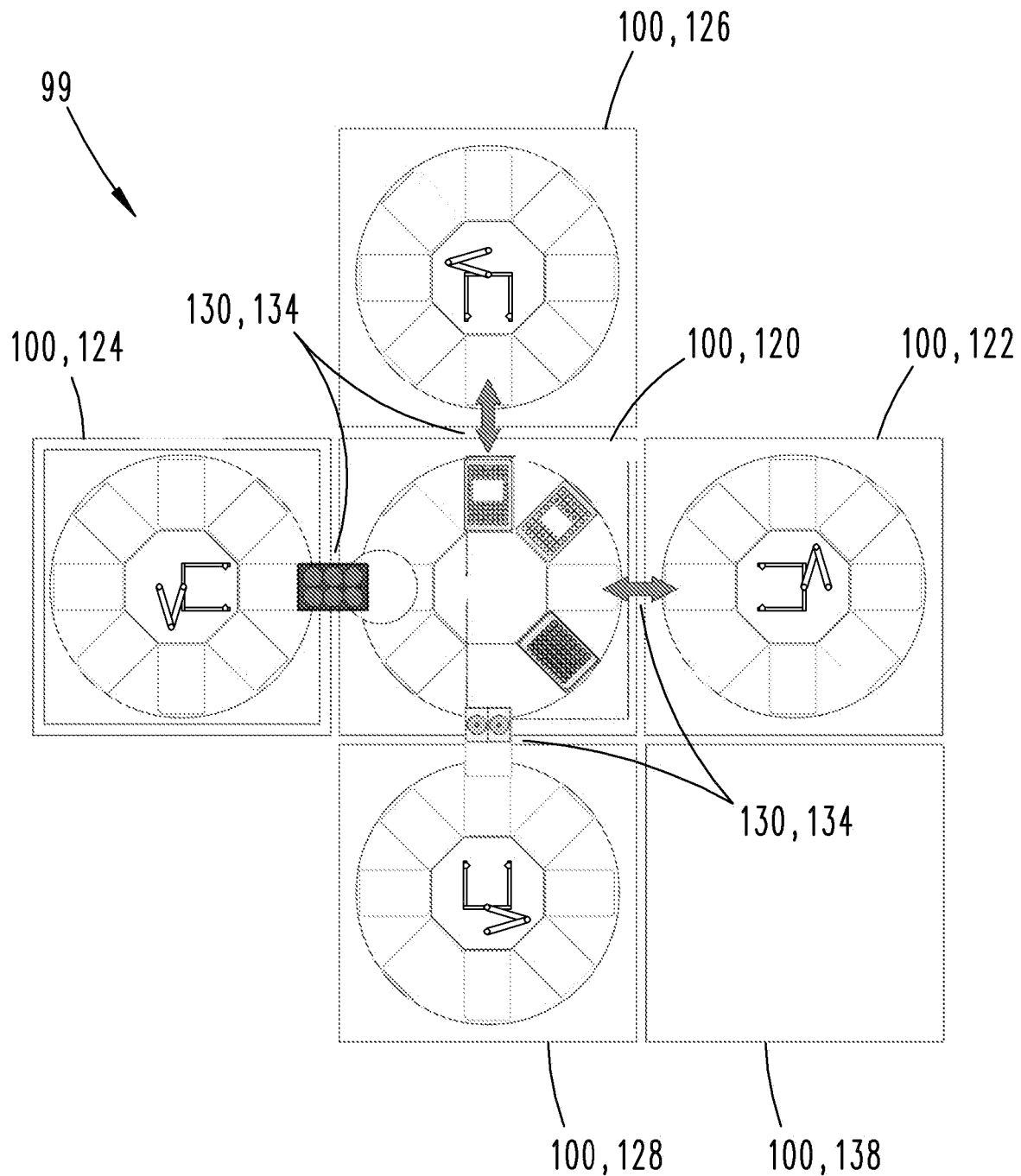

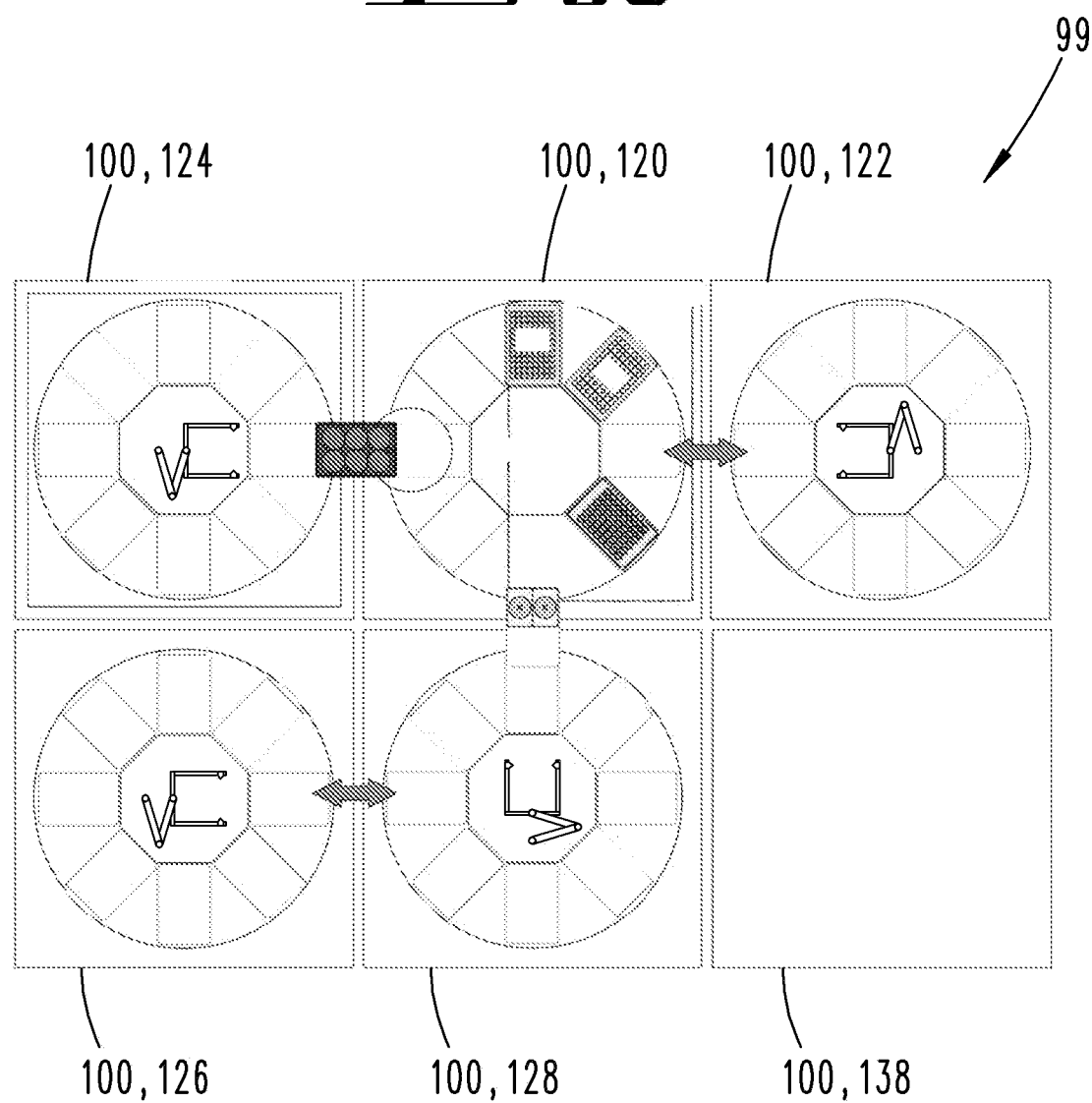

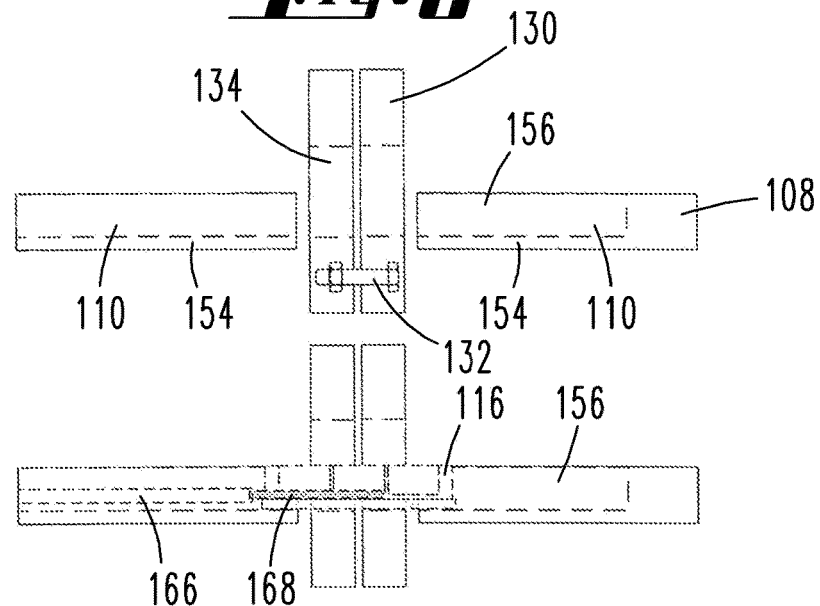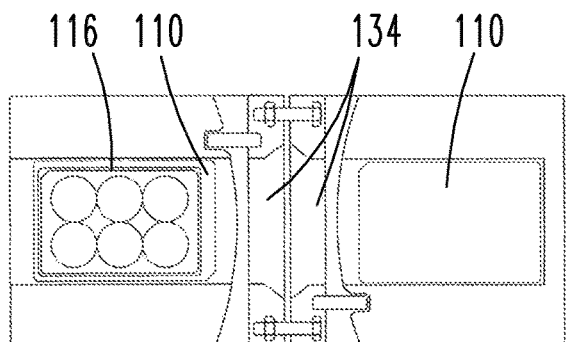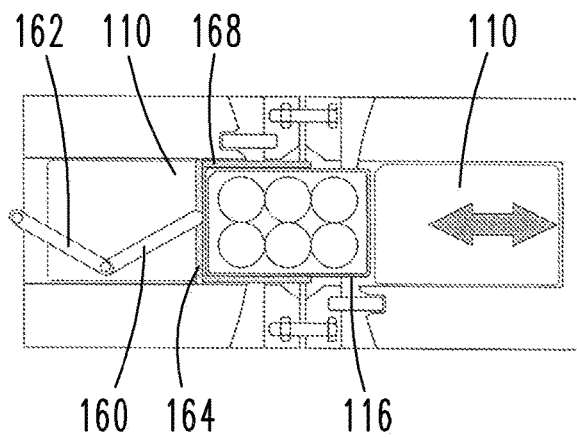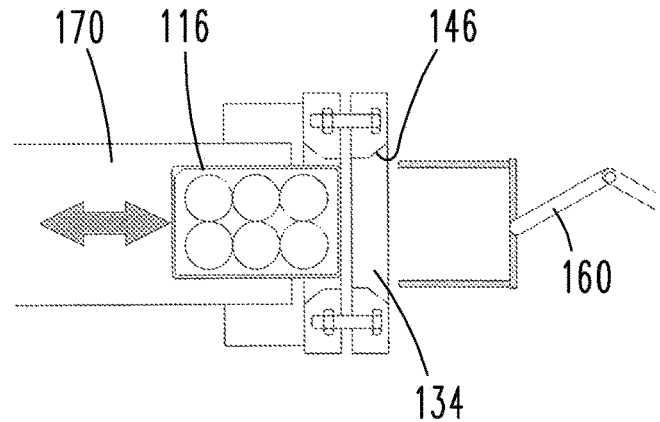

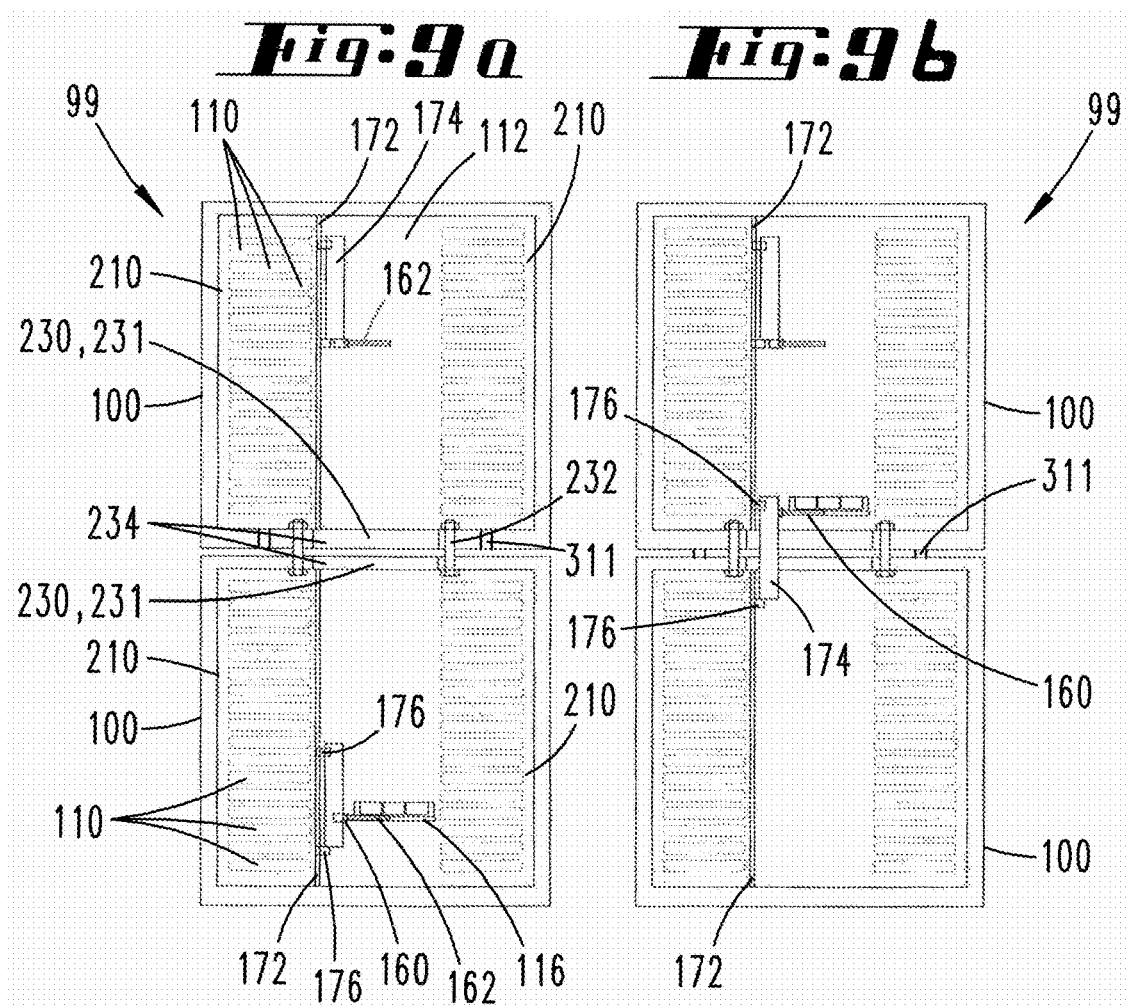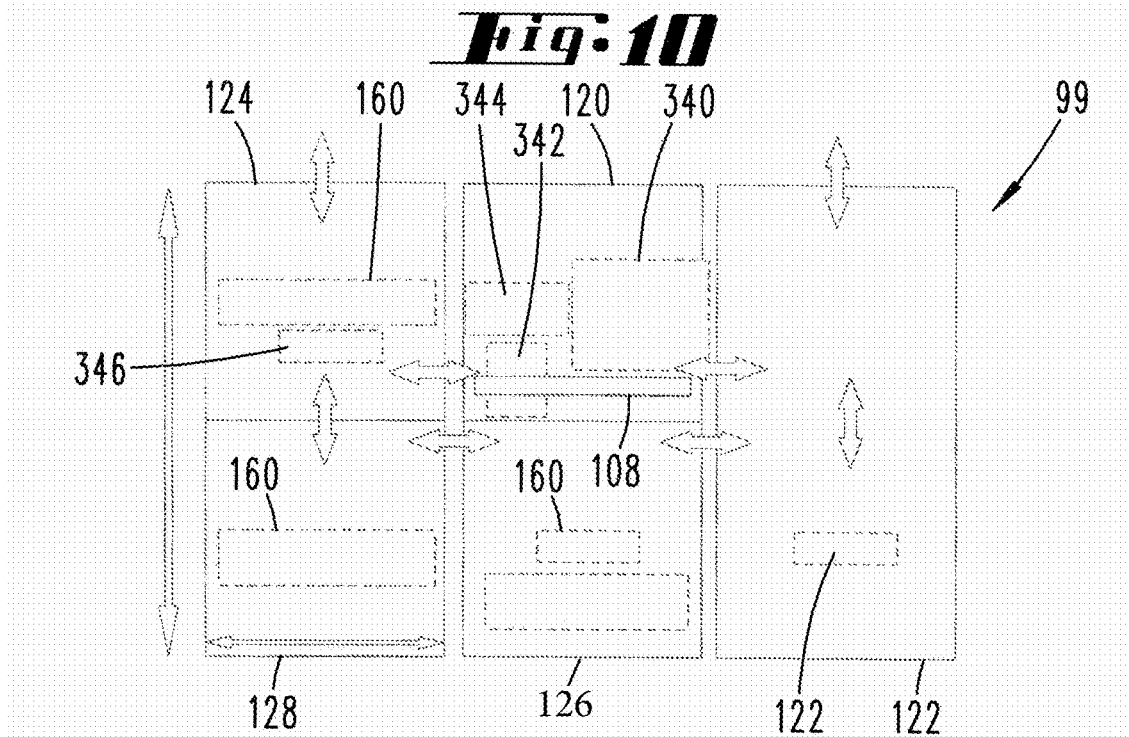

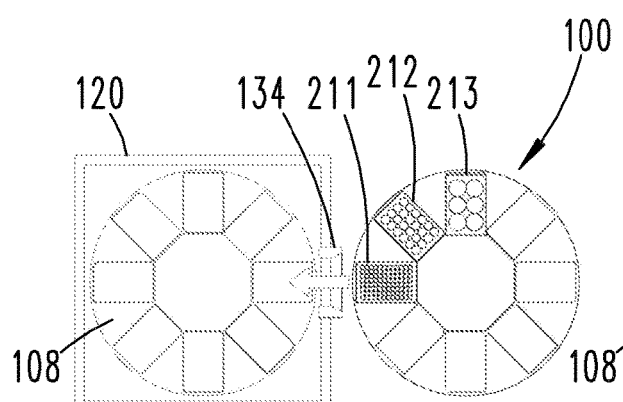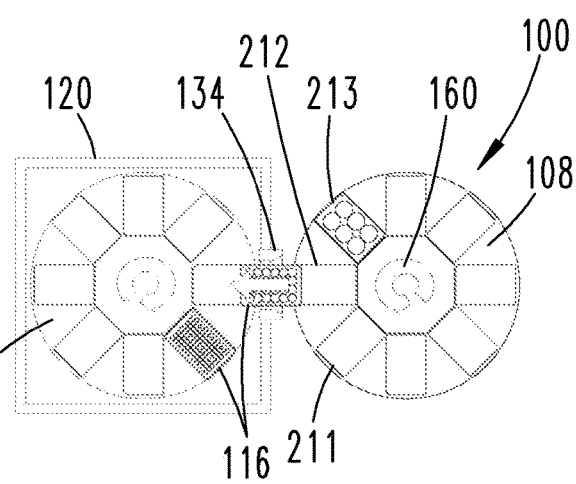

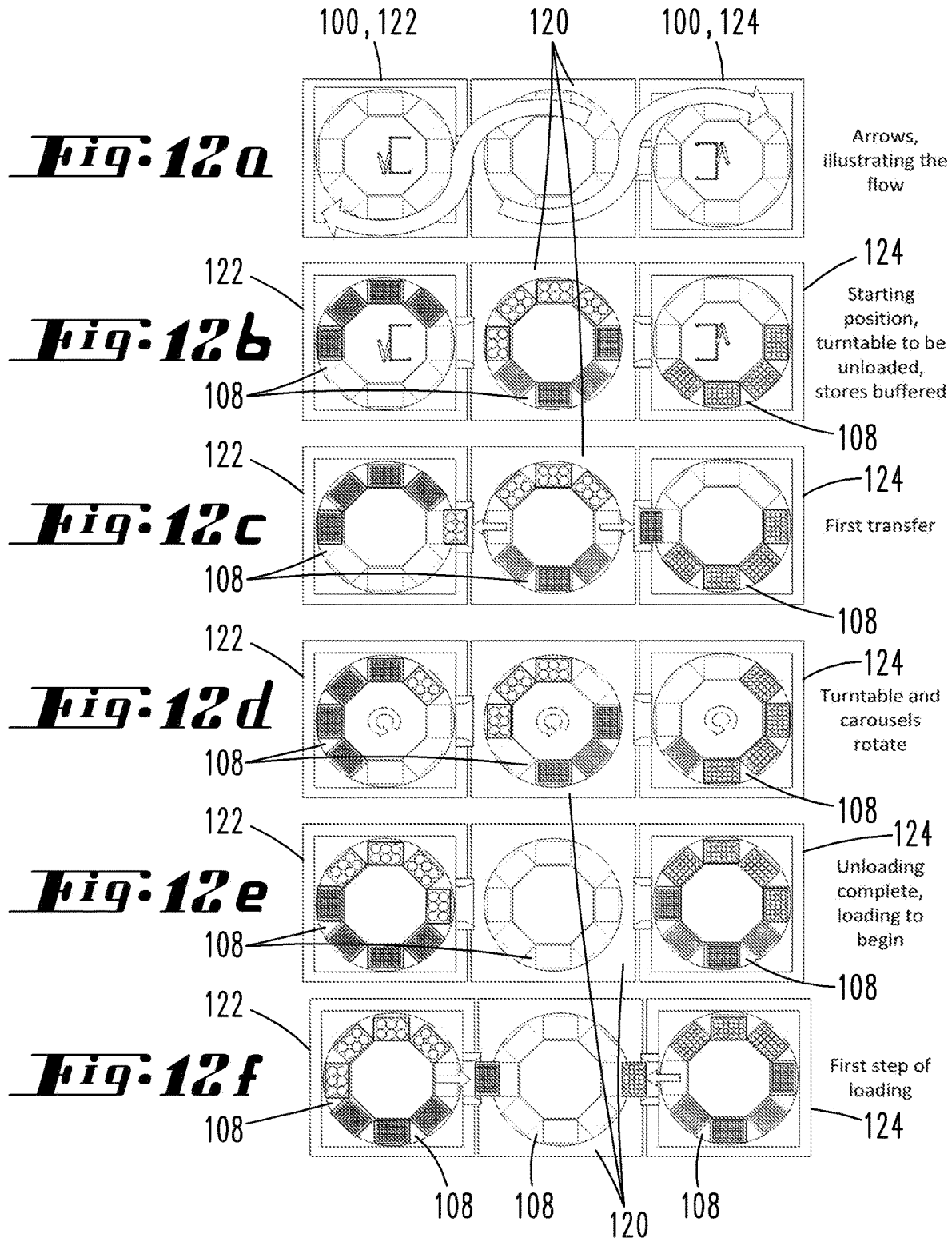

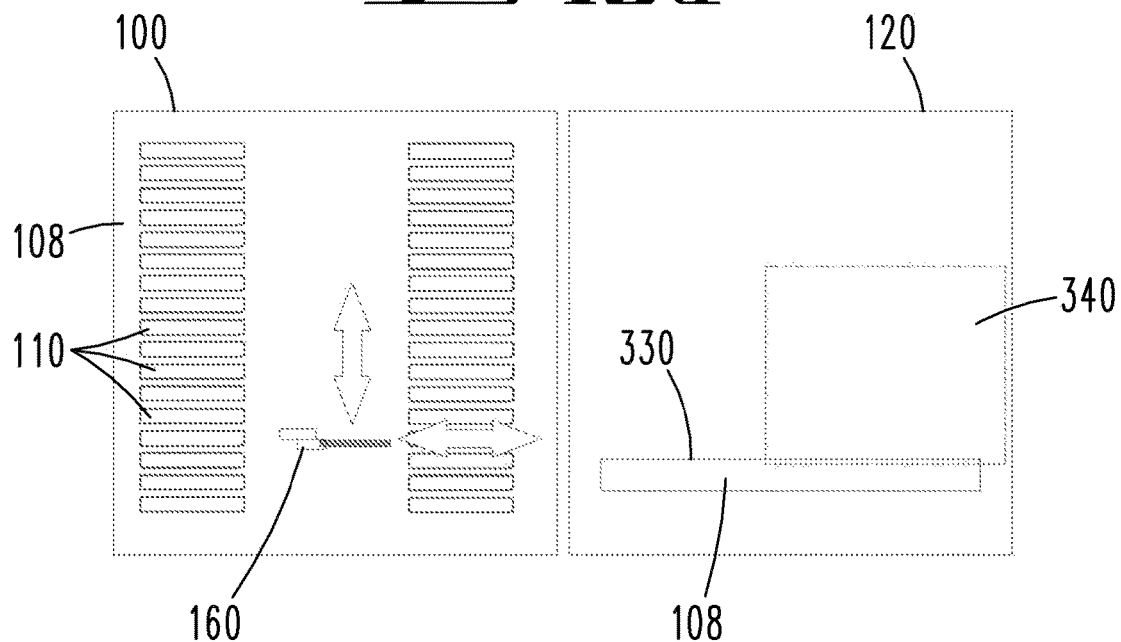
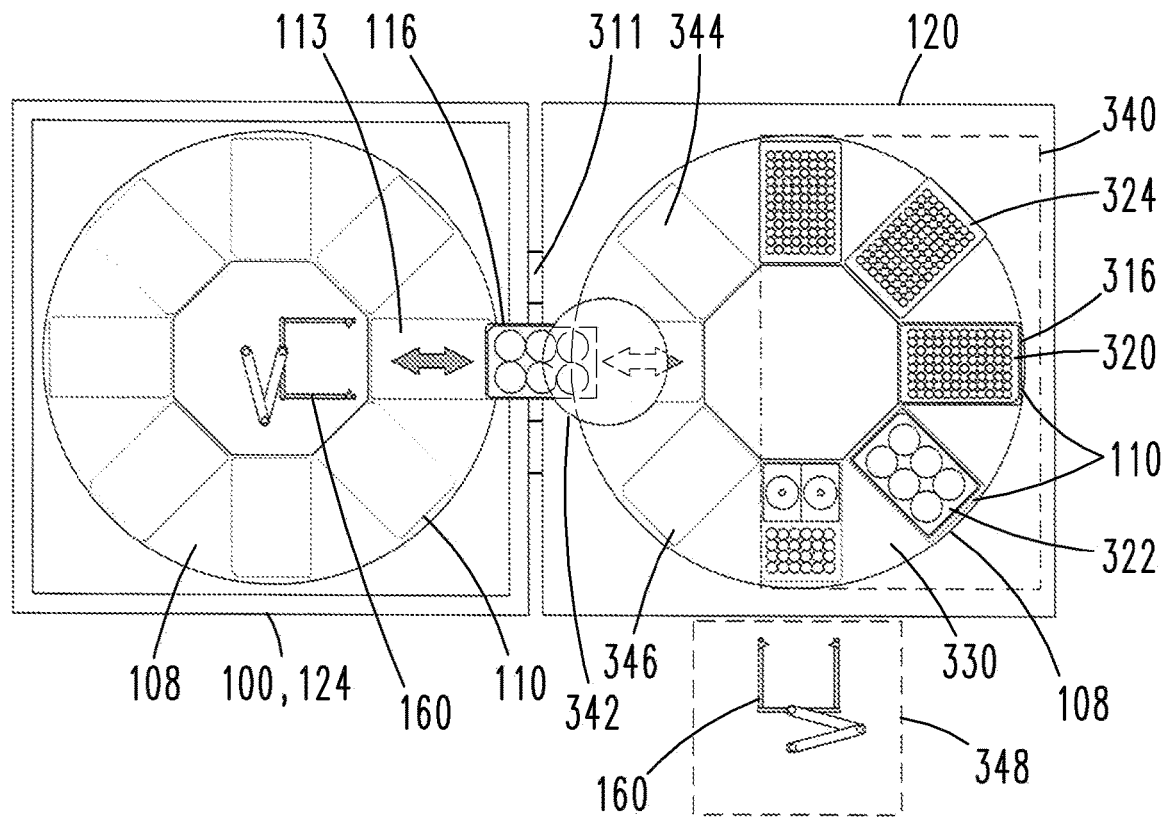

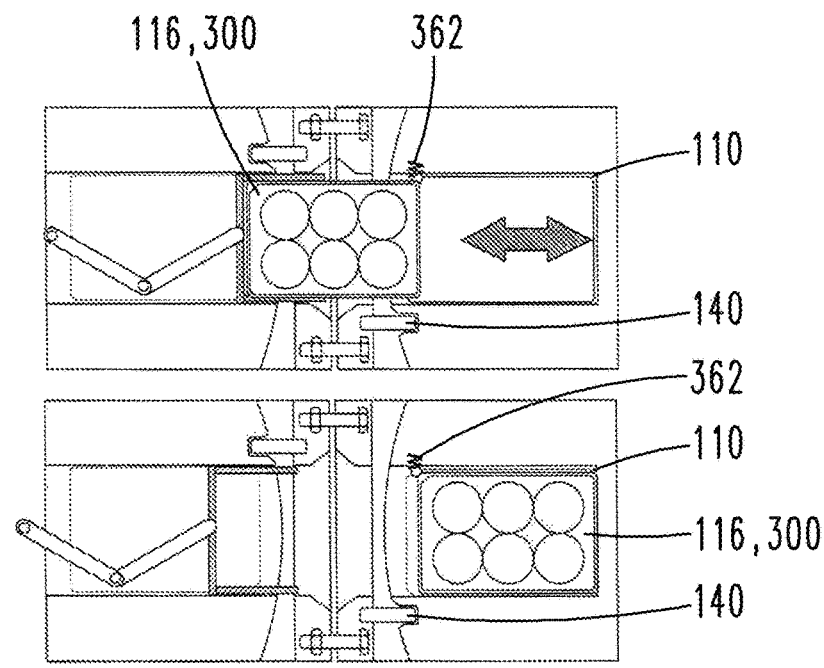
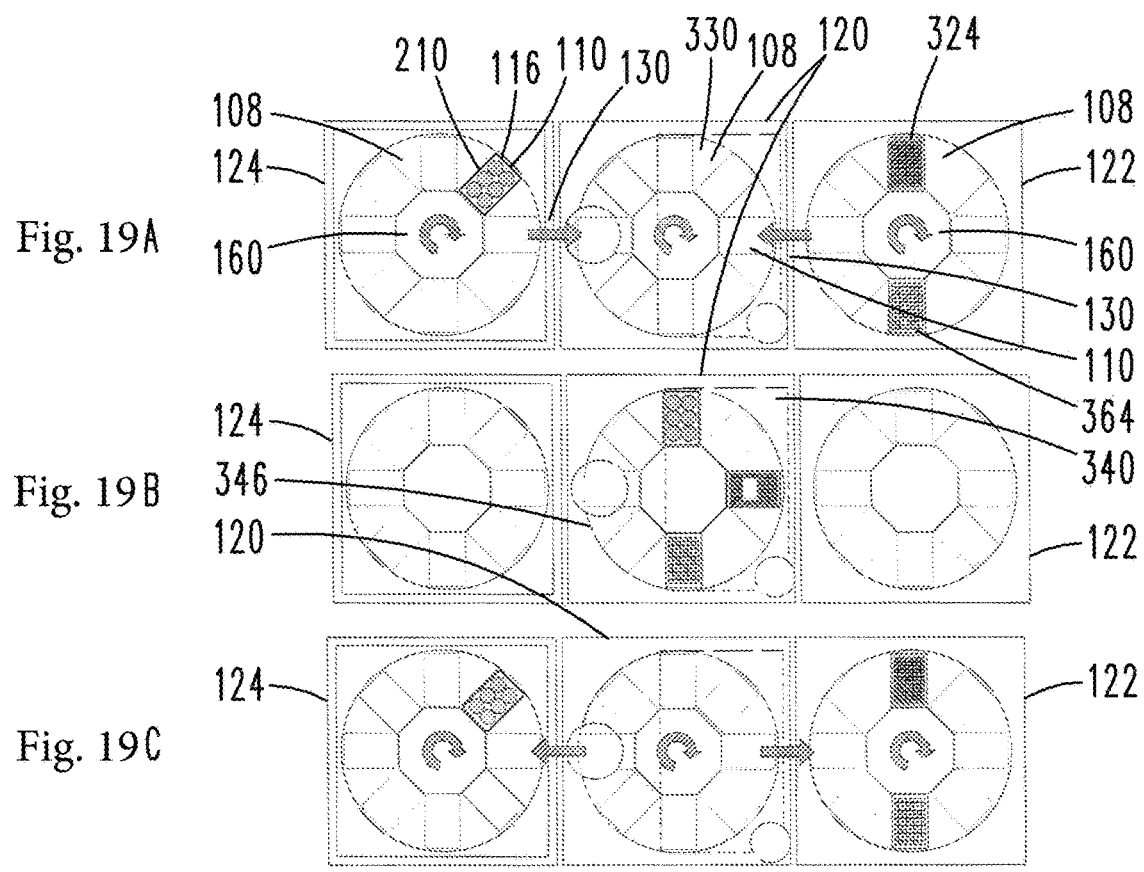

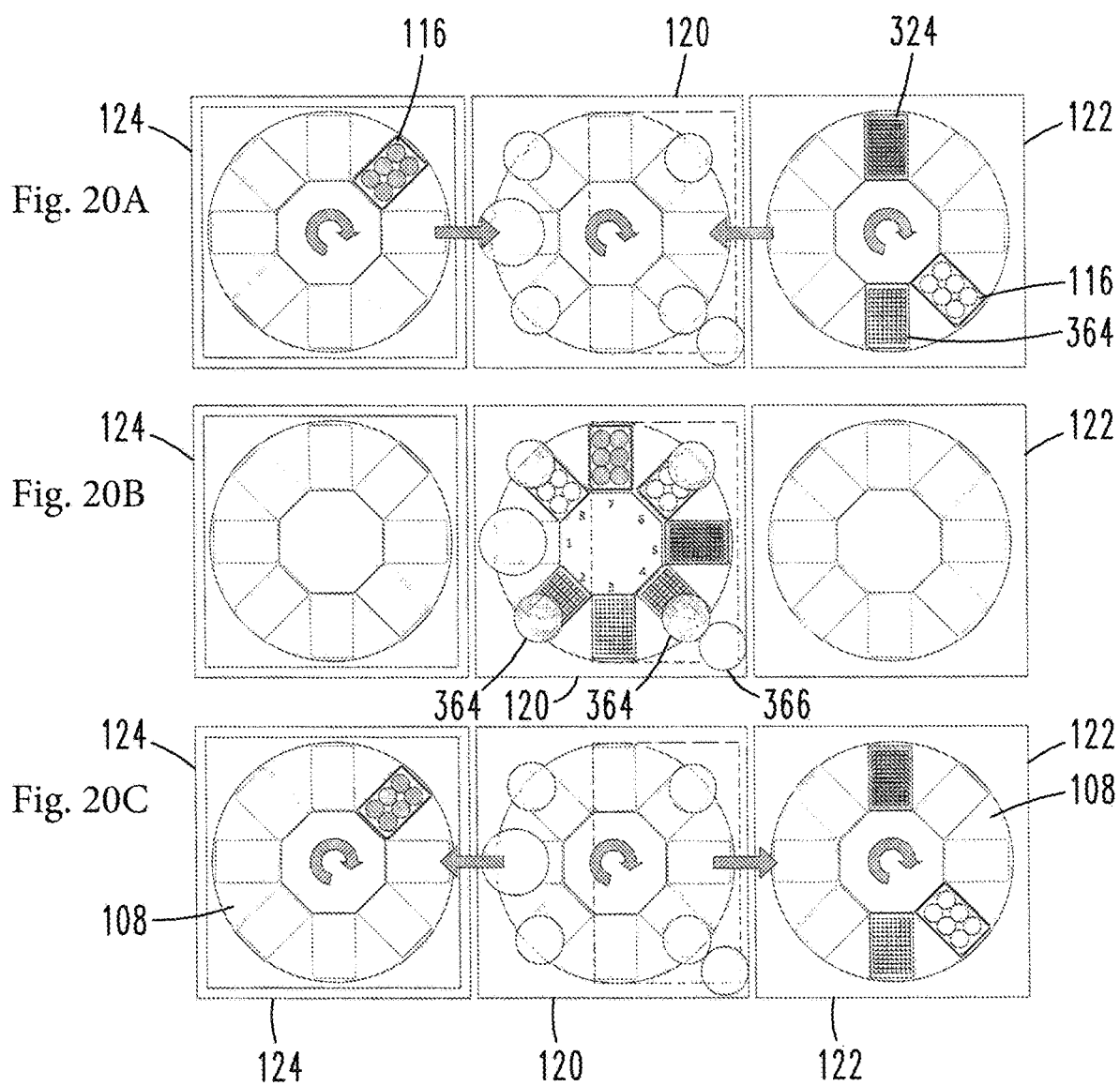

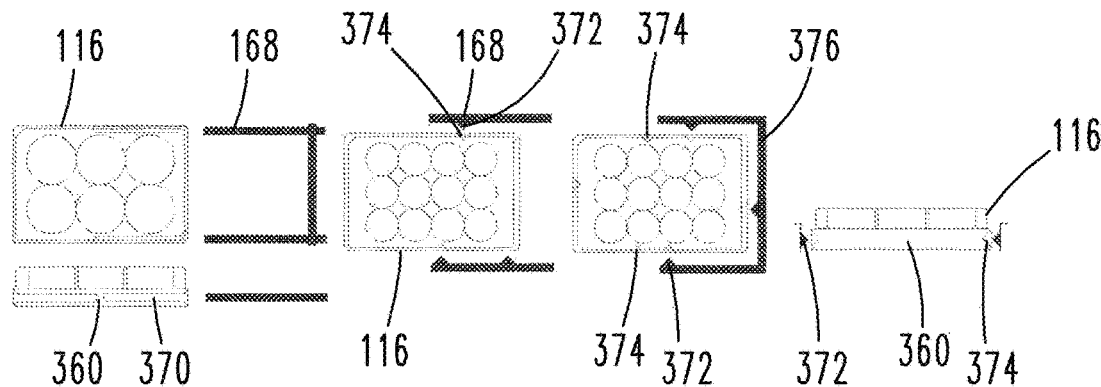
Fig. 21A   Fig. 21B   Fig. 21C   Fig. 21D
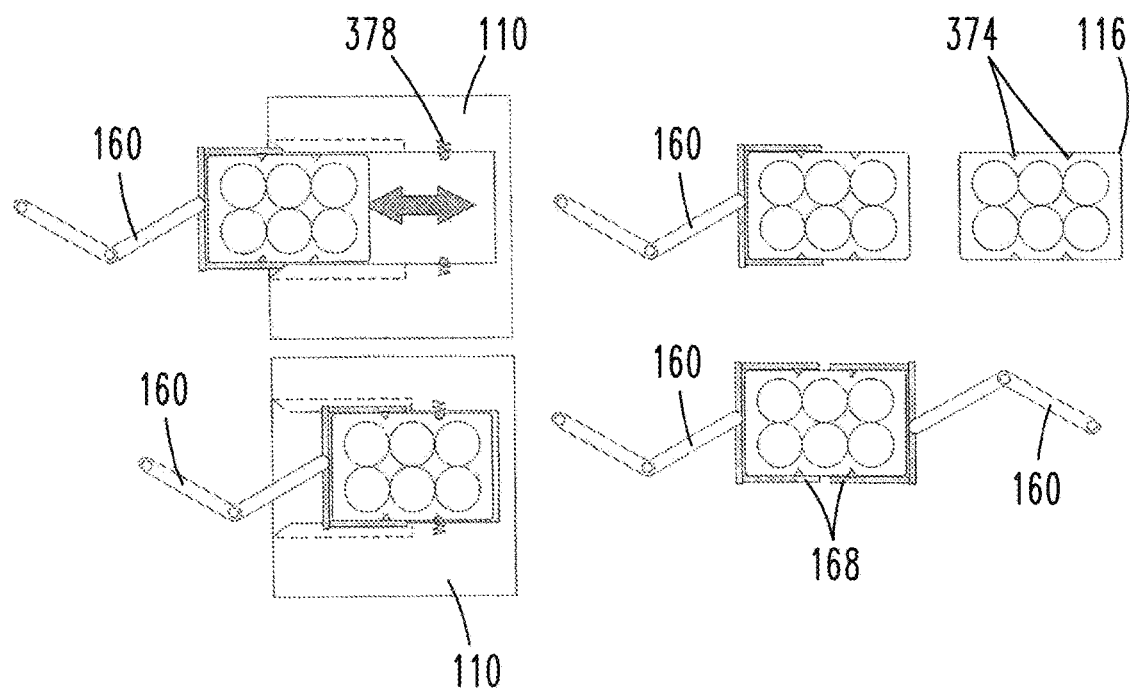
Fig. 22
Fig. 23

PROCESS MODULE FOR AN AUTOMATED BIOLOGY SYSTEM

RELATED APPLICATIONS

This application is a National Stage under 35 USC 371 of and claims priority to International Application No. PCT/EP2018/081641, filed 16 Nov. 2018.

FIELD OF THE INVENTION

The invention relates to a process module for a biology laboratory system, comprising: A housing, a working deck being located within said housing, having a plurality of working deck plate slots for receiving a cell culture plate, a liquid handling robot comprising at least one pipette for aspirating a liquid medium, a first transfer interface being in communication with a first storage module for storing cell culture plates wherein the working deck is movable to a plurality of working positions, in one of the working positions the cell culture plate is located under an operating point of the liquid handling robot, in another of the working positions the cell culture plate is in alignment with said first transfer interface for transfer of the cell culture plate between an outside of the housing and the working deck plate slot.

The invention further relates to a use of a single well plate or a plate in a biology laboratory system for maintaining cell cultures.

BACKGROUND

A process module for an automated biology laboratory system is disclosed in CN 104777321.

A machine for automated filling a plurality of microplates in a biology laboratory system is disclosed in U.S. Pat. No. 6,360,792.

An automatic chemical or biology sample analyzer is disclosed in U.S. Pat. No. 7,670,553.

A transferring device of sample racks for automatic chemical analysis is disclosed in JP-H01 1189561.

US 2016/0145555 A1 shows a system for facilitating biological communication between two or more cell culture devices. A fluid collection device comprises a tip that engages to an output port or an input port of a fluid device. A plurality of fluid devices are stored on a carousel.

US 2018/0044624 A1 shows a cell culture device including an incubator for accommodating a close-system culture container.

U.S. Pat. No. 7,883,887 shows an automatic cell cultivation operator comprising storage devices for storing cell cultures and lab-ware and a three-dimensional movable robotic arm to handle microplates and lab-ware.

US 2016/0201022 A1 discloses an automatic culture system comprising transfer means for transferring microplates for an automatic maintenance.

U.S. Pat. No. 8,652,829 B2 discloses an automated robot system for microcell culture maintenance.

Other microfluidic cell culture systems are known from U.S. Pat. No. 9,388,374 B2, US 2017/0145366 A1 or U.S. Pat. No. 9,057,715.

Cell culture is highly skilled but laborious and tedious, which means the labor cost is high. Furthermore, reproducibility may be low, because the workflows are difficult, complex, and may extend over many weeks. Therefore there have been efforts to automate cell culture.

Cells are cultured in plastic-ware (flasks, round dishes, bottles, multi well plates) in incubators. To passage cells a typical procedure involves: pre warming media, PBS, trypsin (stored in a fridge) and de-frosting any additives, such as foetal bovine serum (FBS), and any special additives (such as growth factors), which are stored in a freezer; getting fresh plastic-ware (fresh plates, serological pipettes, pipette tips); getting cells out of incubator into a flow hood (i.e. sterile conditions, although it is preferred to minimize time out of incubator); checking cells under a microscope; washing cells with PBS; getting cells off with trypsin, suspending, taking an aliquot and counting the cell concentration in a counting slide on a microscope; adding the appropriate amount of cells, and any media; and putting the cells back in the incubator. Many of the liquid transfers are done with serological pipettes, and the smaller volumes are done with micropipettes, with disposable pipette tips.

There are existing systems for automating cell biology. These systems are assembled from a variety of laboratory equipment components (liquid handlers, automated incubators, fridges, etc.), in various formats, from various vendors, that were generally not designed to work together. These are often assembled by bolting the devices on to a table or other machine bed. The devices are then integrated with 3D robotic arms.

SUMMARY OF THE INVENTION

An object of the invention is to provide a processing module for use in a biology laboratory system which can work fully automated for a long time.

A further object of the invention is to amend lab-ware used in a process module.

The present invention provides solutions for the above mentioned problems.

A process module of the invention is characterized in that the first transfer interface or a second transfer interface being in communication with a second storage module for storing lab-ware or liquid material, wherein in another of the working positions a plate comprising lab-ware or liquid material being carried by one of the working deck plate slots is in alignment with said first or second transfer interface for transfer the lab-ware or the liquid material comprising plate between an outside of the housing and the working deck plate slot. The method comprising the following steps: Transfer a cell culture plate from an outside of the housing through the at least one transfer interface to one of the working deck plate slots, transfer a plate carrying lab-ware or liquid material through the at least one transfer interface from an outside of the housing to a different working deck plate slot, moving the working deck into a different position, aspirating liquid medium with the liquid handling robot from the plate carrying liquid medium and/or grasping lab-ware from the plate carrying lab-ware, applying liquid medium to the cell culture plate by using the lab-ware, moving the working deck into a different working, discharging the cell culture plate through the at least one transfer interface. The following features can be realized optionally: There is provided a process module for a biology laboratory system, comprising: a housing; a working deck within the housing, the working deck having at least one plate slot for holding a microplate or lab-ware; a liquid handling robot positioned above the working deck; wherein the working deck is movable, especially rotatable to position the working deck plate slot under an operating point of the liquid handler; wherein the plate slot is alignable with an interface for transfer of a microplate or lab-ware between an outside of the housing and the working deck plate slot in a single horizontal plane. This places the processing of biology system in a single module where the plates or lab-ware can be transferred from a turntable or working deck out of the module once the processing is completed, or onto the working deck when processing is required. Preferably the liquid handling robot is a pipeting robot. This allows the movement of liquids between lab-ware on the working deck and into lab-ware. Preferably the process module further comprises any of the following, a microscope, a capper/de-capper robot or a lidder/de-lidder robot, positioned above the working deck. This provides all the processing in a single module without the processed plates needing to be moved to a different module for inspection or having to move medium to a different module for decapping. This not only reduces the movement requirements of the robots, but also reduces the processing times ensuring that samples do not become spoiled due to delays. Preferably the working deck plate slots are radially arranged with reference to a center axis of rotation of the working deck. This ensures that when the working deck is rotated, the plate slots are always in the same position for each step of rotation. This ensures that the various robots, e.g. a pipetting robot, has a consistent location for different plate slots as the working deck is rotated. Preferably the working deck plate slot is recessed into the surface of the working deck. As with the channels discussed above, the recess will stop the plate or lab-ware placed thereon from rotating or moving on the working deck during processing. Preferably the working deck plate slot comprises an alignment means at an outer edge of the working deck, wherein the alignment means define a width of an entrance to the plate slot that decreases with decreasing distance to the center of the module. This ensures that when plates are delivered to the plate slots that they are readily aligned with no risk of collisions. Preferably the working deck is mechanically indexed to one or more positions for providing a position for operation by the liquid handling robot on the plate slot, or providing a position for aligning the working deck plate slot with the interface. Indexing ensures that when the working deck rotates it stops at a location where the plate slots are aligned with an interface or in a position under or at one of the robotic devices to carry out processing. Preferably the system further comprises a module comprising a rotatable carousel having at least one storage plate slot, wherein the storage plate slot is radially alignable with the interface and working deck plate slot. This allows further modules to feed into and out of the process module. The further modules have plate slots that align with the common interface between the process module and the further module for transfer of lab-ware or plates. Preferably the storage plate slot, interface and working deck plate slot are in the same horizontal plane and wherein transfer of a microplate or lab-ware between the storage plate slot and working deck plate slot is via a single rectilinear motion. This ensures simple robotic movements as no vertical movement is required (or with stacked modules no horizontal movement is required), instead a single movement places the plate in the slot of the process module from the storage module, or vice versa. Preferably the rotatable carousel is housed in an incubator module, fridge module, freezer module or plastic-ware store module. Preferably the working deck is mechanically indexed to one or more positions for providing a position for aligning the working deck plate slot with the interface and the carousel plate slot. In a further embodiment there is provided a method of operating a process module, the method comprising the steps of: rotating a working deck inside the process module to radially align a plate slot with an interface of the process module; rotating a carousel of an adjoining module having a carousel plate slot to radially align the carousel plate slot with the interface, wherein the interface allows the transfer of a microplate or lab-ware to or from the process module to the adjoining module; transferring the contents of the carousel plate slot or plate slot through the interface to the radially aligned plate slot; rotating a working deck inside the module to a position in which a plate slot on the working deck is positioned under a liquid handling device; operating the liquid handling device to interface with the contents of the plate slot; and rotating the working deck to position a further plate slot on the working deck under the liquid handling device. This allows the transfer of lab-ware to the process module from the storage module, the processes of the medium in the lab-ware and the transfer of the lab-ware out of the process module into the storage module. Preferably the transferring of the contents of the carousel plate slot or plate slot is via the linear horizontal motion of a grabber of a robotic handling device located in the adjoining module. Preferably the grabber is constrained to extend in a single horizontal direction from the center of the adjoining module in the direction of the interface, and vertically. In a further embodiment there is provided a module for processing biological material, the module comprising: a pipetting robot; an inspection tool; and a turntable with a first holding slot for holding a process material carrier and a second holding slot for a cell culture carrier; wherein the cell culture carrier is processed on the turntable; and wherein the turntable is rotatable to provide the pipetting robot and inspection tool access to the first holding slot and second holding slot. The turntable greatly facilitates making the process module compact (substantially a cube), with about an 80 $cm^2$ footprint because the turntable is a very compact mechanism for moving plates in and out of the pipetting robot working area. This is also advantageous for putting all or most of the process functions in a single module—this means the system has an integrated process module, surrounded by stores that require less functionality. Preferably the first holding slot and the second holding slot are identically sized. This ensures a uniform system and lab-ware. Preferably the process material is a liquid. Preferably the process material carriers are microplates or lab-ware with the same footprint as a micro plate. The standardized size allows the use of the same plate slots or handling devices for all items within the module and system. Preferably the inspection tool is a microscope. This allows the analysis of cell culture carriers within the module. Therefore it can be determined if a process is completed without having to remove the plate or lab-ware from the module. Preferably the module comprises a sealed housing. Preferably the module comprises a means for circulating filtered air. This ensures that clean air is always present in the module and the flow ensures that that emissions from any of the containers do not affect other containers. Preferably the module comprises interfaces for exchanging microplates or lab-ware with the same footprint as a microplate into and out of the module. The process module or a system comprising the process module can have a controlling unit as a computer comprising soft-ware for operating the process module as disclosed, wherein the handling robot is electrically driven.

The present invention provides a novel use of a single well plate. The single well plate comprises a flat horizontal bottom with a rectangular shape and four vertical walls. The four vertical walls enclose a single well. The single well is a volume for a liquid. This kind of single well plate is used in a biology laboratory system as disclosed above as a reservoir for a liquid medium, which is used for maintaining cell cultures. The liquid is handled by a robot comprising at least one pipette for aspirating the liquid medium and applying said liquid medium to said cell culture, which is stored in a cell culture plate. The sealed storage wells may be sealed in a hermetical or at least fluid tight manner by a film that is attached to or close to a top edge of the well or of the entire plate. The well forms a growth area for biological material of a size of a micro plate.

The present invention is further related to a use of such a plate and similar plates, which have more than one well as a transporting device for trans porting liquid from a supplier to a biology laboratory system and applying said liquid for cell culture maintenance. The top opening of the at least one well is sealed by a foil. Preferably the plate has a foot print of a microplate. Preferably the foil is heat-sealed to the upper edge of the wall. Preferably the sealed top aperture of the at least one well is covered by a lid. The sealed storage wells may be sealed, in a hermetical or at least fluid tight manner by a film that is attached to or close to a top edge of the well or of the entire plate. The film may have a breaking strength or features such as scored features that allows it to be penetrated by a plastic disposable pipette tip.

BRIEF DESCRIPTION OF THE DRAWINGS

These and other features of the present invention will now be described in further detail, purely by way of example, with reference to the accompanying drawings, in which:

FIG. 3A shows a plan view schematic of the modules of FIG. 1 and FIG. 2 formed into a system of a different configuration;

FIG. 3B shows a plan view schematic of a system according to FIG. 3B with a different configuration;

FIG. 6 shows a side view sectional schematic of an interface according to FIG. 4A, 4B and 4C;

FIGS. 7A and 7B show a plan view schematic of a further embodiment of an interface between modules;

FIG. 8 shows a pan view schematic of a further embodiment of an interface between modules;

FIGS. 9A and 9B show a side view sectional schematic of two modules vertically stacked;

FIG. 10 shows a side view schematic of modules vertically and horizontally arranged;

FIGS. 11A and 11B show a plan view schematic of buffer slots between two modules;

FIGS. 12A to 12F show a plan view schematic of the steps of using buffer slots with three modules;

FIG. 15A shows a side view sectional schematic of a store module and a process module;

FIG. 15B shows a plan view schematic of the store module and process module of FIG. 15A;

FIG. 18 shows a plan view schematic of an interface between modules with a detection means;

FIGS. 19A-19C and 20A-20C show a plan view schematic of plate transfer steps between modules;

FIGS. 21A-21D show a plan and side schematics of a handling device and a plate according to an embodiment;

FIGS. 22 and 23 show plan view schematics of the handling device of FIGS. 21A-21D and plate slots and additional handling devices;

DETAILED DESCRIPTION

Figure 1:
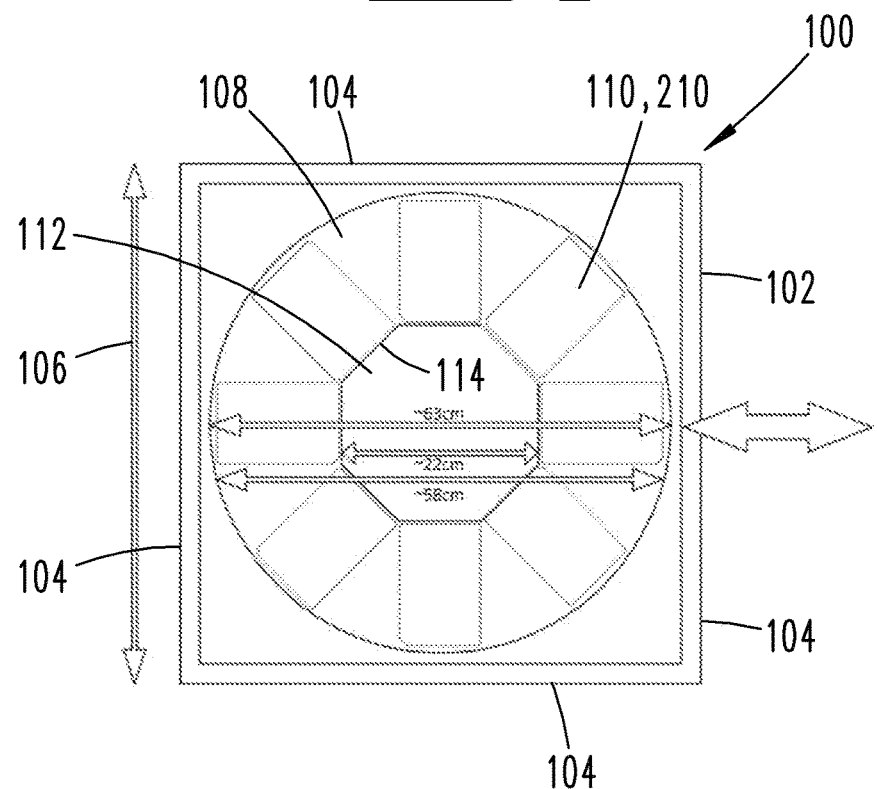
FIG. 1 shows a plan view schematic of an embodiment of a module.

Referring to FIGS. 15A and 15B, there is shown a process module 120 connected to a further module 100, which may be any of the modules described herein.

The process module 120 has a rotating element 108 or 'turntable'. However, in the process module 120, the turntable 108 can be a single surface and not have various vertical racks 210. Instead the top surface of the turntable 108 forms a working deck 330 or at least part of a working deck 330. The turntable working deck has a number of slots for lab-ware, and can be aligned to functional modules (e.g. the liquid handling robot) in the process module, and to an interface where plates are transferred horizontally onto the turntable working deck from another module. The turntable working deck thus functions as a very compact, unified and simple means for transporting plates into the module, and between multiple functional elements.

In the process module 120, there is provided a liquid handler robot 340. The liquid handler 340 is positioned above the turntable 108. In the illustrated embodiment, the liquid handler 340 does not occupy the whole area above the working deck 330 as can be seen in FIGS. 15A and 15B. As shown in FIG. 15B, the turntable 108 is rotated so that five plate slots 110 are positioned under the liquid handler 340. The liquid handler can be configured to have liquid dispensing points at each of the plate slots 110 arranged underneath it, or a select number as required. The actual size of the liquid handler can vary depending on the function required of the system 99. In some embodiments, it is positioned to access all the plate slots 110 in the working deck 330.

As previously discussed, the turntable 108 and thus the rotating working deck 330 in the process module 120 has radially arranged plate slots 110 that can hold various articles, such as cell culture plates 116, or plates carrying consumables such as pipette tips and media bottles. In FIG. 15B, there are eight radially arranged plate slots 110. In a conventional cell culture system eight slots may be sufficient, however, the total number of plate slots 110 can vary depending on the requirements, for instance, the plate slots 110 could be adapted to hold more than one plate adjacent to one another.

FIG. 15B shows a microscope located at a plate slot 110 in the process module 120 so that the turntable 108 can be rotated into it. The microscope would have a lens below the plate (because it would observe the cells through the bottom of the plate), and a light source, such as a high-powered LED array, e.g. above the plate. Any position in the working deck 330 where it was desired to scan the plates 116 with the microscope 342 would therefore have to have a cut-out, exposing the bottom of the plate 116 to the microscope lens. Alternatively, a plate could be lifted off the rotating working deck with a handling means, and transferred to the microscope. The microscope would move or scan in x & y, so as to be able to observe or scan the whole plate 116. The turntable 108 can be indexed to the microscope 342 such that the microscope 342 always remains in the same position to ensure high quality inspection of the plates or contents below. In the figure shown, the microscope 342 is located on the position that plates 116 are transferred to and from an incubator 124. This allows plates 116 to be transferred to and from the plate slot 110 below the microscope 342, without turning the turntable 108 of the process module 120. Other processes occurring on the turntable working deck 330 are consequently not disrupted. Other embodiments are possible, e.g. the microscope 342 might be positioned on another slot on the working deck 330.

The microscope 342 is commonly used for monitoring the state of the cells (e.g. confluency), so as to know the growth rate of the cells, and when they need to be passaged next, or where there are enough cells for another process to start. In one embodiment, the microscope 342 is further able to detect the pH of the medium (which carries a dye that acts as a pH indicator), and/or to detect gross microbial contamination (which will make the medium acidic (more yellow) and cloudy).

In an alternative embodiment the microscope 342 is indexed to the turn table 108, or the microscope 342 is positioned to see an area greater than that of the plate 116 or plate slot 110 required, and be programmed to ignore the features outside of this view, or use these to compensate for a mis-positioning in the plate 116.

An optional decapper robot 344 is shown and provided in a position above a plate slot 110 when the turntable 108 is rotated to the relevant position. The decapper 344 de-caps vials 321 and bottles 323. Vials 321 and bottles 323 that needed to be de-capped have their plate slot 110 rotated to the de-capping position under the decapper 344 via the turntable 108. The turntable 108 can then rotate the de-capped plate slot 110 to the position where they would be required for the liquid handling 340 (e.g. a pipetting robot).

An optional de-lidding station 346 is also shown and is provided for de-lidding plates 116, e.g. cell culture plates. In the art, consumables such as pipette tip boxes or pipette tip stacks, or plates, including microplate reservoirs, are stored on the deck of a liquid handler. In the system described herein, it is desired to provide the process module with random access to a large range of consumables, similar to what a human would have access to in a lab. To this end, the process module is interfaced to an automated incubator, an automated fridge, and an automated plastic-ware store, so that consumables or cell culture plates can flexibly be shuttled to and from the process module as required. In order to enable this, it is desirable for the system to be able to lid and de-lid e.g. pipette tip boxes and microplate reservoirs. In the art, pipette tip boxes have lids adapted for human use—they are hinged to the box, and are somewhat compliant, being commonly made of a polymer such as polypropylene. Micro plate reservoirs, if they have lids, also have somewhat compliant polymer lids. The de-lidder may also de-lid pipette tip boxes and other lab-ware, such as microplate reservoirs, so long as they are provided with lids that can be handled by the de-lidder. Such lids are known in the art for cell culture plates, and are generally required to be rigid, being made of a material such as polycarbonate. The lids may further advantageously be glossy, as is known in the art. The de-lidder 346 can be positioned over one of the plate slots 110 carrying a plate on which a lid needs to be removed by rotating the turntable 108.

Therefore, as is shown in FIG. 15B, an example process module 120 could be configured to have one microscope 342, one de-lidder 346 and one decapper 344, all disposed on the working deck 330. Other configurations are possible depending on the requirements of the system. For instance, more than one microscope 342 might be required or a configuration may not require a decapper 344.

In an example, the working deck 330 holds a cell culture plate 116 in a plate slot 110, a rack with vials 320 (e.g., vials containing reagents, or growth factors) and bottles 322 (e.g., bottles containing cell culture medium, or trypsin), pipette tip boxes 324, and with two different sizes of pipette tips. The working deck 330 may be stationary while the liquid handler 340 carries out liquid transfers, or it may rotate to conveniently present various plates or other consumables, at various times, to the liquid handler 340. There might additionally be additional articles, such as a second cell culture plate 116, in the positions under the microscope 342, de-lidder 346 or de-capper 344. Given that the mechanisms for the microscope 342, de-lidder 346 and de-capper 344 are positioned above the plate slots 110 on the working deck 330, in most cases this would prevent the liquid handler 340 from reaching articles in those plate slots 110. Articles in plate slots 110 under the microscope 342, de-lidder 346 or de-capper 344 can be exposed to the liquid handler 340 when required by rotating the working deck 330.

With eight radially arranged plate slots 110 for cell culture plates 116 with an SLAS (Society for Laboratory Automation and Screening) microplate footprint, the turntable 108 for the working deck 330 can be small, e.g. less than 80 cm in diameter. This allows the process module 120, or other modules 100 with similarly sized turntables 108 to be compact and easy to fit through doors, such as doors of a laboratory cleanroom. This makes installation of the system 99 generally convenient, fast and economical, since the modules can be built in a factory, then assembled together on-site.

A carousel 108 with a racking system 210, such as the carousel 108 of an incubator 124 shown in FIG. 15B, can be arranged to be in close proximity to the working deck 330 of the process module 120, so that lab-ware 300, such as cell culture plates 116, may be transferred from a plate slot 110 in the incubator 124 carousel 108 to a plate slot 110 on the working deck 330, by a simple horizontal movement. A robotic device 160 for transferring a plate 116 can be provided in the incubator 124.

An external solid waste receptacle 348, with a robotic grabber 160 is provided in communication with the process module 120. Solid waste from the process module 120 (e.g., used cell culture plates, empty pipette tip boxes, empty bottles) can be transferred to solid waste 348. The solid waste 348 does not need to be modular sized as this can have a smaller capacity and its contents will likely need to be emptied into bags and carried out of the laboratory. A sealing means 311 formed by a piece of pipe connects the modules 100, 120 with an air-tight connection. The sealing means 311 can be used for firmly connecting the two modules 100, 120 together.

Figure 16:
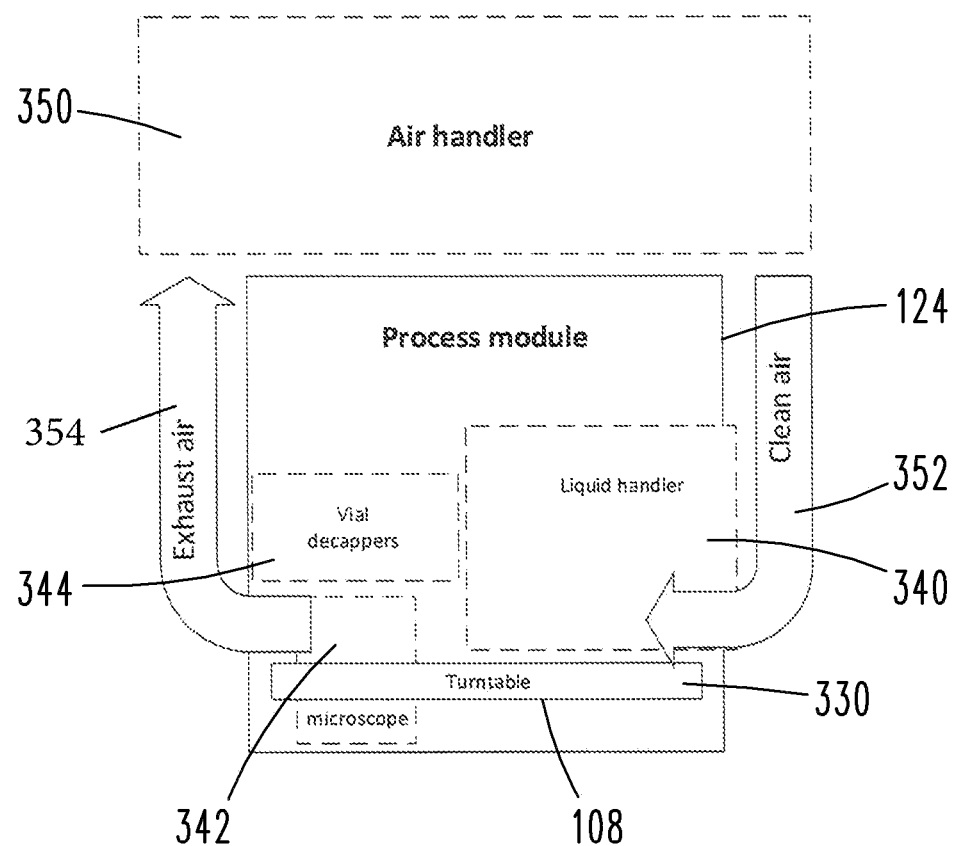
FIG. 16 shows a side view schematic of a process module and air handler.

FIG. 16 provides a schematic of the air flow through a process module 124. An air handler 350 is provided. This is positioned above the process module 124 to save floor space. However, an air handle 350 could be situated in other positions as is appropriate given the system 99. The air handler provides clean air 352 to the process module 124 where the clean air 352 is delivered across (i.e. horizontal to) the process module 124 to an exhaust where exhaust air 354 is delivered back to the air handler 350.

Preferably, HEPA filtered air is blown through the process module 124. As the air is blown horizontally, this can help minimize particles falling into open cell culture plates 116, or reagent vials or bottles. HEPA air might be recirculated through the system 99, via a HEPA filter, as a way of driving down particulates, and reducing exhaust from the system 99. Recirculation of air might be favored during handling steps where it was preferred not to exhaust air to the room, e.g. when for systems handling lentivirus. In some systems, it may be preferred not to recirculate the air.

In one embodiment, the process module 124 further has some means of periodic sterilization, such as hydrogen peroxide vapor, ozone, ethylene oxide, or UV lights, such as UV LEDs, positioned to irradiate the relevant surfaces.

Figure 17:
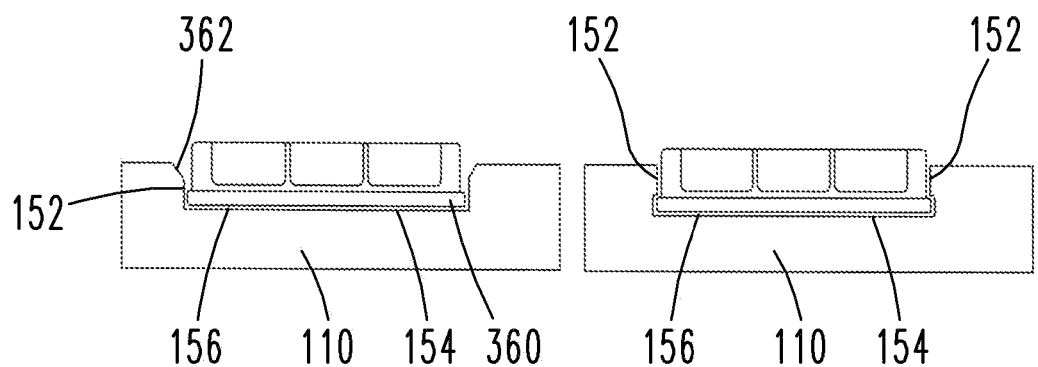
FIG. 17 shows a side view schematic of a plate and a plate slot.

FIG. 17 shows two versions of a plate slot 110. In one version, the plate 116 or other lab-ware 300 sits in a channel 156 or trough, the channel 156 being formed by slot sides 152 and a base 154 where the slot sides 152 are generally vertical. As discussed previously, the plates 116 or other lab-ware 300 has a footprint 360 that is wider than the width of the plate 116 or lab-ware 300 itself. This can be used to enable grabbers 164 to slide into troughs 156. However, in the right hand side plate slot 110 of FIG. 17, a channel 156 is shown where the side slots 152 have a wider portion at the base of the channel 156 and a narrow portion at the mouth of the channel 156. The width of the troughs in this situation is such that the footprint 360 is wider than the narrower portion (but can fit between the wider portion) wherein the plate 116 is vertically constrained within the plate slot 110. This enables alignment of the lab-ware 300 and stops lab-ware from being easily dropped and thus lost.

Such a configuration can be used in particular places, for example on the working deck 330 of the process module 120. This requires either additional grooves in the wall of the channel (e.g. FIG. 5) or grooves 370 (FIG. 21A) in the lab-ware to accommodate gripper fingers, or a robot handling device 160 is required where the grabber 164 and thus gripper fingers 168 do not extend down the sides of a plate 116 in a slot 110. This can be achieved by a gripper that handles a front of a plate 116 or where a plate 116 is pushed in and out of a plate slot 110.

Chamfers 362 are provided on a top edge of the side slots 152 at the mouth of channel 156. These chamfers 362 can assist with aligning a plate 116 that is placed into a plate slot 110 from a vertical position. The above features such as the chamfers 362 and side slots 152 providing varying widths for the channel 156 can be combined with those of FIG. 5, such as the side grooves 166.

Referring to FIG. 18, an engaging means 362 is provided on an edge of a plate slot 110. The engaging means 362 is an element that withdrawably extends into slot 110 to contact a plate 116 or other lab-ware 300 when placed into the plate slot 110. The engaging means 362 is actuated or otherwise triggered by the placement of a plate 116 to indicate that a plate 116 is present in the slot 110. In one embodiment, the engaging means 362 is a spring that becomes recessed into a wall of the plate slot 110 when a plate 116 is present. This in turn activates a proximity or pressure switch, giving an indication to a control system that the plate is present or properly located in the plate slot 110.

Alternatively, the engagement means 362 could be a recess, a press-fit, or a spring, which engages the lab-ware 300. The engagement means 362 can provide feedback (e.g., read by the motor driving the gripper 164), when the means 362 is initially engaged by the lab-ware 300, and further feedback when the lab-ware 300 is fully engaged in the plate slot 110. Such a graduation in signals depending on the location of the plate 116 in the slot 110 can be done by various means such as impedance strips or by proximity sensors placed on the front and back edges of a plate 116 that are trigged by contact with the engagement means 362. Alternatively, a variance in the shape of the plate 116 from the front edge to the back edge can result in a different force being exerted on the engagement means 362. For instance, the plate can be narrower at the front and therefore the engagement means 362 is depressed less than a wider area of the plate 116 that provides a larger depression of the engagement means 362. This would require a consistent alignment of the plate 116 and therefore corresponding engagement means 362 can be provided at the mouth to the plate slot 110.

A sample process is described with reference to FIGS. 19A-19C. Here the changing of the nutrient medium in a cell culture plate 116 is described.

While the cells are growing, the cell culture plate 116, with nutrient medium, is in the incubator 124. The medium needs to be changed, e.g., due to waste products having built up, or nutrient becoming depleted. In FIG. 19A, the plate 116 is transferred onto the working deck 330, along with pipette tips 324, and fresh medium (which may be in a deep well plate 364, or alternatively in a bottle in an adaptor rack, or in a bottle with a microplate footprint). The relevant plate 116, with cells, is retrieved from a plate slot 110 in a plate hotel/rack 210 within the carousel 108 by the robotic device 160. The robotic device 160 travels vertically, and the carousel rotates 108, to present the correct plate 116 to the robotic device 160, which removes the plate 116 from the plate slot 110. The robotic device 160 then travels vertically, to align with the door 130 of the incubator 324 that is aligned with a slot of the rotating working deck 330. The carousel 108/rotating working deck 330 rotates, to align the rotating deck 330 target plate 110 slot (i.e., where the plate 116 is going to be transferred to) with the door 130 of the incubator 124, and the robotic device 160 transfers the plate 116 horizontally into the target plate slot 110 on the rotating working deck 330. The plate 116 is de-lidded, e.g., by rotating the rotating working deck 330 until it aligns with a de-lidding station 346. The aligned de-lidding station 346 then removes and stores the lids.

Pipette tips 324, and cell culture medium (in a deep well plate 364) is transferred from another store 122 into target plate slots 110 on the rotating working deck 330, in a similar way, by vertical travel of a robotic device 160, rotations of the carousel 108, and aligning the relevant target plate slots 110 on the working deck 330 with the door 130 of the relevant store 122. In FIG. 19B, all the required materials, i.e. the plates 116 and medium and tips are in the process module 120.

The liquid handling robot 340 picks up fresh disposable sterile pipette tips 324. Disposable pipette tips are used to avoid contaminating either the medium or the cells, either with microbes, or extraneous chemicals from a previous pipetting step. The liquid handler 340 aspirates spent medium from the plate, and discards it to waste. The pipette tips 324 are then discarded, and fresh pipette tips 324 are picked up. The liquid handler 340 then aspirates fresh medium from the reservoir (e.g. the deep well plate), and dispenses the medium into the plate with the cells. The plate may be a single well plate, or a multi-well plate, in which case the pipette dispenses into the rows of columns of wells repeating the operation until all the wells have been filled with fresh medium. The plate 116, with fresh medium, is re-lidded: the rotating working deck 330 is rotated until the plate 116 is aligned with the de-lidder 346 which is storing the lid which was removed from that plate 116, and the de-lidder 346 re-lids the plate 116, which is then returned to the incubator 124. If they are not required any more, the medium and the pipette tips are returned to storage 122.

FIG. 19C shows the plate 116 and pipette tips 324 and deep well plate 364 back in the original positions in the system 99.

A further illustrative sample process is described with reference to FIGS. 20A-20C. Cells are typically passaged when they are at e.g. 80% confluency. In this example process, the following is transferred onto the rotating working deck 330:
1. the plate 116 with the cells, which will typically be approaching confluency
2. a box of 1 mL pipette tips 324. The tips may preferably be wide-bore tips.
3. a deep well plate 364 containing PBS (Phosphate Buffered Saline) plus EDTA (or an equivalent reagent)
4. a deep well plate 364 containing trypsin (or an equivalent reagent)
5. a deep well plate 364 containing fresh medium
6. two fresh plates 116, which the cells will be transferred to.

An initial position of the materials is shown in FIG. 20A. The liquid may optionally be pre-warmed by transferring the plates 116 to the incubator 124 for a suitable period of time. This may be accomplished by transferring the plates 116 from the store 122 onto the rotating working deck 330, as has been described, then transferring from the rotating working deck 330 into the incubator 124.

In FIG. 20B, once the required materials are on the rotating working deck 330, and the relevant plates 116 have been de-lidded, the liquid handling head 340 picks up fresh pipette tips 324, and aspirates the old medium from the plate 116 that is going to be passaged. The medium is discarded to a liquid waste 366.

Residual medium (including serum), is then washed away. The liquid handler 340 picks up fresh pipette tips, and aspirates PBS, and pipettes it into wells on the plate 116. The PBS is then removed and discarded. This rinse may be repeated to further reduce the residual amount of medium or serum.

Next, trypsin is added. It will be noted that, in FIG. 20B, a number of plates are under the diagonally orientated de-lidding devices 346. The de-lidding devices 346 are not fixed to the rotating working deck 330, so that when the deck rotates, the decappers 344 and de-lidders 346 remain fixed in position. In addition, the diagonally oriented positions can be inconvenient for the pipetting head. Therefore, in this example, the rotating working deck 330 can be rotated so as to present plates 116 in convenient orientations or positions.

The liquid handler 340 picks up fresh pipette tips, then the working deck 330 is rotated, so that the liquid handler 340 aspirates the required (typically minimal) amount of trypsin to the relevant plate (the working deck 330 is again rotated so that the plate 116 with the cells is back in a position that is conveniently oriented for the pipetting head to pipette into), and adds the trypsin to wells in the plate. The plate is then incubated for a few minutes, while the trypsin detaches the cells. In some methods, the plate is incubated at room temperature, which may be accomplished by leaving it on the rotating working deck 330. In other methods, the plate is incubated at 37° C. while the cells are being detached—this can be accomplished by transferring the plate back to the incubator 124. Various methods can be used for choosing the incubation time with trypsin, e.g., the incubation time may be predicted based on past results with a given cell line. Alternatively, automated microscopy may be used to monitor the detachment of the cells.

Once the cells are sufficiently detached, the liquid handler 340 adds medium (with the required rotations of the working deck 330, as described above for trypsin), typically with serum, to quench the trypsin. Alternatively, there are modified trypsins, or similar reagents, known in the art, that do not require quenching with serum. The liquid handler picks up fresh pipette tips, aspirates the required amount of medium, and pipettes it into the wells containing the detached cells. The detached cells are re-suspended, e.g., by gently pipetting up and down to mix, e.g. with wide-bore pipette tips (to reduce shear stress on the cells).

The required number of cell are then transferred to the two fresh plates 116, to achieve the target confluency in the freshly seeded plates, which may be e.g. 20% confluency.

Various methods can be used to determine the volume of cell mixture to be transferred. For example, the cells may be counted in an automated cell counter or the number of cells may be estimated based on the confluency just before passaging. In any case, the pipetting head aspirates the required volume of cell suspension (containing the desired number of cells), and seeds the cells into the fresh plates. The wells in the fresh plates may be topped up with fresh medium, if required, to reach the correct amount of medium per well. The freshly seeded plates are then re-lidded, and returned to the incubator. The old plates are discarded, and the medium, PBS and trypsin may be returned to storage in plate hotels in the relevant carousels 108, as shown in FIG. 20C.

In the handling strategy described for simplicity, all the materials required (the fresh plates, the PBS, trypsin and medium, the pipette tips), are all loaded onto the rotating working deck 330 at the beginning of the process. Other sequences of movements are possible. For instance, the pre-warmed liquids may be loaded onto the working deck 330 only when they are required.

As described previously, there is a requirement for automation equipment that handles more complete and integrated workflows. At present, this requires making equipment that handles a diverse set of legacy human-optimized lab-ware that is difficult to handle in an automated system. Provided here is a set of lab-ware, and methods for using, that accomplish end-to-end automation of complex cell culture workflows, using substantially only lab-ware that conforms to an SLAS microplate footprint, thereby adapting the workflows into a format that is readily handled by automation equipment. Also provided is a universal format, for robotic handlers, racks, slots etc., and stores conforming to this format, for handling the lab-ware set.

As discussed above, the lab-ware with a footprint compatible with a microplate footprint 116 are to be grabbed by a grabber arm 164 and more particularly by gripper fingers 168. Therefore, in order to have one robotic device 160 to access all the storage modules (i.e. the fridge 128, freezer 126, the plastic-ware store module 122, etc.) a standardized form for the plates 116 is used. Microplates or Microtiter plates 116 are often used in cell culture processes.

As described herein, the terms 'microplate' and 'plate' are used interchangeably, with the intention of meaning 'lab-ware with an SBS/SLAS microplate footprint', and comprising a set of lab-ware including microplates, microplate reservoirs, single well cell culture plates, multi-well cell culture plates, microtiter plates, bottles, pipette tip boxes, adaptor racks for vials and/or bottles that all use the same base footprint so they can all be operated within the modules 100 by the same robotic device handlers 160. Furthermore, these lab-ware can all have a microplate base footprint for ease of compatibility.

Figure 13A:
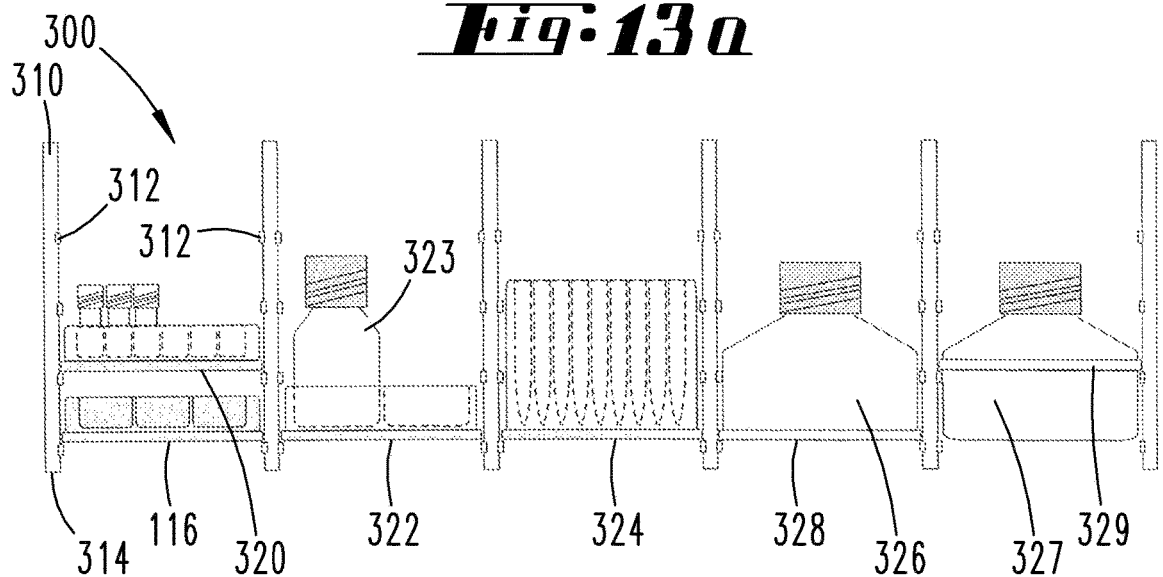
FIGS. 13A and 13B show side view schematics of lab-ware according to an embodiment.

Referring to FIG. 13A, there is provided a set of lab-ware 300, arranged in racks 310. The racks 310 are arranged as vertical stands 314 having rack rails 312 arranged to extend slightly into internal area of the rack 310 between two vertical stands 314. As these rack rails 312 only extend into a part of the internal area, to place a plate 116 on the rails 312, they only interact with part of the plate 116 (or lab-ware), and do not restrict the height as they do not extend across a rack stand 314. The gripper fingers 164 are still able to interact with the plates 116 and other lab-ware 300 as they grab above the rack rails 312. This is discussed in detail with reference to FIG. 13B below.

A microplate 116 (or similar) is shown set on rails 312 of the rack 310 in FIG. 13A. There is also shown a vial plate 320 which is also set on rails 312. However, in the embodiment, the vials 321 in the vial plate 320 extend beyond the height of the next rails 312 positioned above it. As the rails 312 do not encroach into the area internal of the rack 310, other than far enough for a footprint of the plate 116 or vial plate 320 to be positioned on the rails 312, the vials 321 can extend beyond the height of the next rails 312.

The vertical stands 314 can be arranged such that each column can be placed side by side in rows to form a row of racks 310, with rails 312 extending from both sides of the vertical stands 314. This allows a compact rack 310 as each vertical stand 314 can form a part of the rack 310 for a further rack 310. In this arrangement, the robotic device 160 would need to be able to move not only in a single horizontal dimension, i.e. toward and away from the rack 310, but also in a second horizontal dimension, left and right to access an adjoining rack 310, thus z and y axes. Where a rack 310 is arranged on a carousel 108, it would not be possible to use a single vertical stand 314 for two racks 310 as the racks are arranged in a radial manner.

A bottle tray 322 is shown in FIG. 13A where a footprint of a microplate 116 has a tray suitable for holding a number of bottles 323. As with the vial plate 320, the bottle 323 is shown to extend beyond the height of the rails 312 above it, where this is possible due to the rails 312 only extending into the internal area of the rack 310 a distance to hold the footprint of the microplate and thus does not restrict the height of the bottle 323. A pipette tip tray 324 is also shown where, similar to other examples, a footprint of a microplate 116 has a pipette rack suitable for holding a number of pipettes while being able to be housed in a rack 310 where the height between rails 312 is shorter than the height of the pipette tip tray 324.

Two examples of large bottles 326, 327 are shown in FIG. 13A. The large bottles 326, 327 are manufactured to have the same footprint as the plates 116 and trays 322, 324. Therefore, the bottles do not sit on a microtiter footprint rack as is the case with other lab-ware 330. There is provided an extended portion 328 at a base of the bottle 326 which has a width that is greater than that of between the rails 312 but less than the width between adjacent vertical stands 314 of the rack 310 such that the bottles 326, 327 are suspended by the rails of the racks. The bottle, which is narrower than the width between the two rails 312 then extends from the extended portion 328. There is also provided a bottle 327 having an upper extended portion 329 that reaches between the rails 312 of the rack 310 such that it is suspended by the rails 312. However, the upper extended portion 329 is positioned at a mid-height of the bottle such that the bottle 327 extends in both directions, (i.e. up and down) from the extended portion 329. Therefore, the bottle 329 can be placed on a higher set of rails 312 and suspends downwards yet also extends upwards. This contrasts with the bottle 326 that has the extended portion 328 at a base which extends upwards relative to the rack 310 height. This allows the bottle 326 to be placed on the lowest set of rails 312 of the rack 310 and passes rails 312 above it.

The extended portions 328, 329 and/or bottles 326, 327 can be shaped such that they have a horizontal circular cross-section, i.e. form an outline of a circle when viewed from above. This allows for a conventionally shaped bottle which can still be held in the rails 312. Alternatively they can have flat sides such that the extended portions 328, 329 extend along the length of a rail 312 and thus provide a larger supported surface area for suspending the bottles 326, 327. The bottle can optionally be circular or have a similarly flat sided shape, where a more rectangular shaped bottle (when viewed from the top) will be a more efficient use of space and as is often used in cell culture operations.

This all results in a versatile racking solution whereby specific sized plate slots 110 need not be provided for differing lab-ware, but instead, the plate slots 110 are universal to allow many types of lab-ware to be housed in them. Furthermore, in some embodiments, the plate slots 110 do not need to be specifically sized for particular height contents, but instead, the plate slots 110 can allow for an item of lab-ware 300 that is taller than the set of rails 312 as these do not encroach on the height of the plate slot 110 and thus rack 210, 310.

The racks 210, 310 as previously described are situated on a carousel 108. In some cases, the racks 210 can be fully removed from the carousel 108 and loaded with a new rack 210, 310. This can allow new sets of plastic-ware 300 and plates 116 to be preloaded onto a rack and replaced. Access to the rack 210, 310 can be through a user accessible door. The height of the door would need to be equal to that of the rack 210, 310 that is removed or placed in the module 100. To avoid contamination or a change of the environment of the module, the replacement of a rack 210, 310 can be combined with a load-lock. In some cases, it is only modules 100 used for plastic-ware storage or storage at room temperature that can be accessed for rack 210, 310 switching.

A carousel 108 has been described in the singular for each module 100. However, a plurality of rotating disks can be provided to form a carousel to hold a rack 210, 310. For instance, a bottom turntable and top turntable can be provided with space for a rack 210, 310 to sit between. In some embodiments, rows of plate slots 110 sit on independent carousels 108 that rotate independently in the same module 100.

When researchers are culturing large numbers of cells, they will use flasks for the larger quantity. In contrast, plates are used when users want multi-well plates, for doing several cultures or experiments in parallel. Single well plates can be provided that have a large liquid surface area, e.g. a surface area of 77 $cm^2$, similar to T75 flasks. While these would be inconvenient and unconventional for humans to use, single well plates can be used by a robotic device 160. This will simplify the mechanical handling in an automated system.

Figure 13B:
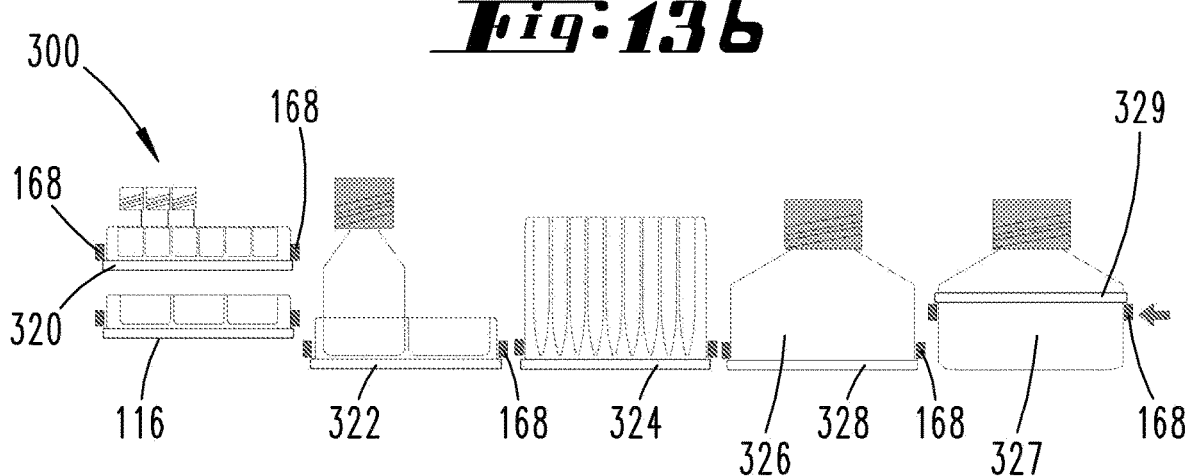

FIG. 13B shows the same set of lab-ware 300 as shown in FIG. 13A. However, the gripper fingers 168 are shown interacting with the various lab-ware 300. In the case of the plate 116, the gripper fingers 168 grip each side of the plate 116 (excluding the footprint that sits on the rails 312. Given that it is the sides of the plate that are gripped, there is no encroaching of the gripper fingers 168 into the area above (or below) the plate 116. This allows the plate, or contents therein, to not be limited to a particular height. The only limitation on height can be the height of the rack 310 (or module 100) in which the lab-ware 300 is intended to sit or an interface 134 through which the lab-ware 300 is to pass through.

In the vial plate 320, the bottle tray 322, the pipette tip tray 324 and the large bottle 326, the gripper fingers 168 all grip the of the lab-ware 300 above the footprint that sits on the rails 312. Notably, when placed on the rack 310, there is sufficient space between the vertical stands 314 and the side of a plate 116 or other piece of lab-ware 300 for the gripper fingers 168 to be able to fit. This is because the footprint of the lab-ware 300 (or the extended portions 328, 329 in the case of the large bottles 326, 327) is wider than the width between the sides of the lab-ware 300. In the case of the large bottle 327, as the extended portion 329 sits on the rails 312, the gripper fingers can instead grab the bottle 327 at a position lower than the extending portion 329.

The described system handles cell culture plates 116, liquid media (which generally come in bottles 323, 326, 327), liquid additives (such as growth factors) that come in e.g. 2 mL vials 321, sample plates 116 (for storing samples taken from the cells), pipette tips (in pipette tip boxes 324), etc. All of these different objects can be handled differently by the same system 99 using the robotic device(s) 160. This results in an automated cell culture system 99 that is highly autonomous for prolonged operation. This allows the system to handle complex workflows.

Referring back to FIGS. 3A and 3B, a process module 120 is shown where various lab-ware 300 is shown on a working deck of a carousel 108 that is in accordance with the above description. Notably, as the plate slot 110 is the same size and configuration throughout the system 99, such as that on a working deck of a carousel 108, all the lab-ware (e.g. plastic-ware) 300, including the vials 321, bottles 323, 326, 327 and pipette tip boxes 324, is handled with the same gripper fingers 168, stored in the same sorts of rack 210, 310 and carousel 108, and sits in the same sort of dock 110 on the rotating working deck.

The vials normally hold 0.2 to 2 mL of liquid. They are often screw capped, although other arrangements are possible. The vials can be 0.2-2 mL cryovials.

Pipette tips may commonly be stored in space-saving stacks, or magazines, because they take up a large amount of space, and because a system 99 uses such a large quantity of pipette tips. However, it is advantageous to have a range of tips available, such as 10 μL, 100 μL and 1 mL tips. It may further be advantageous to have other tips, e.g. wide-bore 100 μL and 1 mL tips, and aerosol resistant versions of those tips. If the tip boxes 324 were pre-loaded onto a deck, or if there were magazines for the boxes, this flexibility would require a large number of slots 110 or magazines. This may require a large or complex deck. Therefore, while handling tips in single boxes 324 appears to use a large amount of limited space, it actually achieves good occupancy of the system 99, because of the flexibility and lower downtime by simplifying the mechanics. Less human interaction is also required to change tips when required. A variation of these embodiments can be adopted depending on the requirements of the system 99.

Figure 14:
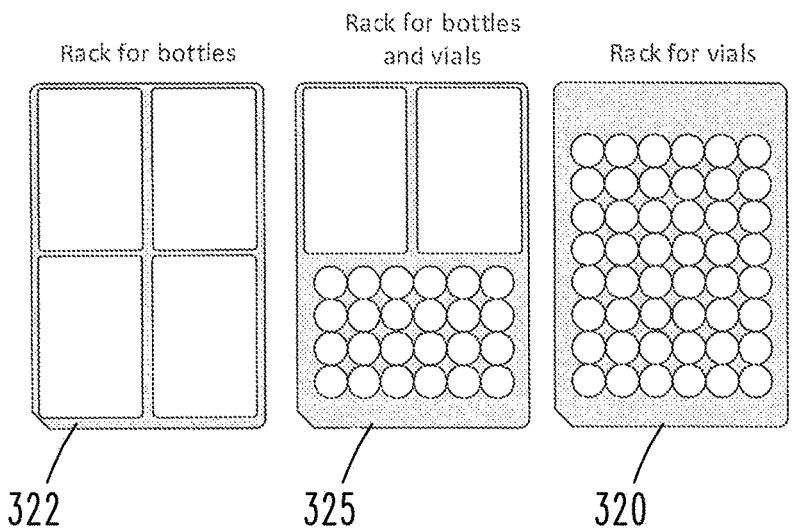
FIG. 14 shows pan view schematics of lab-ware.

FIG. 14 shows a plan view of different trays or plates 116 for different functions, for instance, on the left a bottle tray 322 is shown where four areas are demarked for bottles 323, on the right a vial plate 320 is shown where 48 slots for vials 321 are provided. However, in the center a tray 325 is shown which has a combination of slots or areas so that bottles and vials can be contained in a single tray 325. Various combinations for a tray 325 can be provided as per the requirements of the system 99.

The various lab-ware 300 can have computer readable means such as barcodes, RFID or NFC chips that allow the type and configuration of the trays or plates to be logged on a system. The reader can be present on the robotic device 160 to detect the tray or plate when selecting this.

Cell culture plates typically require 10-15 mL of medium. This is typically pipetted with 15-20 mL serological pipettes, from 100-500 mL bottles of medium. Serological pipettes were originally designed for manual use, and are typically rigid, being made of a polymer such as polycarbonate, and often have an inside diameter that is widest at the middle of the length of the body, and narrower at the tip, and also narrower at the end that connects to a mechanism for applying air pressure to aspirate or dispense liquid. This conventionally requires an automated system to handle bottles and serological pipettes, which tends to result in complex and failure-prone robots. In contrast, conventional pipetting robots are highly mature and reliable, but typically the heads only handle up to 1 mL, which would require a long series of pipetting steps to transfer 10-15 mL of medium. Pipetting robots generally have a piston, and often work on air displacement. They use disposable pipette tips, which are somewhat compliant, being generally made of a polymer such as polypropylene, so as to be able to fit sealingly onto the outside of the pipette 'cone'. Pipette tips have a substantially greatest inside diameter where they fit onto the pipette cone.

It is also noted that a deep well plate 116 can be used as a media store vessel, instead of a bottle 323, 326, 327. Deep well plates can be used in the present system and will simplify handling in an automated robotic system 99. Further, deep well plates 116 can be sealed by a film (to prevent liquid leaking during shipment), which may be ruptured by the pipette. Alternatively the lid of the plate might seal, or there might be a gasket. A 96 well plate, with 2 mL wells, can hold 192 mL of medium, similar to a bottle, in a space-efficient format. A deep well plate, unlike a bottle, but similarly to a trough reservoir, is accessible to a multi-channel pipette head. An 8 channel pipette head with 1 mL pipettes, can pipette 8 mL at a time from a deep well plate, so filling a single well plate with up to 16 mL of media only requires 2 pipetting steps. Although using a multi-channel pipette head to fill plates with media initially appears inefficient, using deep well plates as high volume liquid reservoirs, and pipetting with a multi-channel pipette, greatly reduces mechanical complexity in an automated system, is space-efficient allows efficiency, and is flexible and therefore favoring high occupancy (i.e., efficient use) of the system. A single well plate is herein used as a robot-friendly substitute for a T75 flask. A T75 flask is useful for maintaining cell stocks, having a large a growth area of 75 cm², and while humans prefer to use flasks, they are robot-unfriendly. On the other hand, while single well plates exist, they are almost never used as they are awkward for a human to use—it is easy to tilt them and spill media. However, single well plates are robot-friendly, and can have a growth area of 75 cm² or greater. In an automated system, it may further be advantageous to decrease the height of the plate, e.g., to 15 mm or less, or 10 mm or less, to increase storage density. This would be normally be disadvantageous for human use, as it would make it easy to spill liquid by tilting the plate.

In an example for using the system, the user loads the system with the liquids required by the system 99. The liquids may be transferred from a bottle 326, 327 into deep well plates (e.g., by an automated liquid handler or dispenser), or they may have been supplied in deep well plates by the supplier as discussed above. The user may load deep well plates containing medium, PBS (Phosphate Buffered Saline), and trypsin into racks 210, 310 in the carousel 108 of e.g., the fridge 128 of the system 99. When the system 99 is ready to passage cells, the robotic device 160 in the fridge 128 retrieves media, PBS and trypsin from racks 210, 310 in the fridge 128, and passes them to empty racks 210, 310 in the incubator 124 for 5 minutes to warm up. After 5 minutes, the system transfers a box of 1 mL pipette tips 324, and at least one fresh cell culture plate 116, onto the working deck 108. The robotic device 160 of the plastic-ware store 122 retrieves a box of tips 324 from a slot 110 in the carousel 108 and passes it onto a slot 110 on the working deck 108, which has been rotated to align with the door 130 of the plastic-ware store 122, where the tip box 324 is passed out, and also passes out a fresh tissue culture plate 116 in a similar manner. The working deck 108 then rotates to align the slots 110 that will receive the PBS, media, and trypsin, to the door 130 of the incubator 124, where the robotic device 160 in the incubator 124 passes those liquids (in their deep well plates 116), onto the appropriate slots 110 on the turntable 108. The robotic device 160 then passes out the plate 116 with the cells that need to be passaged.

Referring to FIGS. 21A-21D, improved interfaces for the robotic device 160 and in particular the interface between the handler or gripper fingers 168 and the plate 116 or other compatibly lab-ware 300 are shown.

In general, the interface comprises mating dock and key' features on the handler and lab-ware. The features may be e.g. bevelled or conically shaped, so as to align the lab-ware onto the handler as it is picked up, being able to correct for a few millimeters of mis-alignment. The handling interface may further al low lab-ware to be held more securely. The features may further allow the system to detect and reject incorrectly dimensioned lab-ware, which does not carry the handling interface.

In FIG. 21A, a plate 116 having a footprint 360 with grooves 370 extending through its side walls is shown. In particular, the groove 370 originates at an edge of the footprint 360 and extends along the length of the plate 116. In some embodiments, the length of the groove 370 does not exceed half the length of the plate 116; furthermore the length is equal to (or longer than) the length of a gripper finger 168. The groove 370 is closed on the upper and lower surfaces of the footprint 360. However, the groove 370 can be open on the sidewall of the footprint 360 closest to the open side to form a channel. A groove 370 is also provided on the opposing end (i.e. across the width of the plate 116). The two grooves 370 are dimensioned to allow a pair of gripper fingers 168 to slide along the groove 370 to handle a plate 116. Lab-ware 300 other than plates 116 preferably have a footprint that is similar or identical to that of plates 116. Thus the grooves 370 can be provided on all lab-ware 300.

The upper and lower surfaces of the groove 370 restrict vertical movement of the plate 116 relative to the gripper fingers 168. The gripper fingers 168 consequently do not only have to rely on a horizontal force to handle a plate 116, but the plate is also constrained in a vertical direction. Therefore, the likelihood of dropping plates 116 is reduced. An equivalent pair of grooves 370 can be provided from the opposite end of the plate 116 to allow gripper fingers 168 associated with a robotic device 160 to handle the plate 116 from both sides and be able to hand-off the plates 116 to one another.

Alternatively, the grooves 370 could be enclosed on the sides, or open on a lower surface. Different shaped grooves 370 could also be provided; for instance, they could be square or circular in cross section. Instead of the gripper fingers 168 aligning into a groove 370, the feature could be reversed so that a flange on the lab-ware 300 aligns into a bevelled groove in the gripper fingers 168 or on a rack 210.

In FIG. 21B, a set of gripper fingers 168 having conical or pyramidal protrusions 372 and a plate 116 having equivalent conical or pyramidal indentations 374 is shown. The conical protrusions 372 are positioned on the face of the gripper finger 168 that faces and grips against the side of the plate 116. The corresponding conical or pyramidal indentation 374 is provided at an outer edge of the plate 116 that faces the gripper finger 168. In operation, the gripper finger 168 extends along a designated length of the plate 116 and closes in toward the plate 116, thus grasping it. This designated length is such that the indentation 374 and protrusion 372 are aligned. Small amounts of misalignment between the plate 116 and gripper fingers 168 are automatically corrected as the conical/pyramidal protrusions 372 move into indentation 374, moving the plate 116 such that it correctly aligns with the gripper fingers 168.

Corresponding conical or pyramidal protrusions 372 and conical or pyramidal indentations 374 are provided on the gripper finger 168 on the other side of the plate 116. The protrusions 372 and indentations 374 do not need to be horizontally aligned. Providing the protrusions and indentations at two different vertical heights ensure that only plates that are orientated the right way up, for instance will be handled. Furthermore, if the protrusions 372 and indentations 374 are not horizontally aligned across the width of the plate 116, then the plate 116 will not be able to rotate about the indentations. In FIG. 21B, there are provided two protrusions 372 and indentations 374 on one side positioned at extremities of the gripper finger 168, i.e. one is positioned toward the end of the gripper finger 168 and the other is positioned at the start of the edge of the plate 116. On the other side, there is a single protrusion 372 and indentation 374 positioned horizontally between the protrusions 372 and indentations 374 of the other gripper finger 168. The conical or pyramidal shape allows for alignment and also assists with the gripping as not only is an inward force of the gripper fingers 168 required to hold a plate 116, but there is also a vertical component provided by the conical or pyramidal shapes to reduce the likelihood of the plate being dropped by the robotic device 160.

Other shapes instead of conical or pyramidal could be used. For instance semi-circular protrusions 372 and indentations 374 could be envisaged. Any number of protrusions 372 and indentations 374 could also be provided as desired. For instance, there need not be protrusions 372 and indentations 374 on both gripper fingers 168.

Referring to FIG. 21C, a similar protrusion 372 and indentation 374 arrangement to FIG. 21B is shown. However, additional indentations 374 are provided on sides of the plate 116 that cannot be reached by a gripper finger 168 when approaching from one side. Furthermore the indentations 374 are mirrored both horizontally and vertically. That is to say that the indentations 374 are positioned such that a plate can be picked up by a robotic device 160 having protrusions 372 from either side of the plate 116. This allows the plate 116 or other lab-ware 300 with such indentations to be handled by two robotic devices 160 simultaneously and also to be passed off between robotic devices 160 or modules 100.

FIG. 23 shows such a hand-off between a pair of robotic devices 160. Here, two sets of gripper fingers 168 can engage the plate 116 at the same time to provide a hand-off in which secure control of the plates 116 is maintained throughout.

Referring to FIG. 22, a dock or plate slot 110 for the lab-ware 300 is provided to interact with the indentation 374 to allow the robotic device 160 to hand-off to the plate slot 110. Here, in the plate slot 110, instead of providing protrusions 372, feedback means 378 are provided at a position in which, when a plate 116 is located in the plate slot 110, the feedback means 378 extend into the indentations 374 in the plate 116 providing feedback that the plates 116 are fully placed in the plate slots 110.

The feedback means 378 in the plate slot 110 can provide mechanical feedback, i) when the lab-ware 300 has begun to engage the plate slot 110, ii) that the lab-ware 300 is fully engaged, and iii) that the lab-ware 300 is in the correct orientation, and carried the correct handling interface. The feedback means can be in the same manner as describer earlier with reference to FIG. 18, i.e. a contact is triggered when the feedback means 378 is in the indentation 374. Alternatively, the feedback can be based on the depression of the spring or other elastic means in the feedback means 378 when depressed by the plate 116 and when in the indentation 374.

The feedback would be reversed when the operation was reversed i.e., when a robotic device 160 is removing the lab-ware 300 from the plate slot 110. Each of the plate slots 110 on the working deck 330 or in the racks 210 can have these features. In one embodiment, one or more or all of these features are combined with the engaging means 362 described with reference to FIG. 18.

The gripper fingers 168 and plate 116 of FIG. 21C have a single protrusion 372 and indentation 374, respectively, on each side of the plate 116. However, additional indentations 374 are respectively provided on the front and end faces 116 of the plate. A protrusion 372 is moreover provided on the beam 376 of the grabber 162 that extends perpendicularly between the two gripper fingers 168 to join them together. Such a protrusion 372 and indentation 374 further provides alignment of the plate 116. As discussed previously, the number or shape of the protrusions 372 and indentations 374 both on the beam 376 or gripper fingers 168 is not limited to those discussed above. In one embodiment, the indentation is provided off center on the respective end faces of the plate 116 to restrict handling to plates 116 that are positioned the correct way up.

Referring to FIG. 21D, here it is shown that the protrusions 372 and indentations 374 are positioned on the footprint 360 of the plate 116. This further reinforces that these protrusions 372 and indentations 374 do not encroach into the inner volume of the plate 116 or lab-ware 300 as these have a wider footprint 360 area that assist in handling. Given the standardized footprint 360 described above, for instance with reference to FIGS. 13A and 13B, the protrusions 372 and indentations 374 are compatible with all the lab-ware 300 that has been discussed above.

The two types of features, grooves 370 and the protrusions 372 and indentations 374 can be combined in one interface or plate 116.

The cone mating of the protrusions 372 and indentations 374 will tend to self-align, even if the plate 116 is a few millimeters out of alignment with the gripper fingers 168. Both of the discussed mating features (grooves 370 or cones 372, 374) will also allow the gripper fingers 168 to more securely and reliably hold the plate by preventing the lab-ware 300 from slipping or dropping vertically, from the gripper fingers 168. With the three indentations 374 of FIGS. 21B and 21C, it allows the unique specification of the orientation of the plate 116. The protrusions 372 and indentations 374 align the plate in all three dimensions onto the gripper fingers 168. This can be used to feedback the information that the plate has been correctly acquired, in the correct orientation.

Both the grooves 370 and the indentations 374 allow the gripper fingers 168 to determine whether the lab-ware 300 carries the correct handling interface. This allows the system to exclude lab-ware 300 that does not carry the interface, which in turn allows the system 99 to exclude non-correctly dimensioned lab-ware 300. This results in a more reliable system and poorly toleranced third party trays can be excluded. This can be used to create a partially closed system, where it is more easily possible to control the reliability of the system 99.

Plates carrying the grooves 370 and protrusions 372 and indentations 374 can still comply with the footprint of a microplate (SLAS plate).

Figure 24:
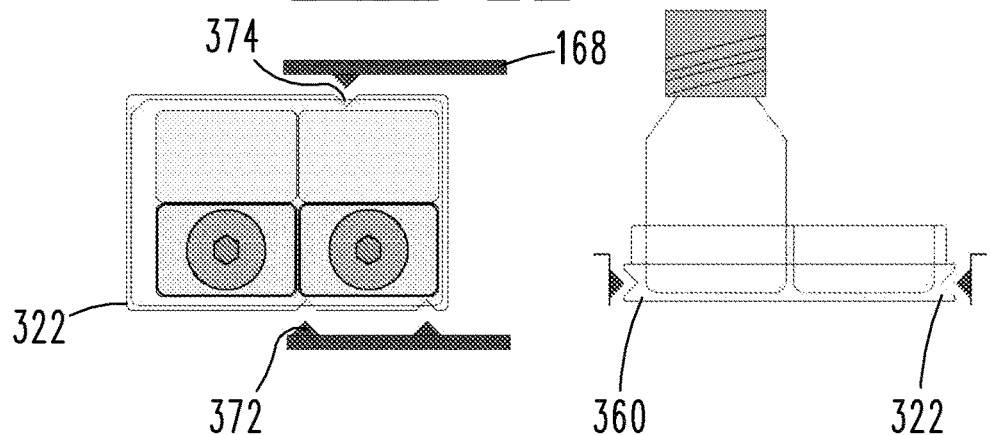
FIG. 24 shows plan and side view schematics of lab-ware for use with the handling device of FIGS. 21A-21D.

As discussed above, the interfaces of FIGS. 21A-21D can be used on lab-ware 300 and not just strictly plates 116. Referring to FIG. 24, a bottle tray 322 is shown where the protrusions 372 and indentations 374 are provided. In particular, the bottle tray 322 has indentations 374 and it can be seen that these are positioned in the footprint 360 of the bottle tray 322. Therefore, this can be adapted for all types of lab-ware 300.

Figure 25:
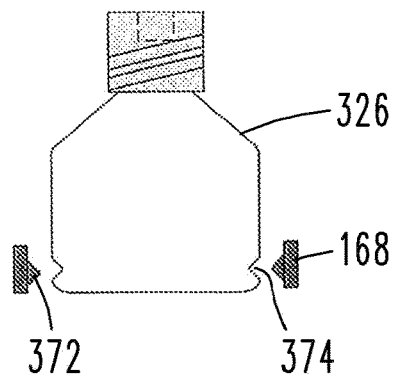
FIG. 25 shows a side view schematic of a bottle for use with the handling device of FIGS. 21A-21D.

Referring to FIG. 25, a large bottle 326 is provided that has the width of a plate 116. It provides the cone mating of the protrusions 372 and indentations 374; the bottle itself has indentations 374 in the bottle of the body. This allows the gripper fingers 168 to grip the side of the bottle 326 without using a tray for the bottle 326 to sit upon. In an embodiment, the bottles 326 are held in a rack 210 that has protrusions 372 to hold it in place.

Trays, plates or boxes for vials or pipettes adapted to function with a groove 370 or cone mating interface are equally envisaged.

Figure 26:
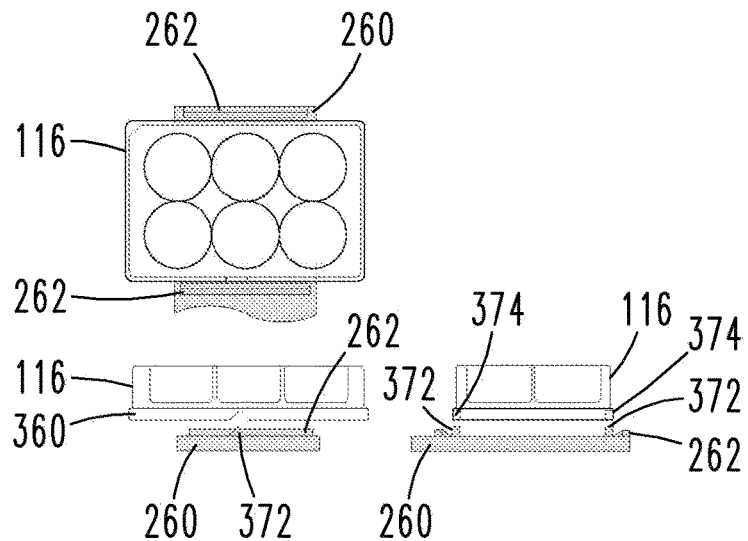
FIG. 26 shows plan view and side view schematics of a handling device according to an embodiment.

Although a pair of gripper fingers has been discussed, other embodiments can use additional means for picking plates while optionally still using the protrusions and indentations described above. Referring to FIG. 26, there is provided a plate 116 with a standard microplate footprint 360. The plate 116 could be lab-ware 300 as previously discussed. Instead of moving or passive gripper fingers, the robotic handler may have an end effector comprising a passive handling plate 260 that extends under the plate 116 to manipulate and move the plate 116. The handling plate 260 is shown to extend across the width of the plate 116 so that it approaches the plate 116 from a width direction. However, other embodiments are envisaged. The handling plate 260 has protrusions 372 extending upwardly from it toward the footprint 360 of the plate 116 when it is positioned thereon. The plate 116 has corresponding indentations 374 in the footprint 360 for the indentations 374 and protrusions 372 to correspond.

The handling plate 260 also has placement means 262 that allow for the aligning of the plate 116 when positioned on the handling plate 260. These placement means 262 extend along the preferred position of the plate 116 on the handling plate 260 and are sloped or tapered to encourage the plate 116 to slide into the correct position when placed thereon.

The protrusions 372 and indentations 374 are shown positioned eccentric to the centerline of the plate 116. However, various configurations are possible as discussed with reference to the gripper fingers. For instance, the plate 116 can have multiple indentations 374 to allow handling plates 260 that approach from different directions the ability to pick up the plate 116. The protrusions 372 and indentations 374 can also be reversed. Additional protrusions 372 and indentations 374 can also be provided.

The use of a handling plate 260 allows the width of interfaces 134, racks 210 and plate slots 110 to be minimized to the width or length of a plate 116 without needing to consider the handling width as this is less than the plate 116. The handling plate 260 also provides a solid base to increase the stability of the plate carrying operation.

Figure 27:
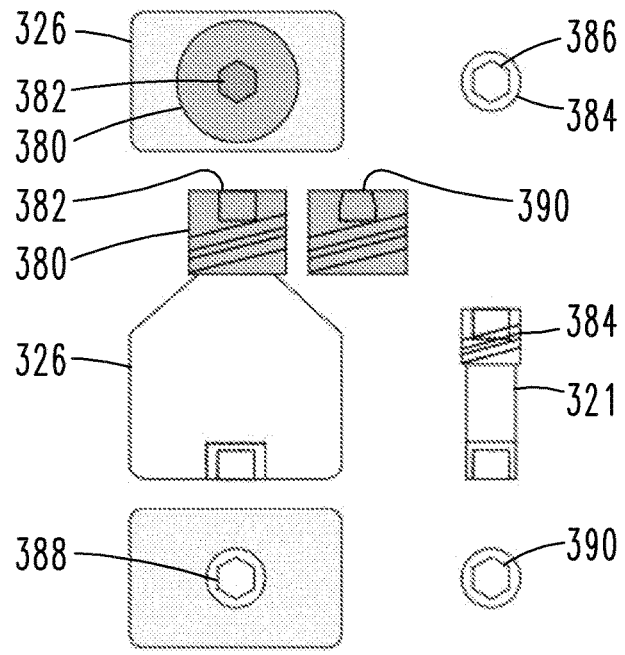
FIG. 27 shows plan and side view schematics of lab-ware with interfaces for handling with caps and lids.

Referring to FIG. 27, an interface for a de-capper built into the bottles and vials is shown. There is provided a bottle 326 with a lid 380. The lid 380 has a capping interface 382 on the top surface of the lid 380. The capping interface 382 is an indentation with a hexagonal shape such that an protrusion with a corresponding shape can interface with (i.e. inside) the capping interface 382. The interface provides a rotational lock such that rotation of the lid 380 will result in rotation of the male protrusion, or vice versa. The protrusion can be used on a decapper 344 to provide more reliable de-capping and capping than the gripping and unscrewing of a conventional lid without an interface 382.

Multiple shapes and interfaces can be used for the capping interface 382. Furthermore, the de-capper can have the female interface and the bottle have the male interface, which may be more conventional with normal automated capping processes.

A vial 321 also has a lid 384 with an indentation on the top surface such that a vial capping interface 386 is formed. As with the bottle lid 380, the vial capping interface 386 is shown to have a hexagonal shape when viewed from above. This allows a protrusion with a corresponding shape to rotationally lock with the vial lid 384 such that a reliable capping or de-capping process can occur.

As with the bottle 326, various shapes of the capping interface 386 could be used. For instance, another polygonal shape can be used to provide a rotational lock.

The bottle 326 has an underside interface 388, where an indentation, similar to that of the capping interface 382, is provided and extends from the underside of the bottle into the body of the bottle 326. The underside interface 388 is shaped hexagonally when viewed from the underside. This allows a corresponding hexagonal indentation to sit inside the underside indentation and rotationally lock. The vial 321 likewise has a vial underside interface 390 which is the same as the bottle 326 underside interface 388. These underside interfaces 388, 390 allow for the bottle 326 or vial 321 to be rotationally held from the underside. This can allow a de-capping machine 344 to be configured to attach to the underside, or it can be used to restrain the bottles from rotating by protrusions on a plate such that a de-capping operation on the lid of the bottle or vial will not result in rotation of the bottle or vial itself.

The underneath interfaces can also be used to prevent bottles 326 or vials 321 from toppling or falling when moved about the system 99 by being placed on trays with specific protrusions to align them. This will also ensure that bottles 326 and vials 321 are correctly aligned on trays and plates for the various robotic handling devices to interact with them.

A combination of the upper and lower interfaces can be used as required. The interfaces provided at the top and bottom do not need to be identical. However, identity of the interfaces could be useful for a uniform operation. The vials 321 and bottles 326 can contain the same shaped interface, so that they can be handled by the same gripper, on the same picking or de-capping robot 344.

Further changes can be made to the capping interfaces 382, 386 such as an undercut interface 390 where the indentation in the lid 380, 384 has a narrower mouth than deeper into the cap. This allows for an interface to have an additional vertical lock, such as the protrusion expanding at a distal end once a lid 380, 384 is removed from a bottle 326 or vial 321. This can reduce the risk of the lid 380, 384 being dropped by the gripper of the picking or de-capping robot 344.

The interface 382, 386, 388, 390 on either the top or bottom portion can be chamfered or bevelled, for alignment of the gripper of a de-capper or picker when approaching the interface. This will allow any slight intolerance in the positioning of the vial 321 or bottle 326, such as in the tray or plate or the tray or plate in the plate slot 110 itself. This will also assist with any machine or robot intolerances. These features can also result in a more reliable system as lab-ware 300 without the correct interface cannot be used in the machine and thus third party or poorly tolerance lab-ware 300 will be rejected and more reliable automation can be realized.

FIG. 1 shows a store module 100 according to an embodiment of the invention. The store module 100 has an outer shell or housing 102 that forms a box having four sides 104. These sides 104 can all be equal in length to form a store module 100 with a square footprint. Although sides 104 of equal length are preferred due to the modular nature and the carousel features inside (discussed in detail later), in some embodiments the sides 104 may be varied in length to result in a module 100 with a rectangular or other polygonal shape. It is further possible to have more than four sides 104.

The length 106 of each side 104 can be 70 cm to 80 cm. In particular, the length 106 of the sides 104 of each store module 100 should be 80 cm or less in at least two dimensions. This ensures that the whole system 99 of modules 100 is compact, which is advantageous, because these systems are installed in laboratories or clean rooms where floor-space is expensive and this allows the modules 100 to fit through doors. This also reduces difficulty and costs to ship the store modules 100.

Inside the outer shell 102, there is provided a carousel 108, where the carousel 108 is a circular plate that occupies the footprint of the store module 100. The carousel 108 has tray slots or plate slots 110 arranged along its radius (i.e. radially). The center of the carousel 108 is open such that there is a center well 112. The plate slots 110 are arranged such that their edges all face into the center well 112. In the figures, the center well 112 has eight tray edges 114 and thus is octagonal in shape. In some embodiments, the center well 112 has flat tray edges 114 such that the center well 112 is a polygon having a number of sides equal to the number of plate slots 110. However, in some embodiments, a circular edged center well 112 can be used, where the tray edges 114 form a circumference of a circular center well 112.

The plate slots 110 are positions that are designated to hold a plate, tray or lab-ware. The plate or tray can be a process plate, cell culture plate, a microtiter or microplate, a plate that holds other lab-ware or vessels or the lab-ware itself. Details of the plate slot and plate are discussed later.

The carousel 108 sits on a floor of the module 100 or can be elevated from the floor.

The modules 100 have a height such that the outer shell 102 forms a cube (i.e. a cuboidal shape). The height of the store modules 100 does not need to be equal to the length 106. However, it is preferred that the height does not exceed that of a doorway and is ideally shorter than a doorway for ease of transport and assembly.

In the vertical arrangement (see FIGS. 9A and 9B described in detail below), the plate slots 110 are vertically stacked so that process plates or other lab-ware can be vertically stacked in racks 210. Therefore, each plate slot 110 has a plate slot on top of it to form a rack 210 of plate slots 110. The design of the plate slot 110 may differ from one that sits directly on a carousel 108 to one that sits elevated above (or below) the carousel 108. This is described later.

The racks 210 can extend through the height 204 of the store module 100. The can also extend below the height of a carousel 108 if it is elevated. The space inside the outer shell or housing 102 can have clean air inside and is built by assembling modules 100 that can lock together—depending on the requirements of each module 100. The interior is therefore hermetically sealed such that there is no requirement for additional expensive shrouding or for the store module 100 being installed in a large, expensive clean air cabinet.

Figure 2:
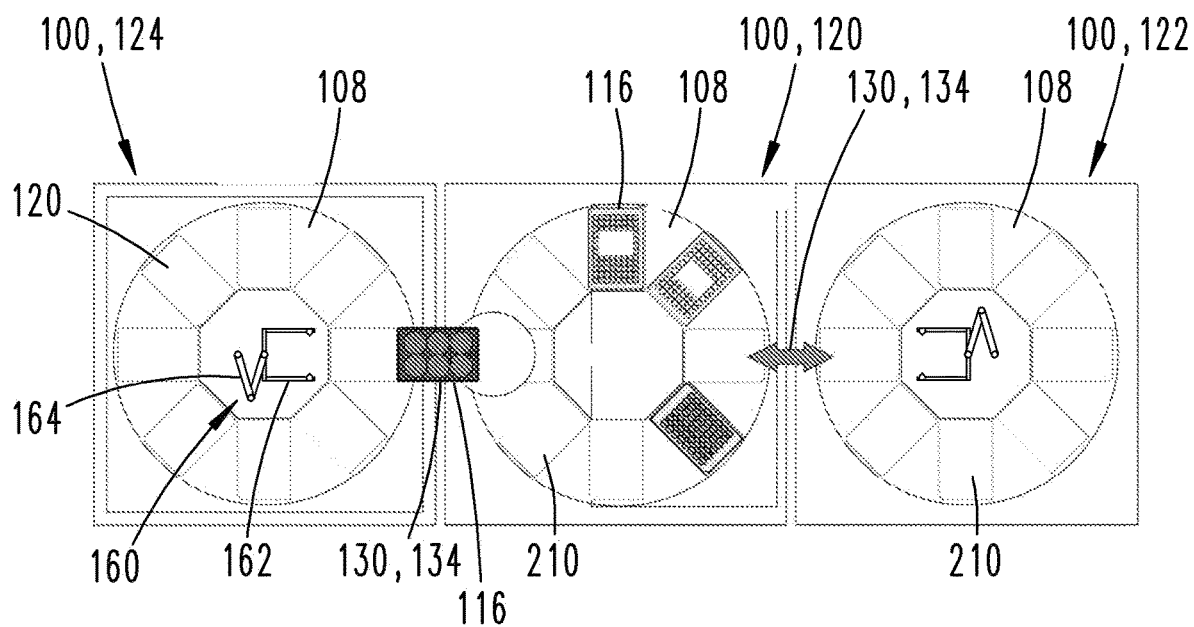
FIG. 2 shows a plan view schematic of the module of FIG. 1 formed into a system of modules.

FIG. 2 shows several of the store modules 100 in a modular arrangement to form the modular system 99. In particular, an incubator module 124 is shown on the far left, a process module 120 is shown in the center and a plastic-ware store module 122 is shown on the right. These modules are indicative and not limiting. However, as is shown, each module 100 uses the same format, e.g. each has a carousel 108 and each has the plate slots 110 formed in or on there.

Other modules 100 can be envisaged, such as a freezer (126; FIG. 3A). Many of the experiments, and the media required for culture, contain reagents that should be frozen if stored for more than a day or two, such as growth factors. This results in a system 99 that will prepare media every day or two, by mixing reagents into a basal medium, where some of the reagents are stored frozen in the system. Therefore, a freezer module 126 can be provided and the system 99 is able to store the frozen reagents, and retrieve and thaw them as required. Another module 100 for the system is a fridge (128; FIG. 3A). Many of the reagents, especially cell culture media, are stored in a fridge, and it would be cumbersome, or even harmful, to repeatedly freeze-thaw them if relying on only a freezer module.

As shown in FIG. 2, in this example for the modular system 99 that is used for cell culture, there is provided a process module 120, and a series of stores, namely an incubator 124 for culturing cells and a plastic-ware store 122 as the right hand side module. As discussed above, other modules could include a fridge for storing media, a freezer for storing e.g. growth factors, samples, etc., and a room temperature reagent store. There are provided slots 110 configured to receive a set of lab-ware 300 designed to fit a slot with a microplate footprint. The set 300 may include a tray, an adaptor rack for bottles or vials, boxes, bottles or a dish. This is discussed in more detail below with reference to FIGS. 13A and 13B. Plates 116 (e.g. cell culture plates, adaptor racks, or lab-ware) can be positioned in the plate slots 110. The plates 116 can carry vials or vessels that can hold reagents or cell cultures. A plate 116 can be transferred between the modules 100 such that, for instance, a plate 116 is passed from the incubator 124 to the process module 120. The transfer occurs at a particular interface 134 in the module 100.

The store modules 100 have an interface 134 at which the modules 100 can present or pass plates 116 (or other plastic-ware). The interface 134 aligns with an interface 134 on adjacent modules 100 to allow the transfer of plates 116 from one module to another. This allows, for instance, the transfer of a plate 116 that holds vials from the incubator 124 to the process module 120. The interfaces 134 can have doors 130 to close access to the module 100. These doors can open vertically or horizontally, can be sliding doors, can have a number of panels or be a single door 130. The doors may vary upon the requirement of the module 100. For instance, some doors are pressure tight or insulating. These interfaces 134 can be in the same plane (e.g., horizontally) to greatly simplify robotic handling. Alternatively, some interfaces can be vertical or a variation thereof. The store modules 100 can be stacked vertically to conserve floor-space. This allows the building of a system 99 by stacking modules 100 together, without requiring a gap or space between modules and therefore a requirement for further handling features to transfer trays 116 or other items between. It also allows for upgrading the system 99, by stacking one more modules 100, to add more function, or more capacity. Vertically stacked modules are described in detail with reference to FIG. 9A. They are connected using a sealing element 311, which forms a pass-way for a gripper.

As discussed above, the modules 100 are joined together with interfaces 134. In some embodiments, these interfaces are hermetically sealed with a sealing element 311 and/or a door so that a complete system 99 with clean air can be built by 'connecting' modules 100, without the need for an expensive and bulky housing to contain a clean air space. Therefore, the interfaces 134 only provide access to an adjacent module 100 instead of passing a plate 116 through an external space outside of the outer shell 102 or housing. To ensure this is maintained, the doors 130, if present, are also hermetically sealed to one another. This also has the advantage of simplifying handling.

FIG. 2 also shows a robotic device 160. The robotic device 160 is positioned in the center well 112 of the module 100. The robotic device has a grabber 162 that can hold plates 116 from the plate slots 110. The robotic device 160 also has a robot arm 164 which is connected to the grabber 162 to allow actuation of the extension and retraction of the grabber 162. The robot arm 164 can be telescopic. The grabber 162 is capable of reaching into a plate 116 holding plate slot 110 (or a rack 210 of the slots 110) and restraining a plate 116 such that the plate can be withdrawn from the slot 110 or rack 210 and placed in a slot 110 or rack 210. The robotic device 160 is also used for passing or transferring plates 116 through the interface 134 such that a plate is passed to an adjacent module 100 by the actuation of the robotic device 160. FIG. 2 shows two modules 100 (e.g., an incubator 124 and a plastic-ware store 122) having similar robotic devices 160 with grabbers 162 and doors 130 in the same place. It is not be necessary for all modules 100 to have robotic devices 160 and some modules 100 can rely on robotic devices 160 from adjacent modules for passing or transferring plates 116. In particular, the process module 120 is illustrated without a robotic device 160.

The robotic device 160 in the center well 112 of a module 100 can pass a plate 116 into a plate slot 110 in another module 100, without any intermediate device, such as a robotic arm or a conveyer belt. This provides a simpler system 99 by eliminating intermediate devices. It also makes the system 99 more compact, by eliminating the space required for intermediate devices, reduces alignment and tolerance stack issues, reduces double handling, and facilitates building a compact system that does not require an additional external shroud or clean air housing.

The robotic device 160 in the center well 112 can have very limited freedom of movement; it can only have 2 degrees of freedom: vertically in the well 112, and horizontally through the door 130 or interface 134, or into slots 110. The carousel 108 can be configured to rotate, to give the robotic device 160 access to all of the racks 210. Therefore the robotic device 160 is constrained to face and move horizontally (and linearly) in the direction of the interface 134, and vertically. Alternatively, in some embodiments the robotic device 160 can rotate and the carousel 108 can be constrained. Or there is a combination of both. The robotic device 160 can be further constrained such as running in rails or having a grabber 162 that runs in a rail instead of an extending robot arm 164. This reduces the possibility for the robotic device 160 to lose its alignment. The modular system 99 also allows for modular software, with code that is reused. This is achieved partly by making the storage modules 100 'self-contained vending machines', in the sense that they autonomously present plates 116 (and other objects) to other modules 100, rather than having e.g., an incubator 124, with an automated door 130 and carousel 108, that a 3D robotic arm reaches into.

FIGS. 3A and 3B show a plan view of a further system 99 comprising of several modules 100. The modules 100 are horizontally arranged and provide an example of complete system 99 built from an incubator 124, a fridge 128, a freezer 126 and a plastic-ware store 122, interfacing with a central process module 120. An 'external' unconstrained 3D robot arm is not required as each of the devices, except the process module, has a robotic device 160 in their center well 112. The modules 100 all interface such that a plate 116 can be passed through adjoining doors 130 or interface 134. The process module 120 is placed centrally such that it has access to modules 100 (incubator 124, a fridge 128, a freezer 126 and a plastic-ware store 122) on each of its sides. Where the extending robot arm 164 is fixed (such that it cannot rotate), it is orientated toward the door of the process module 120 such that plates 116 can be passed in and out of the process module 120. A services module 138 may be added for providing additional functions such as processor units, power means or mechanical units for actuating the robotic devices 160.

In some embodiments, there may be a dedicated 'load-lock', where a module 100 has a door that is accessible to the outside and not connected to a further module 100. This load-lock is routinely human-accessible. This allows users to interact with the plate slots 110 or racks 210 to exchange consumables, plates with cells or samples, etc. within the system 99. The load-lock can be a plate slot 110 that is only open to the outside of the module 100 or the inside at any one time to avoid contamination or the change in an environmental state of the interior of the module 100. This also allows the system 99 to continue operating when the load-lock is accessed by a user without causing any risk of injury as access to rotating or operating machinery is prevented. In some embodiments, the load-lock can be rotatable to access further accessible doors, or to allow the robot handler access to the contents placed in the load-lock.

FIG. 3B shows a system with the same modules 100 as FIG. 3A, i.e. an incubator 124, a fridge 128, a freezer 126 and a plastic-ware store 122. However, the freezer 126 is connected to the fridge module 128 which in turn is connected to the process module 120. This means that the freezer 126 is accessed through the fridge 128, which would reduce frosting and temperature cycling in the freezer 126. A refrigerated module has been described. However, further environmental variations between modules 100 are envisaged such as varying humidity, temperature, or gas concentration. Control means, either automated or user controlled, is provided to control the environment of each module 100.

The process module 120 can optionally not include a robotic device 160 for transferring plates 116. However, other robotic operations can be provided in the process module 120 for an automated cell culture system 99. A liquid handler with a rotating working deck which is interfaced with at least one carousel, or 'turntable working deck' 108 can be provided in the process module 120. Slots in the working deck can be populated with microplates 116 or compatible lab-ware by the simple (horizontal rectilinear) transfers from the suitably disposed carousel 108, and rotations of the turntable working deck and carousel 108. There can also be provided a microscope, other handling modules (vial de-capper, vial picker, plate de-lidder) or other functions on the process module 120. These are discussed below with reference to FIGS. 15A and 15B.

The plates 116 are microtiter plates or microplates, or other lab-ware with a similar footprint, in some embodiments. These plates conform with the SLAS (Society for Laboratory Automation and Screening) standard. This standard requires a microplate to have a width of 85.48 mm and a length of 127.76 mm. However, variations and modifications of this are possible.

A further tube picking robotic device can be provided in the fridge 128 or freezer 126, to permit e.g. frozen tubes being picked from a rack 210, while minimizing the temperature cycling of the other tubes in the rack 210. The picking robot can be built into space sacrificed in the racks 210 of the fridge 128 or freezer 126.

During operation, one or more source storage plates 116 would be retrieved from their shelves or rack 210 in e.g., the freezer 126, and the desired tubes picked from that plate 116 into a target plate 116. The source plate(s) 116 would be returned to storage shelves 210, and the target plate(s) 116, carrying the picked tubes, would be transferred to the incubator 124, to be thawed and/or warmed. Once enough time had elapsed for the target temperature to be reached, the plate 116, with the tubes, would be transferred to the working deck. The process would be reversed to return the tubes, carrying any unused reagent, to freezer storage 126. Bottles or vials can be thawed or pre-warmed, by transferring them into the incubator 124. There can be further de-lidders built into slots 110 in racks 210 in the incubator 124, to save space on the working deck.

A high efficiency particulate air (HEPA) filter for the incubator 124 can be provided where the air in the incubator 124 is recirculated through the filter to reduce particulates inside the incubator 124. An air filter that does not qualify as a HEPA air filter but removes (from the air that passes through) 99.97% of particles that have a size greater-than-or-equal-to 0.3 gm can also be provided.

Figure 4A:
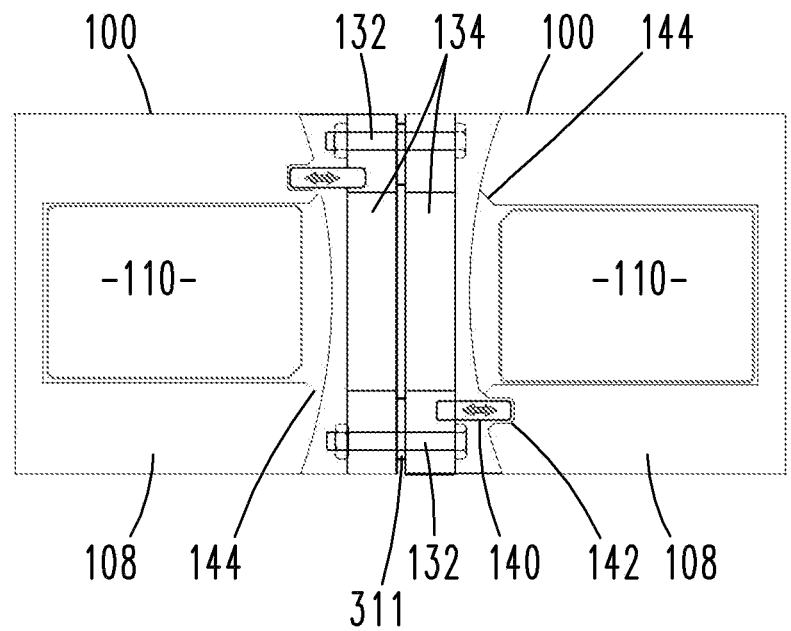
FIGS. 4A, 4B and 4C show a plan view schematic of an interface between modules.
Figure 4B:
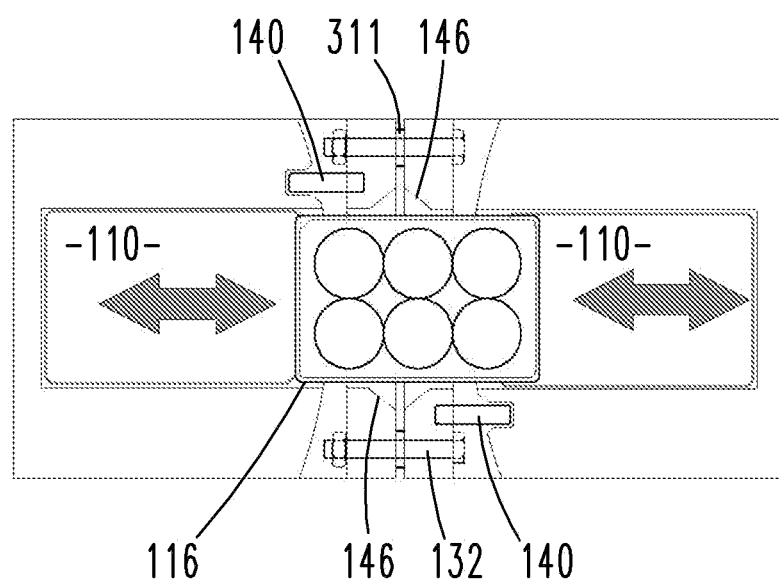

Referring to FIGS. 4A and 4B, a plan view of an interface 134 between two rotating carousels 108 of adjacent modules 100 is shown. FIG. 4B shows a six well tissue culture plate 116 transiting the interface. There is provided an interface 134 between modules 100. Both modules 100 have rotating carousels 108. Only part of each rotating carousel 108 is shown (i.e., one slot for a plate 116). One module 100 may be an incubator 124, with a carousel 108 with racks 210 (also referred to as plate hotels). The main operation that happens at the interface is transferring plates 116 between the two modules 100. In some embodiments, these plates generally conforming to the SLAS dimension standards, such as cell culture plates 116 (for example, a six well cell culture plate 116 is illustrated), or other compatible lab-ware. An automated door 130 (not shown) is provided between the modules. Some modules do not require doors 130 at the interfaces 134. However, where there is, for instance, a different environment between the modules 100, then doors 130 are provided. The two modules 100 are fixed or locked together at the interface 134 by connecting means or fixtures (bolts) 132. The fixtures 132 are close to the interface 134, minimizing a tolerance stack. The fixtures 132 ensure that the modules 100 are aligned and held or locked in a predetermined position for ensuring plates 116 can be passed between modules 100 without any collision between the outer shell or housing 102 of the modules 100. Additional fixtures 132 can also be provided to allow the modules 100 to be joined to each other, or to other features or modules 100 elsewhere. Therefore, the interface 134 provides a controlled location, where the location of the plate 116 is constrained, to hand off the plate 116. The connecting means or fixture 132 is close to the location where the plate 116 is handed off. In some embodiments, the fixture 132 is no further than half a width of the interface 134 from an edge of the interface 134. This reduces the 'tolerance stack' where variances in fixtures and manufacture or movements during operation can have an effect on alignment of alignment critical parts. In particular, because the fixtures 132 are positioned at or near the interface 134, the variance in alignment between the modules is reduced. The connecting means 132 can be a bolt, or any other means that will constraint or exert a compression on the housing of two adjoined modules 100 to hold them rigidly together. In some embodiments, interlocking lips or other indexing means are provided to align the modules to allow the connecting means 132 to be aligned. The carousels 108 are indexed to the interface 134, e.g. by a pin 140 and slot 142 means. The pin 140 is provided in a wall of the module 100. The alignment slot 142 is provided in the carousels 108, where the carousels 108 are capable of for receiving or holding plates 116. The plate slots 110 on the carousels 108 can be aligned to each other, by indexing the carousels 108 to the interface 134, such that transferring a plate 116 (or other compatible lab-ware) between the two plate slots 110 on the carousels 108 can be accomplished by simple linear movement from one plate slot 110 to an adjacent plate slot 110 on a different carousel 108. The pins 140 can move such that the alignment slots 142 are not constrained at all times. Instead, the alignment can be engaged when moving the carousel 108 to a transfer position and at other times can rotate freely. Although a pin 140 and slot 142 have been shown in the figures, other alignment means, electronic or mechanical, can be provided. For instance, the slot and pin position could be swapped such that the pin 140 sits in the carousel 108, or a motor of the carousel 108 can be indexed to stop at certain indexed positions. A plate 116 passing between the modules 100 such that it passes through the interface 134 from one plate slot 110 to another plate slot 110 is shown in FIG. 4B. The plate 116 can pass in either direction, as directed by the robotic device(s) 160.

The movement is driven by the robotic device 160. The carousel 108 rotates and the robotic device 160 travels vertically, then the robotic device 160 transfers plates 116 from any position in the carousel racks 210 to the interface 134, by a combination of highly constrained movements along two constrained axes, i.e. vertical travel to the appropriate level in the rack, horizontal movement to retrieve the plate 160, vertical movement to the height of a working deck (i.e. plate slot 110) of the carousel 108, and horizontal movement to place the plate 116 on the carousel 108 on the plate slot 110. More specifically, the robotic device 160 moves horizontally in a direction along a line connecting the two central axes of the center wells 114 of adjoining modules 100. The interface/door 130, 134 between the adjoining modules are positioned on the respective side walls of the modules so that they are centered in the width direction on the line connecting the two central axes of the center wells 114 of adjoining modules 100. The robotic device 160 can have sufficient horizontal travel to transfer plates 116 directly into slots 110 in the other carousel 108. Not all robot devices 160 require this degree of horizontal movement as a robotic device 160 can be present in the adjacent module 100. In such a situation, a robotic device 160 can hand-off to a robotic device 160 in an adjacent module 100.

FIG. 4A shows further aligning features 144 for ensuring the plates 116 are correctly aligned during a transfer. The chamfers 144 at the edges of the plate slots 110 in the carousels 108 that face the interface 134 serve to capture and align incoming lab-ware 116, even if it is a few millimeters out of alignment. This occurs when the plate 116 collides with a chamfer 144, the chamfer 144 is sloped toward plate slot 110 and thus the plate 116 is slid back into alignment toward the plate slot 110. Alternatively, the aligning features 146 can be present in the interface 134 itself, e.g. in the apertures or doors 130. In such a case, a chamfer 146 can be provided in a door 130 or interface 134 between modules, where the chamfer 146 is shaped such that is slopes toward the plate slot 110 in either module 100. This is shown in FIG. 4B. In such an arrangement, a plate 116 which has gone out of alignment during a transfer may collide with the chamfer 146 and be directed such that it once again aligns with the plate slot 110.

FIG. 8 shows an alternative embodiment of the interface, where the chamfers 146 are positioned on a surface of the interface 134 facing the interior of the module 100. Therefore, the chamfers reduce the width of the mouth of the interface 134 with increasing distance from the center of the module 100. This allows the alignment of a plate 116 and/or grabber 164 entering the mouth of the interface 134. Although not shown, in some embodiments the plates 116 can have chamfers that allow alignment of the plates 116 when entering plate slots 110, interfaces 134, grabbers 164 or any other feature that the plate 116 might interact with. Such aligning features on the plates 116 further allow the alignment of plastic-ware transiting the modules 100 or system 99. A combination of these chamfer locations can be provided in a module 100.

Figure 4C:
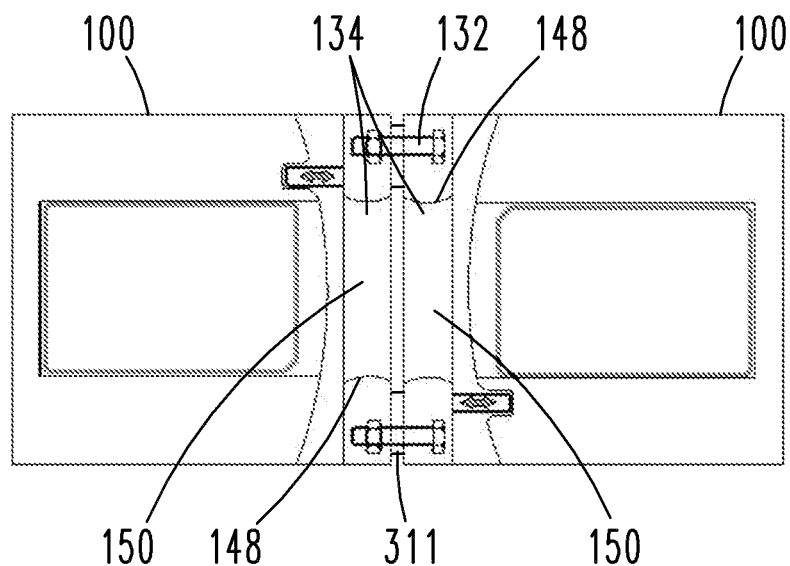

Referring to FIG. 4C, alternatively, or in addition to providing chamfer 144 at the edge or edges of plate slots 110, a concave portion 148 can be provided on the walls of the interface 134. The concave portion 148 is shaped such that the concavity extends toward the center of the interface 134 from the sides of the interface 134. The concavity can be shaped such that the space for a plate 116, i.e. the apertures 150 (the space defined by the interface 134 between the modules 100) is close to that of the width of the plate 116. This ensures that the sides of the plates 116 are flush to the walls of the interface 134 when passing through. Such concave portions can be present on both modules 100 such that there is an extended area through which a plate 116 must be aligned in the concavity 148. The concavity is shaped such that a plate 116 that is out of alignment slides across the face of the concavity 148 until it is aligned such that the plate 116 passes through the interface 148. In some cases, the grabber 164 that manipulates the plates 116 might be wider than the width of the plate 116. In such cases any alignment means, such as the concavity 148, is configured to accommodate the grabber 164 and thus be equal to or slightly larger than an outer width of a grabber 164. In other cases, there might be provided rails or slots that guide or support the travel of a grabber 164. In some examples, the slots can be constructed by making the interface 134 narrower than the width of a plate 116 and the grabber 164, and providing a slot in the interface through which the grabber 134 extends. A combination of the chamfer 144 on the carousel, the chamfer 146 on the interface and the concavity 148 on the interface can be provided. These all act to dynamically align transiting plastic-ware and plates 116, and/or the grabber 164.

Although a space is shown in the figures to provide a clear demarcation of different modules 100, the interfaces 134 can be adjoined such that they are flush to one another. Furthermore, as discussed above, in some embodiments, the interfaces 134 are sealed hermetically. At least some of the modules 100 in an automated cell culture system 99 will have HEPA filtered clean air. Sealing the interfaces 134 prevents the ingress of non-filtered air. The sealing can be accomplished by ensuring there is no gap between modules 100 and/or having seals placed around interfaces 134 or doors 130. A seal could also be provided between the edges of the modules 100.

The apertures 150 (in the interface 134 between the modules 100), and the plate slots 110 in the carousels 108 can be positioned closely, and fit closely to a plate 116 (e.g. a microplate), such that the apertures 150 and plate slots 110 together form a substantially continuous 'race' or 'channel' in which the plate 116, and/or grabbers 164 of a robotic device 160, slide or run, so that the position of the lab-ware is always constrained, greatly reducing the possibility of the lab-ware being dropped, or lost, or going out of alignment.

Figure 5:
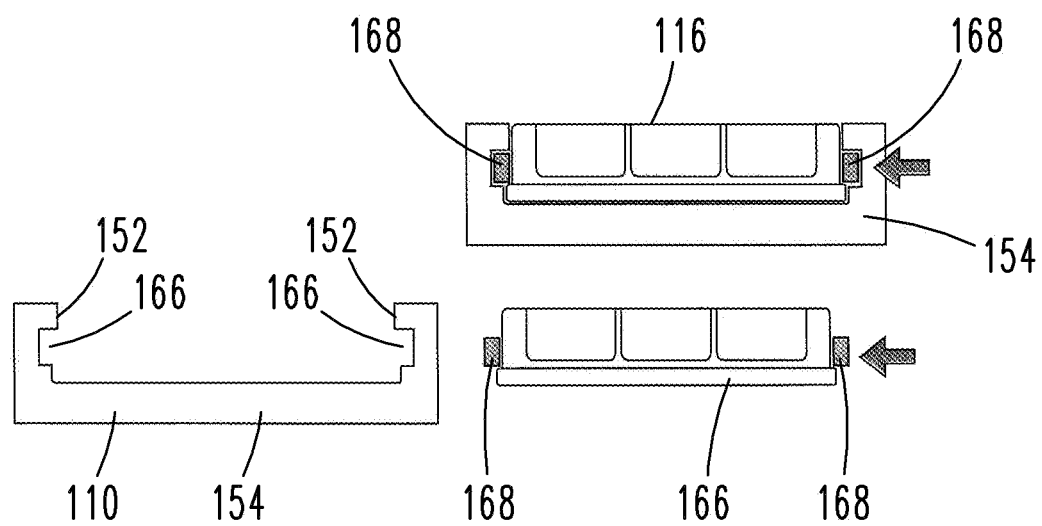
FIG. 5 shows a side view sectional schematic of a plate slot, plate and gripper of a module.

In particular, referring to FIG. 5, a plate slot 110 is shown which has slot sides 152 that extend from a base 154 of the plate slot 110. A plate 116 sits on the base 154 of the plate slot 110 and in between slot slides 152. The slot sides restrain sideward movement of the plate 116. An end of the plate slot 110 opposite to the end of the plate slot 110 in the direction of movement of the plate 116 may moreover be closed off, for example by a back plate or end stop that partially or fully extends between the slot sides 152, to prevent rearward movement of a plate 116. In the slot sides 152, a gripper groove 166 is present. This is a groove 166 that extends along the length of the slot sides 152. The gripper groove 166 is shaped such that the gripper fingers 168 of the grabber 162 can travel along the gripper groove 166 when a plate 116 is present. A microplate 116 is shown where the grabber 164, i.e. the gripper fingers 168 grab a plate 116 by enclosing on either side of the plate 116. This allows the robotic devices 160 to pick up and move plates 116 as required. In some embodiments, the gripper groove 166 only extends partly along the length of the slot slides 152. A corresponding groove 166 can extend from the opposite edge to allow gripper finger 168 to grasp a plate from either side. Other examples of grabbing mechanisms can be provided. For instance, there may be provided a groove in which the gripper fingers 168 fit in the plate itself 116 instead of a base 154 of the plate 116, or there may be provided a slot in the plate 116 itself where the gripper fingers 168 enter the plate body.

The microplate 116 shown in FIG. 5 has a wider base than the width of its sides. To accommodate this shape, the slot sides 152 of the plate slot 110 can have varied widths above and below the gripper groove 166.

FIG. 6 shows a side sectional view of the interface 134 wherein the bottom image illustratively shows a plate 116 passing through the interface 134. As described above, the plate slots 110 in the carousels 108 have a recessed formed by slot sides 152, so that the plate 116 or other lab-ware, and/or a grabber 164 of a robotic device 160, run in a channel 156 or trough or race or rails. In this way, the plate 116 and grabber 164 are highly constrained, and transfers become very reliable. This substantially continuous channel 156 formed at the interface 134 between the modules 100 with the slots 110 in the carousel 108, or between two carousels 108, uses the base 154 of the plate slot 110 as the floor of the channel 156. The plate 116, or other lab-ware, and/or grabbers 164, slide in this channel 156. The channel 156 physically constrains the plate 116/lab-ware and grabber 164, greatly reducing the possibility of dropped or lost lab-ware, and making the system simpler, more reliable, and easier to program.

FIGS. 7A and 7B show a plate 116 in a plate slot 110 of a carousel 108 ready for transfer through an interface 134 to an adjacent plate slot 110. The robotic device 160, with a grabber 164 having gripper fingers 168 is shown transitioning the plate 116 through the interface 134. The robot arm 162 provides the actuation to move the grabber 164. The width of the interface 134 is such that it is close to the width of the gripper fingers 168 to ensure the plate and grabber 164 can fit through and be physically constrained into alignment.

FIG. 8 shows an alternative embodiment of the interface 134, not based on carousels, where the plate slot 110 on a module 100 is a conveyer belt 170. This conveyer 170 can pass a plate through an interface or toward an interface 134. A robotic device 160 may still be present to deliver or retrieve a plate 116 from the conveyer 170. As discussed above, chamfers 146 are also shown, however, the chamfers are positioned on a surface of the interface 134 facing the interior of the module 100.

The modules 100 can be vertically arranged for further flexibility. FIGS. 9A and 9B shows a system 99 having modules 100 arranged in such a manner. This arrangement makes it easier to arrange the systems 99 because it allows more freedom as to where the modules 100 can be placed in the system 99. It makes it easier to add more capacity to the system 99 for instance by stacking the plastic lab-ware store 122, or incubators 124, higher. It allows the system 99 to take up less floor-space, by stacking the modules 100 vertically.

Two modules 100, as discussed previously, are provided such that they are arranged vertically stacked. Between the modules is a vertical interface 234 which can be much like the interface 134 between horizontally arranged modules 100 shown FIGS. 4A-4C. The vertical interface 234 optionally has doors 230, or apertures 231, through which the robotic device 160 can travel vertically. The modules 100 have connection means or fixation points 232 around the door 230 or aperture 231 to ensure the vertically stacked modules 100 are constrained together. The fixation points 232 are arranged close to the aperture 231 or door 230 to reduce tolerance stack as discussed with reference to the connection means 132 in FIGS. 4A-4C. Air-tight sealing means 311 can be located between the interfaces 134, 234 of two adjacent modules.

FIGS. 9A and 9B show a plate rack 210 arranged with multiple vertically stacked plate slots 110. Therefore a rack 210 is formed by the plate slots 110 being formed into layers. Although two racks 210 are shown in FIG. 9A, the racks 210 are arranged on the plate slots 110 around the carousel 108 shown in FIG. 1. The carousel 108 is not shown in FIG. 9A or 9B for simplicity. However, the plate racks 210 rotate about the axis of rotation of the carousel 108 to allow the robotic device 160 access to each column of the rack 210. The robotic device 160 is rotatably fixed so that it can only move in a horizontal direction and a vertical direction. Therefore to access a plate slot 110 behind the robotic device 160, the rack 210 (and thus carousel 108) is rotated so that the required plate slot 110 faces the robotic device. Vertical and horizontal movement of the robotic device can then be carried out to access the plate slot 110. In some alternate arrangement, the racks 210 can rotate in sub groups such that a layer of plate slots 110 rotate independently from plate slots 110 below it. Alternatively, the robotic device 160 can rotate and the racks 210 are held stationary.

As will be understood from the previous discussion, a horizontal interface 134 is present in the module 100. This horizontal interface 134 is formed at a height in the rack 210 that is at the same height as the plate slot 110 of the present module 100 and the required plate slot 110 of the adjacent module 100. These plate slots 110 that are positioned at the height and rotation of the horizontal interface 134 is a transfer slot. The transfer slot is rotatable on the carousel 108 such that it is alignable with the interface 134 of the module 100. A corresponding transfer slot is present in an adjacent module 100. In some embodiments, any plate slot 110 on the rack 210 that is horizontally aligned with the interface 134 can act as a transfer slot; this may include plate slots 110 that are vertically aligned on the rack 210.

In use, to pass a plate out of a storage module 100 (incubator 124, fridge 128, freezer 126, plastic-ware store 122, load-lock, etc.), the carousel is 108 rotated and indexed to the door of the horizontal interface 134, so that the 'transfer slot' in the rack 210 is aligned with the interface position 134 of the module 100. The transfer slot may be empty, or may contain a plate 116 to be transferred. Further, the receiving module 100 is indexed to the interface position 134, so that a receiving transfer slot is aligned to the delivering transfer slot and interface 134, and if a door is present, it is opened, thus forming a continuous space or channel, comprising the transfer slot, the doors or interface 134, and the receiving transfer slot. If the transfer slot contains a plate 116, the grabber 164 travels horizontally into the transfer slot, engages the plate 116, then travels further along the same axis, through the door or interface (134—FIG. 7B), until the plate 116 is in the receiving transfer slot. The grabber 164 then releases the plate 116, and retracts back into its own center well 112. In some embodiments, any slot in the horizontal row can be used as a transfer slot. In some embodiments, the slots on that horizontal row may be used as a buffer (discussed below).

In some embodiments, the interface 134 has a height that is sufficient to pass a cell culture plate 116 such as a microplate. However, in other embodiments, the height of the interface 134 is greater to allow the transfer of taller lab-ware 300 to and from a module 100. The height can be dictated by a door 300 which opens to a required height depending on the plate 116. In such a case, the interface 134 can extend vertically greater than the height of a microplate. More specifically, in some embodiments, the door 130 can be taller on certain modules 100. For instance, the fridge can have a taller door 130 to house bottles. The height of the door 130 or interface 134 would be 4 cm to allow deep-well plates to be transferred, 8 cm to allow a bottle to be transferred and 10 cm to allow pipette boxes to be transferred.

The robotic device 160 is positioned in the center well 112 and is able to transfer a plate 116 or other lab-ware to or from a plate slot 110 on a rack 210 in another vertically arranged module 100. A vertical rail 172 is provided which extends the height of the rack 210 as appropriate to allow the robotic handling device 160 full vertical movement to access all the plate slots 110 on the rack 210. The grabber 162 of the robotic device 160 is connected to the rail 172 by an engaging device 174. The engaging device 174 attaches to the rail 172 by runners 176. The runners 176 are positioned vertically at either end of the engaging device 174. The engaging device 174 actuates the runners 176 such that they move the robotic device 160 vertically along the vertical rail 172. The actuation means can be a motor. The grabber 162 affixes to the engaging device 174 and moves vertically along the engaging device 174. This allows the grabber 162 to reach all plate slots 110 through the height of the rack 210 and not be limited by the height of the engaging device 174. The vertical movement of the grabber 162 can be via a motor or servomechanism present in the engaging device 174.

When transitioning from one module 100 to another module 100, it is necessary to transition to a rail 172 of a different module 100. To accomplish this, a runner 176 disengages from the rail of the module 100 that the robotic device 160 is transitioning out of and therefore the robotic device is held by the runner 176 at the opposing vertical side of the engaging device 174. As shown in FIG. 9B, the disengaged runner 176 then engages with the rail 172 of the module 100 into which the robotic device 160 is transitioning by continued vertical movement from the still engaged runner 176. Continued vertical movement then results in the other runner 176 becoming disengaged and reengaged with the rail 172 of the other module 100. Therefore, the robotic device 160 is always held and constrained in at least one module 100 which at least one runner 176 engaging with the rail 172.

Each module 100 can have its own robotic device 160; alternatively, a single robotic device can be provided that carries out the operations for both modules 100. Where multiple robotic devices 160 are provided, they are constrained such that they do not collide with each other. In some embodiments, the robotic devices 160 have different horizontal planes of movement. Additionally, or alternatively, they operate on different rails 172 or other conveyance means. Where a common rail 172 is used for multiple robotic devices 160, it will be necessary to handover plates 116 between devices to allow access to all plate slots 110 in the module 100.

Although a particular arrangement has been described, other means for transitioning a robotic device 160 are possible. For instance, multiple runners 176 may be used, or a single runner that has a height such that it spans the interface 234 between the modules 100 to ensure it is always engaged on a rail. Multiple rails can also be provided such that the robotic device 160 is constrained at multiple points to ensure better alignment and reduction from any sag from the weight of the plate 116. Alternatively, a rail 172 can be dispensed with and a vertically extending robotic arm can be used that is instead fixed at a single point and is not guided by a rail or any further means for conveying a device vertically.

Therefore, the robotic device 160 can engage alignment and/or indexing features (e.g. rails 172, chamfers in the shelves, slot and pin features, indexed motors) in the other module 100. The transfer may be downward or upward, but does not have to be both.

As previously discussed, the racks 210 are positioned on a carousel 108 such that they rotate and the robotic device is constrained to horizontal movement in one plane. Therefore, by the vertical movement in one plane and the horizontal movement in one plane, the robotic device can access all the plates 116 in the racks 210.

FIG. 10 shows a schematic of a system where a number of modules 100 are provided in a vertically and horizontally stacked arrangement. In this arrangement, a freezer module 126 is provided in a system 99. The freezer module 126 has a robotic device 160 that is capable of grabbing plates 116. The robotic device 160 may be any of the robotic devices described herein. A vial picker may also be provided (described in further detail with reference to FIG. 15B). The freezer module 126 is horizontally connected to a fridge module 128 and a plastic-ware store 122 on its horizontal sides. The robotic device 160 is capable of transferring plates 116 (or other plastic-ware) between these vertically connected modules. The fridge module 128 also has a robotic device 160. The robotic device 160 may be any of the robotic devices described herein. Stacked vertically on top of the fridge module 128 is an incubator module 124. This incubator module 124 and fridge module 128 have an interface such that plates 116 (or other plastic-ware) can be transferred between them by vertical movement of a robotic device 160. The incubator 124 also has a robotic device 160 for grabbing plates. The robotic device 160 may be any of the robotic devices described herein. A plate de-lidder can optionally be present in the incubator 124. Arranged horizontally to the incubator module 124 is a process module 120. Therefore, the process module 120 is stacked vertically on the freezer module 126. However, there is no interface between the process module 120 and freezer module 126. The process module 120 may have a microscope, vial decappers and a liquid handler. It also has a turntable/carousel 108. However, in this example, no robotic device 160 is provided in the process module 120 for handling plates 116. Instead, plates 116 are placed on the carousel 108 and the other devices within the module carryout operations.

The incubator 124 and the process module 120 interface such that the robotic device 160 of the incubator can pass a plate 116 from the incubator onto the carousel 108 of the process module 120. The process module is horizontally connected and interfaced to a plastic-ware store 122. The plastic-ware store 122 may also contain reagents at room temperature. As the freezer 126 and process module 120 are both horizontally connected to the plastic-ware store 122, the plastic-ware store 122 is a double height module compared to the other modules 100 in the system 99. For instance, the modules can be approximately 70 $cm^3$ cubes. However, a double height module can have a height of approximately 1.4 m. Two modules of the same specification, i.e. two plastic-ware stores 122, could also be stacked vertically for the same effect. However, such an arrangement can reduce costs of robotic devices and sealed interfaces where a single module 100 is unlikely to be large enough for the functions required. The plastic-ware store 122 of FIG. 10 has a robotic device 160 that grabs plates and can pass the plates 116 (or other plastic-ware) to and from both the process module 120 and the freezer 126.

As is clear from the description above, the modules 100 thus have an interface format that is compatible with each other such that stacking of modules is possible. This is particularly the case with the cuboid construction of a module and any oversized modules being whole number multiples of that cuboid shape. In particular, it allows the increase of capacity of the plastic-ware store 122 by stacking on another store 122. The capacity of the plastic-ware store 122 is likely to be limiting in some cases. Therefore, this arrangement allows the system 99 to run autonomously for longer periods without being re-stocked, e.g. over weekends and holidays, while maintaining the modular nature. In some embodiments, the system 99 has the capacity to culture at least 150 to 200 cell culture plates.

This further requires a fridge 128 with a capacity equivalent to about 100 plates, to store sufficient medium and other liquids to be able run unattended. Specifically, if each plate on average requires 10 mL of medium every two days, then 200 plates require 1,000 mL of medium per day. Deep-well plates hold about 192 mL of liquid, so three days' supply of medium requires 16 plates (i.e. 3×1,000 mL/192 mL), and deep-well plates require at least twice the height of cell culture plates, so the medium alone requires the equivalent of 32 slots in plate slots. The PBS, trypsin, etc., require more than another 40 slots. The plastic-ware store 122 may require a capacity equivalent to around 400 cell culture plates, depending on whether it contains pipette tip boxes.

Therefore, processing such a large number of plates places considerable load on the robotic devices of the system 99. A liquid handler 340 (discussed in detail below) can be working near to capacity. This in turn may require the cycle time to be minimized, which may require plate transfer time (in and out of the process module 120), to be minimized. The robotic device 160 can work in series with the liquid handling robot 340, as the liquid handler 340 may not be able to work while the process module 120 is being loaded or unloaded. For instance, if a robotic device 160 were transferring items to and from the process module 120 from the plastic-ware stores 122, this could become a bottleneck that reduces the effective system capacity.

Further, traffic of plates may become an awkward problem. Specifically, a robotic device 160 transferring plates 116 into and out of the process module 120 has traffic in two directions, in the sense that plates pass 'through' the robotic device 160 in two different directions: into the process module; and out of the process module. This two way traffic, particularly in a highly utilized robotic device 160, may become challenging to handle efficiently, and may contribute to the robotic device 160 becoming a bottleneck. Therefore, in some embodiments, the system 99 uses 'buffering'. That is, providing plate slots 110 that are temporarily used for the traffic of lab-ware into and out of adjacent modules 100. These plate slots 110 are referred to as buffers. Further, the transfer of the plates from the buffer to the process module, and back again, is fast, with short movements. Still further, the traffic is inherently very simple.

On the rack 210 level that is horizontally level with the interface 134, i.e. the transfer slots, the module 100 has at least one transfer slot or space that behaves as a 'pass through' slot, where the robotic device 160 can pass plates 116 through the pass through slot, through the interface 134, and into another module 100. If all of the transfer slots that are on the same level as the interface 134 are pass-through slots, then they can be used as a buffer to provide buffering.

Referring to FIGS. 11A and 11B, the steps of loading one half of the turntable of the process module 120 are shown. Plates or other lab-ware may be placed in buffer slots 1 to 3 (referred to as 211, 212, 213 on the FIG. 11A) of a module 100 (e.g. an incubator 124) that interfaces with the process module 120. A robotic device 160 of the module 100 can pick plates 116 from any slot 110 in the module 100, and place them in appropriate buffer slots 211, 212, 213 (as previously discussed, in embodiments this is via a combination of vertical and radial movements in a single plane of the robotic device 160, and rotating of the carousel 108). Referring to FIG. 11B, the plates 116 can be placed in an order that results in the plates ending up in a desired location on the process module turn table/carousel 108. This buffering can be done while the process module 120 is working (e.g. performing liquid handling).

Considering the steps of loading the process module 120, the carousel 108 of the store module 100 rotates to align e.g. buffer/transfer slot 1 211 with the interface 134 to the process module 120. The carousel 108 of the process module 120 rotates, to align a transfer slot with the interface 134. The robotic device 160 of the store module 100 then pushes the first plate 116 from the transfer slot, through the interface 134, which may have a door 130 to be opened as required, and into the transfer slot of the carousel 108 of the process module 120, and the robotic device 160 retracts into the center well 112 of the carousel 108 of the store module 100. The carousel 108 of the module 100 then rotates, to align the next transfer slot, buffer slot 2 212, carrying the next item of lab-ware to be transferred, with the interface 134. Simultaneously, the carousel 108 of the process module 120 rotates to align the next transfer slot to the interface 134. The robotic device 160 then pushes the second plate from the transfer slot, through the interface 134, into the transfer slot on the process module carousel 108, and then retracts to the center well 112 of the carousel 108 of its module 100. The operation is repeated one more time to transfer the remaining plate. In this example, the carousels 108 of the process module 120 and respective storage module 100 can rotate to the next plate slot 110 on the carousel 108 to start the next operation. Therefore, for a carousel 108 with eight plate slots 110 on a horizontal plane, the carousel 108 would only need to rotate ⅛$^{th}$ of a full rotation. This reduces the movement and thus time between transfer operations.

While the preceding example describes a single module 100 feeding plates into the process module 120, more modules can feed into a process module 120 simultaneously. In some embodiments, these modules will generally be on opposite sides of the process module 120. This will allow for the most efficient transfer to the process module 120 as each half of the carousel 108 of the process module 120 would be filled (or emptied) simultaneously.

In an embodiment, shown in FIGS. 12A to 12F, the two modules 100 will be the incubator 124 and a plastic-ware store 122. These two modules 100 feed the most items to the process module 120. FIG. 12A shows the flow of the plates 116 using the illustrative arrows. Further, unloading and loading of the process module 120 will typically happen in sequence, with no pause. Typically, each module 100 will load approximately four plates to its buffer, i.e. transfer slots, ready to be transferred to the process module 120. FIG. 12B shows a starting position where the modules 100 are buffered and the process module 120 is full of plates 116. If, for instance as shown, the carousel 108 of the process module 120 holds eight plates, and the carousels 108 of the modules 100 have eight buffer positions, then the combined capacity of the two module 100 can buffer up to eight plates 116 in the transfer slots. FIG. 12C shows the first transfer of the plates 116. In use, one module 100 can buffer more than half this total, and the other module 100 can buffer the remainder of the total as per the requirements of the system 99. Likewise, each module 100 will typically leave four transfer slots in its buffer empty, ready to receive items from the process module 120. As with the above, the plate 116 can be organized on the transfer slot layer so that they are required in adjacent slots, so only a series of ⅛$^{th}$ turns are required, this is shown in FIG. 12D where the carousels 108 all rotate one slot. The whole unloading of the process module 120 is shown in FIG. 12E where the modules 100 have a mix of plates that have been unloaded from the process module 120 and are to be loaded. FIG. 12F then shows the first step of loading the process module 120.

Considering the larger system 99, such as the one shown in FIG. 10, plates 116 can be buffered from other module 100 to the modules 100 that interface with the process module 120. For instance, medium is typically stored in the fridge 128, but pre-warmed in the incubator 124. Frozen items may be buffered in the fridge 128, plastic-ware store 122, or incubator 124, as required. Therefore, the system 99 is able to transfer plates 116 from one module 100 to another while the process module 120 is working. For example, the fridge 128 can transfer to the incubator 124 while the process module 120 is working to minimize cycle times. In this example (not shown), the fridge 128 is interfaced to a plastic-ware store 122, and the plastic-ware store 122 to the incubator 124, so as to minimize temperature disturbances during the transfer. Likewise, as stated elsewhere, it is advantageous for the freezer 126 to be interfaced to the fridge 128, and for the system 99 to access the freezer 126 through the fridge 128, to minimize temperature disturbances in the freezer 126.

The plate slots 110 are shown in FIG. 12A to FIG. 12F as having the wider edge facing the center well 112. The orientation of the plate slots 110 can be altered as required for the best efficiency.

Vertically stacked modules 100 also allow for human-accessible doors positioned on an outer side of a module 100 through which the system 99 is restocked, e.g. with fresh lab-ware at a convenient height. Such an outer door can be positioned on e.g. a plastic-ware store 122 or a fridge 128. Alternatively, there may be a dedicated load-lock, which is the only module 100 with a door that is routinely human-accessible, through which users can exchange consumables, plates with cells, or samples, with the system 99.

Stacking modules vertically also allows for a door in an incubator 124 (either an interface door 130, 230 or an outer door for human access) to be placed low on the wall, to minimize warm, humidified, $CO_2$ rich air flowing out when the door is opened. It also allows for the fridge 128 and freezer 126 to be placed low in the system 99, which means the doors (either interface doors 130, 230 or an outer door for human access) to be placed high on the sides, which minimizes cold air flowing out of those stores 126, 128 when the doors are opened.

Other possible embodiments, illustrating how the module and interface innovations are not restricted to being used with carousels, but could be used with, for example, conventional robotic arms, or gantry robots, or similar.

Figure 28A:
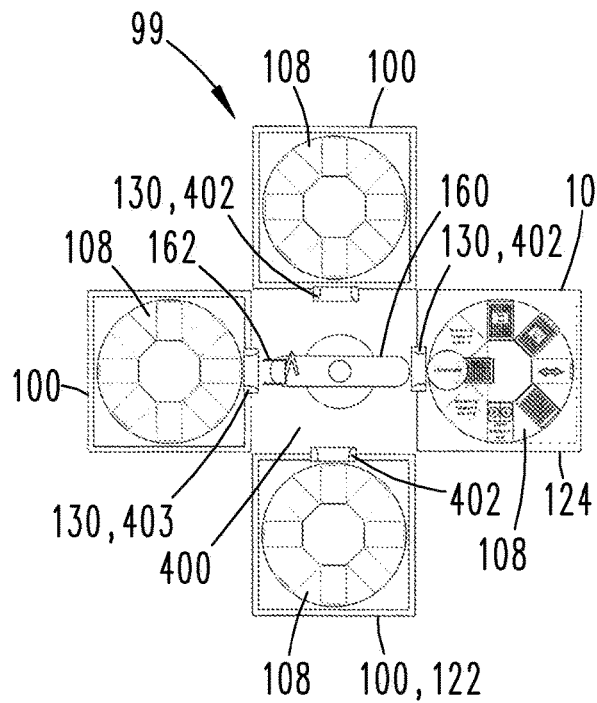
FIG. 28A shows a plan view schematic of a system of modules with a central robotic handler according to an embodiment.

Referring to FIG. 28A, there is a robot device 160 in the center 400 of four modules 100. The arm 160 rotates about a central axis, the grabber 162 moves translationally, so as to be able to move plates 116 in and out of the modules 100, and the robotic device 160 travels vertically along the central axis. One of the modules can be a plastic-ware store 122. The plastic-ware store 122 optionally has full height vertical doors 402, to allow the robotic device 160 access to any level in the internal racks 210. Other doors can be full height doors 402 as well. The carousels 108 in the modules 100 rotate to allow access to the required plate slots 110. The rotating of the carousel 108, and the vertical movement of the robotic device 160 would allow the robotic device access to any plate slot 110 in the modules 100. Therefore, a combination of movements of the robotic device 110 (rotating about its axis, moving along its axis, and translating in and out of the modules 100), together with rotating of the carousels 108, or rotating of the working deck carousel 108 in the process module 124, allow the robotic device 160 to transfer any plate 116 anywhere in the system 99. This has the advantage that the movements are simple and easy to program, and from the hardware point of view, simple and reliable.

The grabber 162 may be mechanically or optically (e.g., using machine vision or optical or magnetic sensors) indexed or aligned to the doors 402 or interfaces 130. The interfaces 130 may have mechanical aligning features, as already described, including features such as chamfers, or features such as pin and slot features. The grabber 162, or a wrist on the grabber 162, may have some compliance, to allow aligning with aligning features such as chamfers. The robotic device 160 can be aligned such that the chamfers (e.g. on the doors 402) are not normally contacted by the grabber 162 as it transits the door 402, but the grabber 162 only contacts the chamfers if it is mis-aligned. Contact with the chamfers may dynamically or mechanically correct for mis-alignment. The chamfers may correct the grabber 162 in the horizontal, or vertical planes, or both. Contact with the chamfers may further provide feedback, which could be used to correct the alignment of the robotic device 160.

Figure 28B:
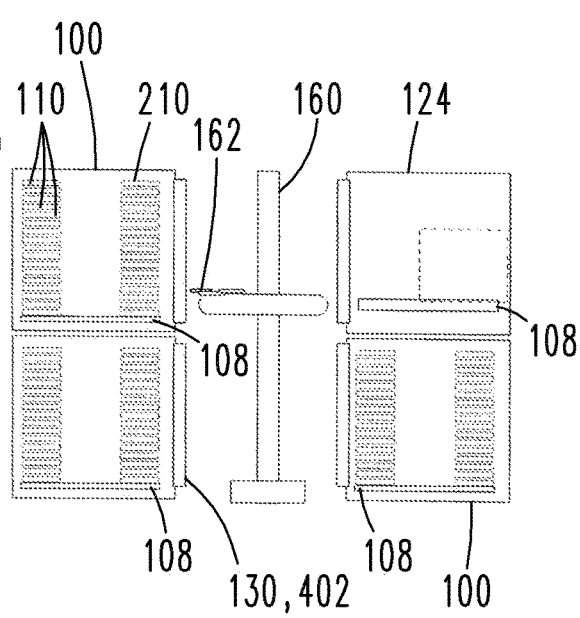
FIG. 28B shows a side view schematic of a system of vertically stacked modules with a central robotic handler according to an embodiment.

FIG. 28B shows a side view of the robotic device 160 placed in the center 400 between modules 100. Here vertically stacked modules 100 are provided. The robotic device 160 can have vertical movement so that all modules 100 can be reached through doors 402 or interfaces 130. The carousel 108 with the rack 210 or working deck 330 positioned thereon can be rotated so that the robotic device 160 can access the require plate slot 110.

Figure 30:
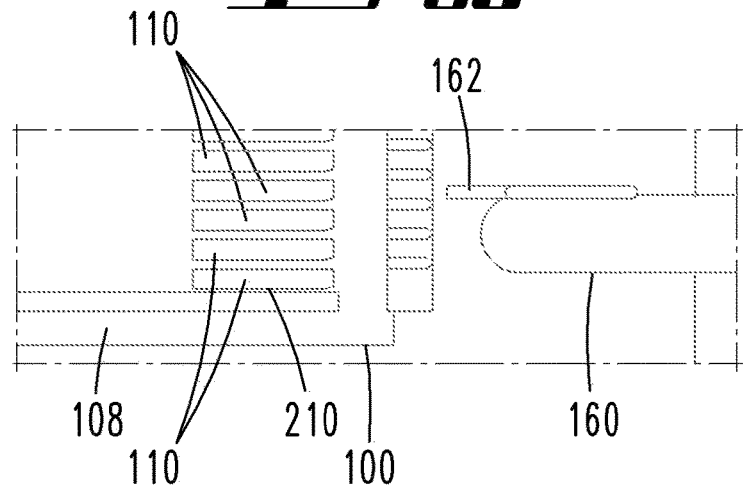
FIG. 30 shows a magnified side view schematic of a robotic handling device and a rack of a module.

Referring to FIG. 30, a magnified view of a robotic device 160 interacting with a rack 210 of a module 100 is shown. Here the grabber 162 is sized such that it can extend into a module to grab the relevant lab-ware 300.

The system 99 as described previously, for example in FIGS. 28A-28B, can have standardized interfaces, also as already described. The system 99 may have a rotating working deck 330, as already described. The system 99 may have a standardized lab-ware set 300, allowing all the lab-ware 300 to be handled in the same way. The system 99 may use methods already described, which allow complex workflows to be executed autonomously by the system 99, using only the set of complete lab-ware described 300, in an SLAS micro plate 116 format. These features may all be used, singly or in combination, to enable simple, reliable handling with a single robotic device 160 in a center 400 of modules 100. The use of these features in combination may enable the system to achieve a mean time between failures of greater than 30,000, or greater than 60,000 plate transfer or movement events, where 'meantime between failures' means the arithmetic mean of the number of plate transfers or movements, between failures, where a failure is an error that causes the system to stop until a human can fix the problem.

Alternatively, a more flexible robot arm can be used, such as six-axis arms. Machine vision may be used to augment the system, to increase reliability. The system 99 can be laid out on one level, horizontally. A robotic device 160 can run on rails, which are indexed to the doors 402 or interfaces 130.

Figure 29A:
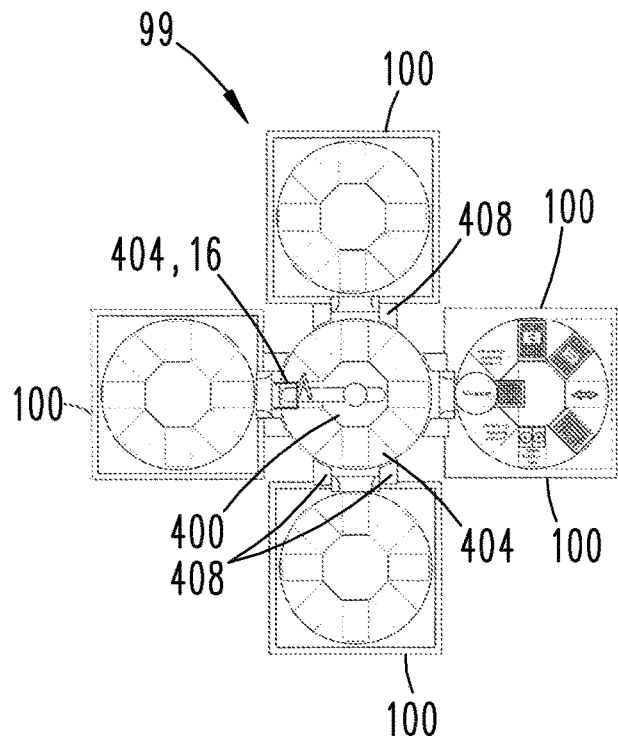
FIG. 29A shows a plan view schematic of the system of FIG. 28A with an additional carousel.
Figure 29B:
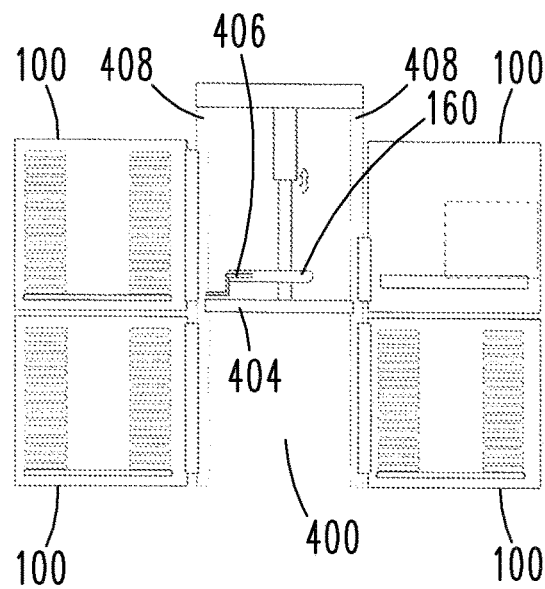
FIG. 29B shows a side view schematic of the system of FIG. 28B with an additional carousel.

Referring to FIGS. 29A and 29B, the robotic device 160 can again be positioned in a center 400 with modules around it. However, the robotic device 160 can be an arm 406 that populates a turntable 404 that is also positioned in the center 400. The arm 406 can transfer plates 116 horizontally between plate slots 110 in the modules 100 and a turntable 404. The arm 406 further may rotate about a central axis, to access other modules 100. The arm travels vertically along the central axis. The turntable 404 also travels vertically, and rotates. There may be vertical rails 408, to support the robotic device 160, and maintain alignment, or to connect or index it to the doors or interfaces.

In an embodiment of FIGS. 29A and 29B, the turntable 404 may function as a temporary storage or magazine, and the plates 116 may be transferred from there to the carousel 108 in the process module 124.

Figure 31A:
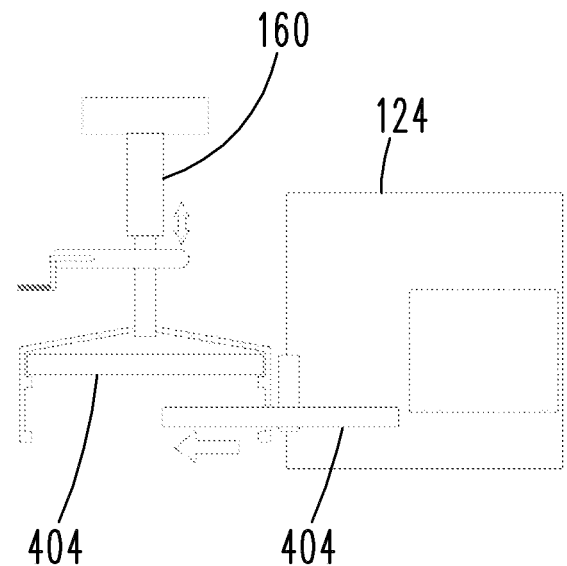
FIGS. 31A and 31B show a side view schematic of a robotic turntable handling device according to an embodiment.
Figure 31B:
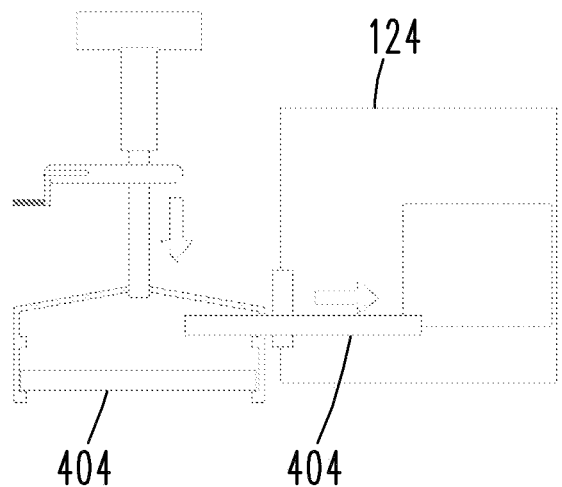

Referring now to FIGS. 31A and 31B, the turntable 404 may be passed into the process module 124. There may further be two turntables 404, so that one can be in the process module 124 where work is being done, and the second one can be loaded while the first is being worked on. The turntables 404 can then be exchanged.

Figure 32:
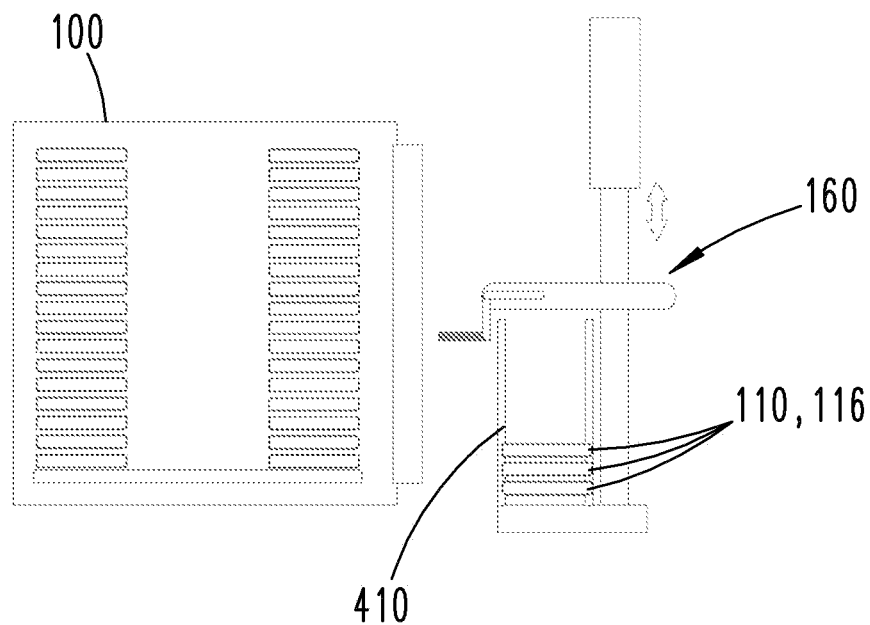
FIG. 32 shows a side view schematic of a robotic handling device with a magazine rack and a module according to an embodiment.

FIG. 32 shows a robotic device 160 with a magazine 410 which is a vertical rack. The robotic device 160 gathers the plates 116 and other lab-ware 300 for the next workflow into the magazine 410, then transfers them from the magazine 410 into the process module 124. This avoids delays with the robotic device 160 traveling between various modules 100 and the process module 124 with one item at a time. The robotic device 160 may further have two magazines 410. It may load up one magazine 410 with the next items to be loaded into the process module 124. It then unloads the process module 124 into the second magazine 410, and re-loads the process module 124 from the first magazine 410, then unloads the second magazine 410 into the relevant modules 100.

Figure 33:
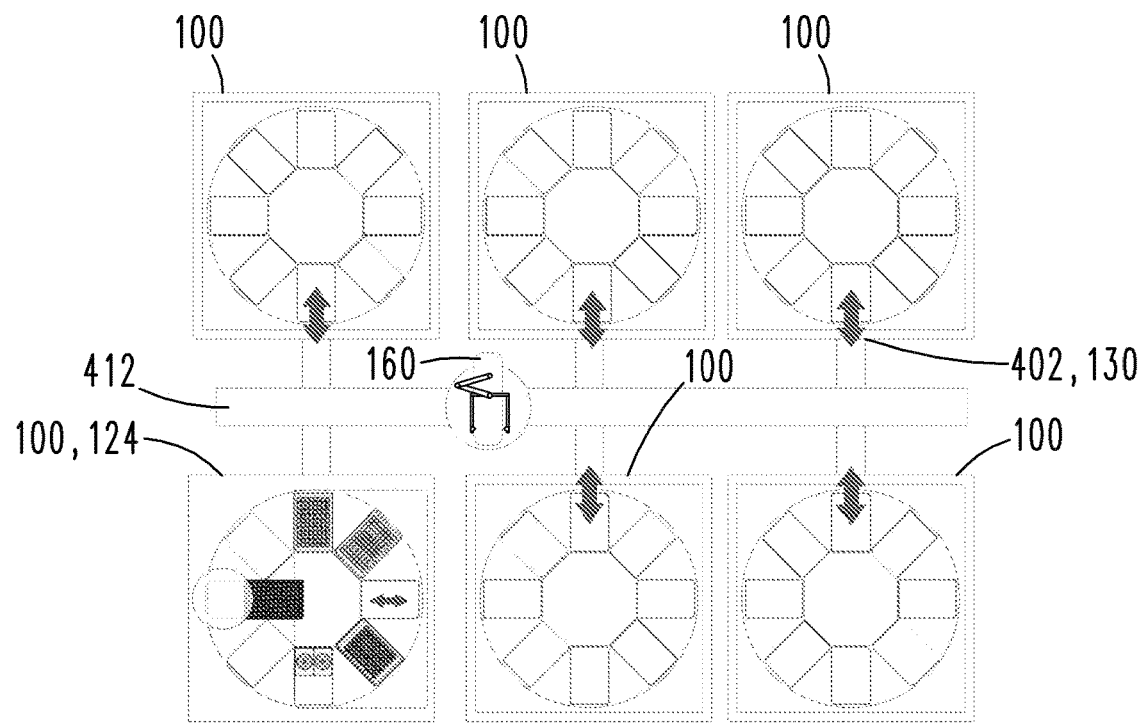
FIG. 33 shows a plan view schematic of a system of modules and a robotic device on a rail according to an embodiment.

Referring to FIG. 33, the modules 100 can be arranged in two facing rows. They can be accessed by a robotic device 160 that travels between them on a rail 412 or a similar fixed track, such as a gantry. The robotic device 160 can be mechanically or optically indexed to the doors 402 or interfaces 130 on the modules 100 for example, the robotic device 160 may move on a rail which is fixed or to the doors 402 or interfaces 130.

With the robotic device 160 of FIG. 33, it may be desirable to avoid one or more of a heavy robotic device 160, or a long travel distance, thus long rails 412, or high travel speeds, as this may make the system vulnerable to going out of alignment. While robots may be very intrinsically accurate, the mechanism or fixtures by which the robot is fixed or aligned to modules can flex, warp or drift, and thereby go out of alignment.

The modules 100 do not need to be limited to using carousels 108, but instead use modules 100 with racks 210 that are rectangularly arranged, and access to the racks 210 could be via a rail or rotating rack system. Rectangularly arranged racks are more space-efficient and denser than carousels 108.

Therefore, the previously described systems 99 can use a robotic device 160 that sits outside the modules 100. This is made practical by the simplified handling described previously (constrained movements along constrained axes, horizontal transfers, fixed interfaces, single plastic-ware handling format, etc.). The robotic device 160 can interface to the interfaces 130 on the modules 100; for instance, the grabber 162 might index to, or align onto the doors 402. The robotic device 160 can run on rails 412, where the rails 412 are fixed to the interfaces 130. The modules 100 can have a fixed interface format.

Figure 34:
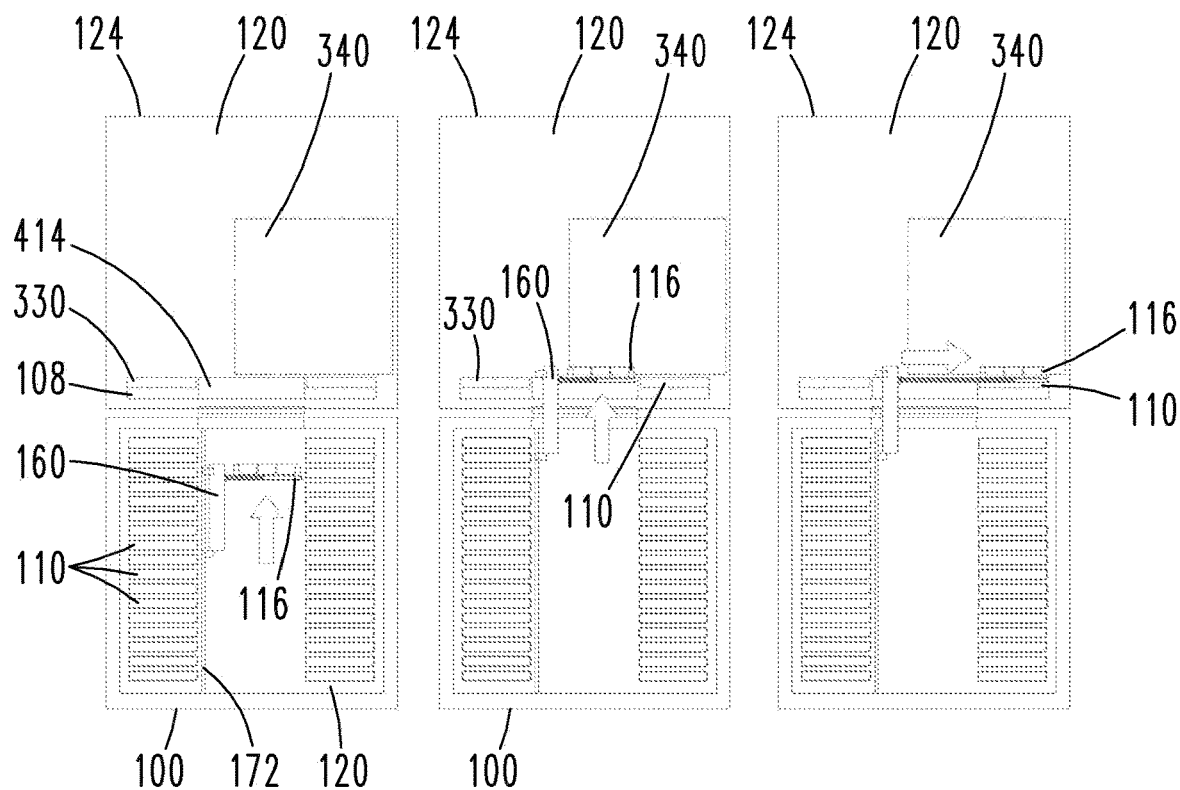
FIG. 34 shows a side view schematic of the steps of a vertically stacked module transferring a plate between the modules according to an embodiment.

Referring to FIG. 34, an operation sequence is shown when the image is considered from left to right. A module 100 having racks 210 with plate slots 110 is provided. Stacked vertically on the module 100 is a process module 124. The robotic device 160 travels between the modules 100 on rail 172 as discussed previously with reference to FIGS. 9A and 9B. However, the process module 124 does not have racks 210 as the space of the process module 124 is occupied by liquid handlers, de-capping machines, etc. Therefore, the process module 124 has a carousel 108 with a working deck 330. To deliver lab-ware 300 and plates 116 to the working deck 330, a center portion of the working deck 330 is not occupied such that the robotic device 160 can partially pass through it, much like the center well 112 that is already described. As shown in successive images, the robotic handler 160 can pass partially into the process module 124 and hand off the plate 116 into the target plate slot 110 on the working deck 330. Therefore, allowing a vertical delivery of plates 116 and lab-ware 300. This can reduce space needed in the process module 124 for transfer of plates 116 and due to the possible lack of rails 172 needed for a vertical transfer.

Although the illustrated examples above show the modules implemented as rotating features (e.g. carousels with plate hotels), those skilled in the art will realize that the features and principles described can be applied to other sorts of modules or transfers.

Figure 35:
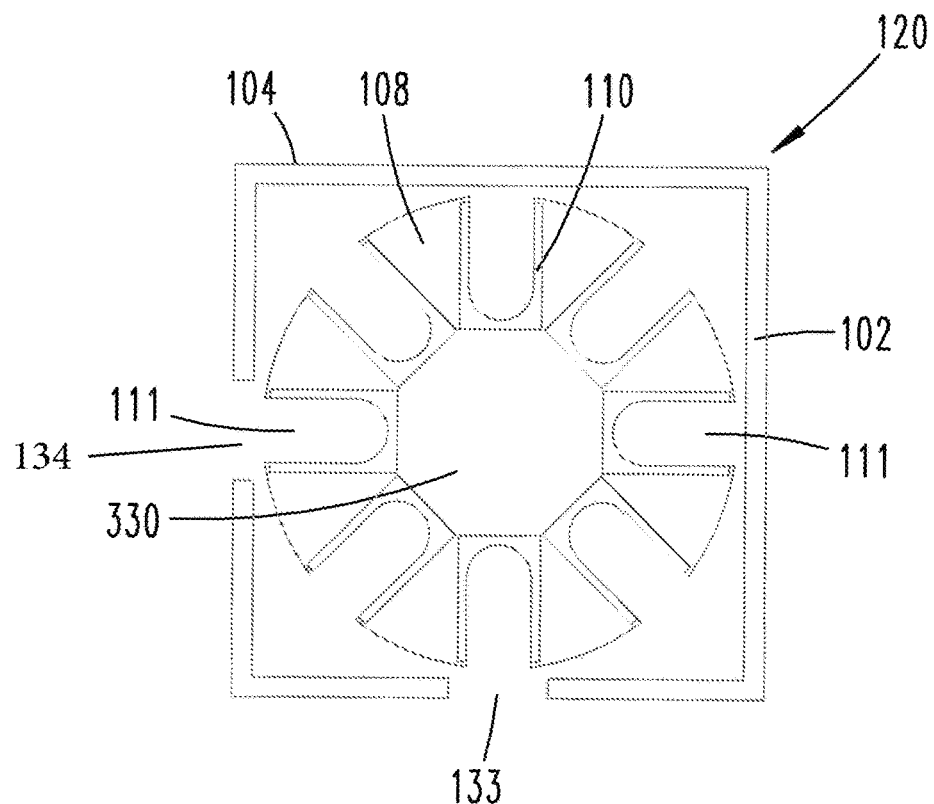
FIG. 35 shows a plan view as FIG. 1 of an additional embodiment of the invention.

FIG. 35 shows an alternative device as disclosed in FIG. 1.

The working desk plate slots 110 have windows 111, which are open to the upper side and the lower side of the working deck 330. The windows 111 are used for an arm of a gripper (not shown) to lift a plate, for example a cell culture plate 116 out of the working desk plate slot 110. The gripper may have a tray with a protrusion fitting into a recess of an underside of a plate.

FIG. 35 further shows first transfer interface 133 and second transfer interface 134 being located at different positions with respect to the housing 102 or the rotatable working deck 330. First transfer interface 133 can be in communication with a first storage module (not shown in FIG. 35, but described above). Second transfer interface 134 can be brought into communication with a second storage device (not shown in FIG. 35, but disclosed above). One of the storage modules may store cell culture plates 116 as disclosed above. The other storage module may store lab-ware as described above or liquid media for applying to the cell culture plates as described above.

Figure 36:
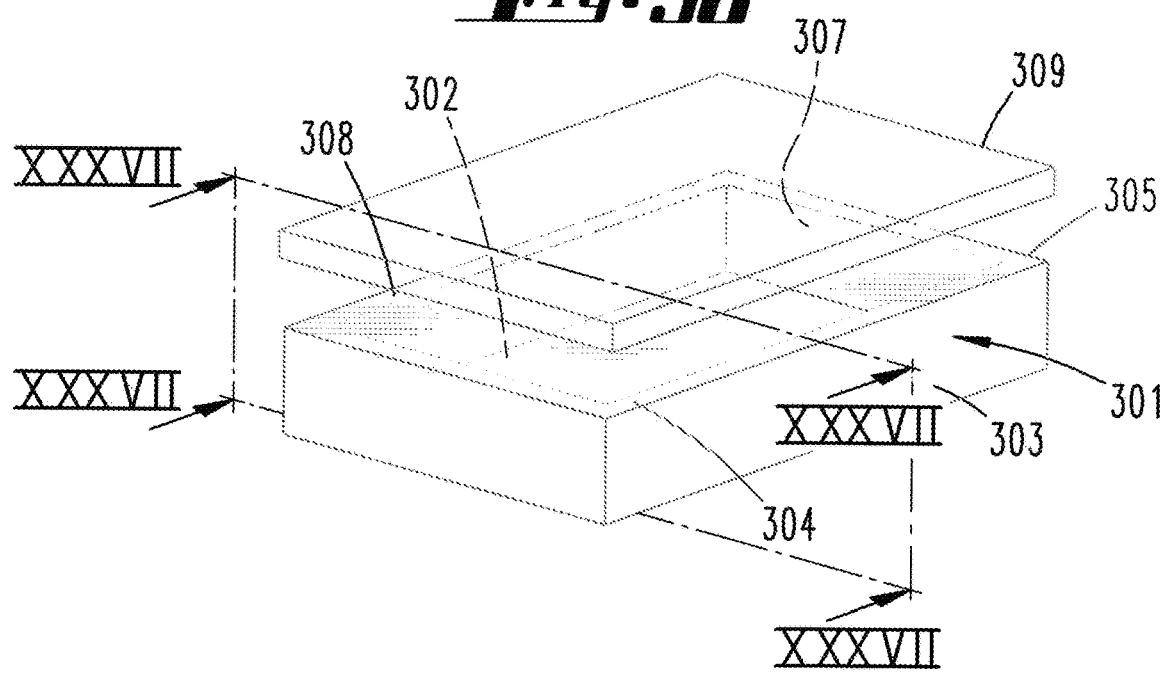
FIGS. 36 and 37 show a single well plate for storing liquid media.
Figure 37:
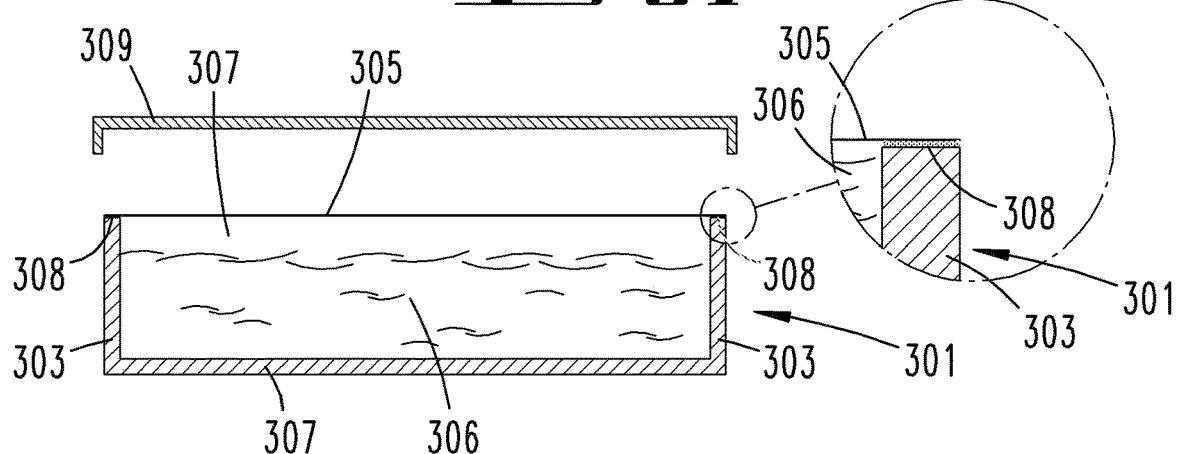

FIGS. 36 and 37 show a single well plate 301 having a bottom 302 of rectangular shape. The single well plate 301 has a microplate footprint as described above (width 85.5+/−1 mm; length 127.8+/−1 mm).

The single well plate 301 comprises four walls 303 with an upper edge 304. A foil (plastic foil) is sealed to the edge 304 and covers the top aperture of the well 307 enclosed by the wall 303. The connection of the foil 305 with the edge 304 is a heat-seal-connection 308. The plate 301 can be used to transport liquid media 306 from a supplier to a biology laboratory system. The sealed aperture of the plate 301 can be covered by a lid 309.

The foil 305 can be broken by a tip of a pipette of a liquid handler 340 to aspirate the liquid 306 stored inside the well 307.

Figure 38:
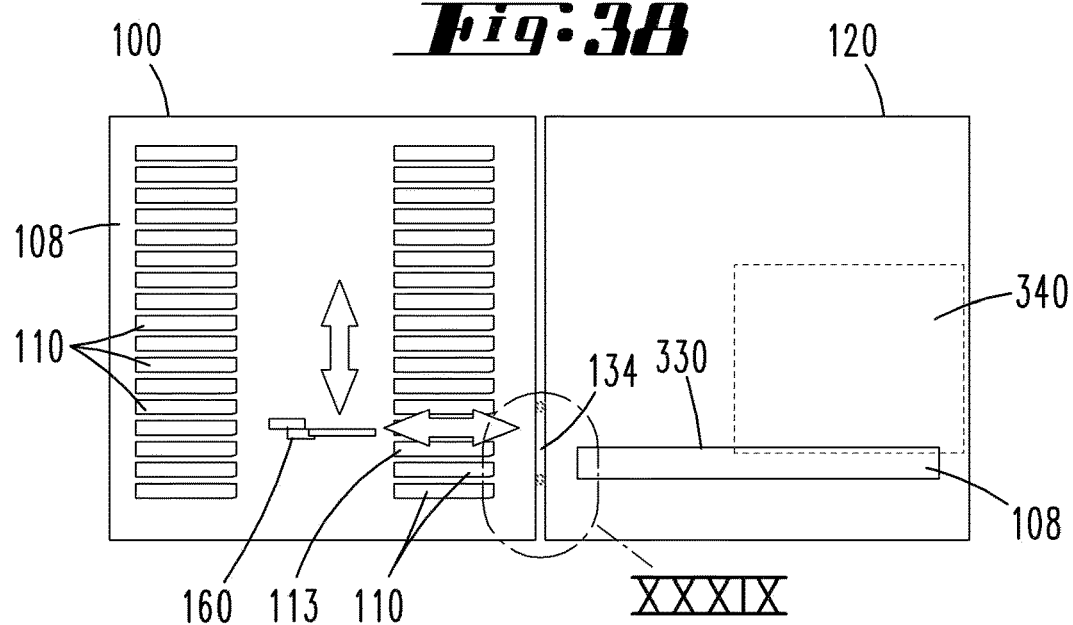
FIGS. 38 and 39 show two adjacent modules being connected with a sealing element 311.
Figure 39:
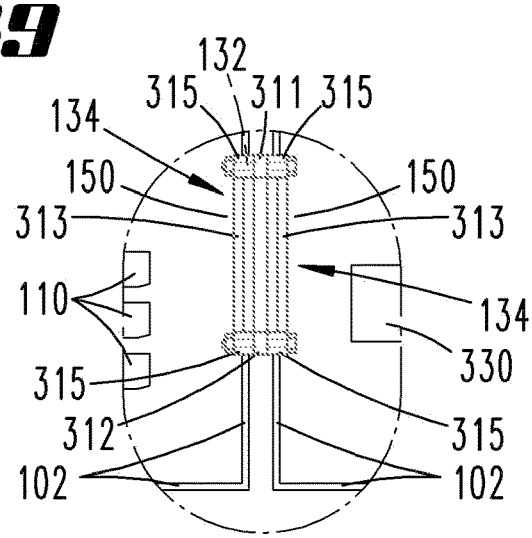

FIGS. 38 and 39 show a sealing element 311, which forms a pass-way for a plate being moved between one module 100 and another module 120, wherein one module 100 can be a storage module and the other module 120 can be a process module or a storage module 100 as well. The height of the aperture 150 formed by the frame 315 and the sealing element 311 being located between the frame 315 can be greater than shown. The height of the interface 134 is just sufficient for moving a microplate through the interface 134. The interface 134 may have a uniform height, which is larger than the height of a bottle or the highest device being stored in a module 100.

All these features combine to make lab-ware handling much simpler and more reliable, to make the software faster and easier to write and debug, and ultimately for the software of the system to be stable. This is in contrast to the state of the art, where unstable software is one of the major factors preventing.

What is claimed is:

1. A biological laboratory system comprising:
   a process module (120);
   a first carrier (116) carrying biological material;
   a second carrier carrying lab-ware (300) or liquid;
   a first storage module (124) and a second storage module (122), the process module (120) comprising:
   a housing (102);
   a rotational element (108) located within the housing (102);
   a working deck (330) located within said housing (102), having a plurality of plate slots (110) including a first plate slot (110) for receiving the first carrier (116), and a second plate slot (110) for receiving the second carrier, wherein the working deck (330) is formed by a top surface of the rotational element (108);
   a liquid handling robot (340) located within the housing (102) and disposed above the working deck (330), the liquid handling robot (340) comprising at least one pipette configured to aspirate the liquid carried in the second carrier;
   a first transfer opening (133) on the housing (102), the first opening (133) configured to fluidly connect the process module (120) and the first storage module (124) located outside of the housing (102) of the process module (120);
   a second transfer opening (134) on the housing (102), the second opening (134) configured to fluidly connect the process module (120) and the second storage module (122) located outside of the housing (102) of the process module (120), wherein the working deck (330) is movable between a plurality of working positions, the plurality of working positions including:

a first working position in which the first carrier (116) is located under an operating point of the liquid handling robot (340), a second working position in which the first plate slot (110) is in alignment with said first transfer opening (133), and a third working position in which the second plate slot (110) is in alignment with said second transfer opening (134), wherein the first and second plate slots (110) are identically sized, having a microplate footprint configured to be used for all carriers in the process module (120), and wherein the first and second plate slots (110) are radially arranged with respect to an axis of rotation of the working deck (330), wherein the alignment of the first plate slot (110) and the second plate slot (110) in the second and third working positions, respectively, is a radial alignment, means for transporting the first carrier (116) in a linear horizontal motion through the first transfer opening (133), while the working deck (330) is located in the second working position; and means for transporting the second carrier in the linear horizontal motion through the second transfer opening (134), while the working deck (330) is located in the third working position; and a controlling unit programmed to perform steps comprising:

transferring the first carrier (116) from the first storage module (124) through the first transfer opening (133) to the first plate slot (110);

transferring the second carrier through the second transfer opening (134) from the second storage module (122) to the second plate slot (110);

moving the working deck (330) from one of the working positions to another one of the working positions;

aspirating the liquid with the liquid handling robot (340) from the second carrier carrying the liquid;

applying the liquid to the first carrier (116) by using the lab-ware (300);

moving the working deck (330) from one of the working positions to another one of the working positions; and discharging the first carrier (116) through the first transfer opening (133).

2. The biological laboratory system of claim 1, further comprising one or more of the following positioned above the working deck (330): a microscope (942), a capper/de-capper robot (344) configured for de-capping vials (321) and bottles (323) or a lidder/de-lidder robot (346) configured for de-lidding the first and second carriers.

3. The biological laboratory system of claim 1, wherein the first plate slot (110) is recessed into a surface of the working deck (330).

4. The biological laboratory system of claim 1, wherein each of the plurality of plate slots (110) comprises an alignment means (144) at an outer edge of the working deck (330), and wherein the alignment means (144) defines a width of an entrance to each of the plurality of plate slots (110) that decreases with decreasing distance to the center of the process module (120).

5. The biological laboratory system of claim 1, wherein the liquid handling robot (340) is moveable in a plane running parallel to a rotational plane of the working deck (330) to:

the second plate slot (110) to aspirate the liquid from the second carrier located at the second plate slot (110) and transport the liquid to the first carrier (116) located at the first plate slot (110); and a third plate slot to grasp tips from a pipet tip box (324) located at the third plate slot (110).

6. The biological laboratory system of claim 1, wherein the first transfer opening (133) is directly adjacent to a corresponding transfer opening of the first storage module (124), and wherein the second transfer opening (134) is directly adjacent to a corresponding transfer opening of the second storage module (122).

7. The biological laboratory system of claim 1, wherein the first plate slot (110) is open to an edge of the working deck (330).

8. The biological laboratory system of claim 1, wherein the first plate slot (110) comprises a first recess (111) for a handling arm reaching into the recess (111) under the first carrier (116) being located in the first plate slot (110) for lifting the first carrier (116), and wherein the second plate slot (110) comprises a second recess (111) for the handling arm reaching into the second recess (111) under the second carrier (116) being located in the second plate slot (110) for lifting the second carrier.

* * * * *